(12) United States Patent
De Nobel et al.

(10) Patent No.: US 7,592,420 B2
(45) Date of Patent: *Sep. 22, 2009

(54) EXPRESSION IN FILAMENTOUS FUNGI OF PROTEASE INHIBITORS AND VARIANTS THEREOF

(75) Inventors: Hans De Nobel, Almere (NL); David A. Estell, San Mateo, CA (US); Wei Liu, Palo Alto, CA (US); Scott D. Power, San Bruno, CA (US); Brian Schmidt, Half Moon Bay, CA (US); Huaming Wang, Fremont, CA (US)

(73) Assignee: Genencor International, Inc., Palo Alto, CA (US)

( * ) Notice: Subject to any disclaimer, the term of this patent is extended or adjusted under 35 U.S.C. 154(b) by 208 days.

This patent is subject to a terminal disclaimer.

(21) Appl. No.: 11/848,196

(22) Filed: Aug. 30, 2007

(65) Prior Publication Data

US 2008/0234465 A1   Sep. 25, 2008

Related U.S. Application Data

(63) Continuation of application No. 10/971,596, filed on Oct. 22, 2004, now Pat. No. 7,279,564.

(60) Provisional application No. 60/518,154, filed on Nov. 6, 2003.

(51) Int. Cl.
*C07K 14/42* (2006.01)
*C07K 14/81* (2006.01)

(52) U.S. Cl. ................... 530/324; 530/378; 435/69.2

(58) Field of Classification Search ............. None
See application file for complete search history.

(56) References Cited

U.S. PATENT DOCUMENTS

| | | | |
|---|---|---|---|
| 4,486,553 A | 12/1984 | Wesch | |
| 4,935,349 A | 6/1990 | McKnight et al. | 435/69.5 |
| 5,364,770 A | 11/1994 | Berka et al. | |
| 5,365,770 A | 11/1994 | Meitzler et al. | |
| 5,411,873 A | 5/1995 | Adams et al. | |
| 5,429,950 A | 7/1995 | Power et al. | |
| 5,646,025 A | 7/1997 | Moyer | 435/192 |
| 5,679,543 A | 10/1997 | Lawlis | |
| 5,702,934 A | 12/1997 | Hastrup et al. | 435/183 |
| 5,705,358 A | 1/1998 | Gouka et al. | 435/69.1 |
| 5,710,021 A | 1/1998 | Hintz et al. | 435/69.1 |
| 5,830,733 A | 11/1998 | Nevalainen et al. | 435/196 |
| 6,391,848 B1 | 5/2002 | De Lumen et al. | 514/2 |

FOREIGN PATENT DOCUMENTS

| | | |
|---|---|---|
| EP | 0 137 280 A1 | 4/1985 |
| GB | 2 200 118 | 7/1988 |
| WO | WO 94/13820 A1 | 6/1994 |
| WO | WO 96/239285 | 8/1996 |
| WO | WO 00/05406 A1 | 2/2000 |
| WO | WO 2004/003186 | 1/2004 |

OTHER PUBLICATIONS

Xin et al. ("The amino acid sequence of Kunitz-type soybean trypsin inhibitor, Tid, derived from its nucleotide sequence and its comparison with Tia," Zhongguo Shengwu Huaxue Yu Fenzi Shengwu Xuebao, 1999, 15, 671-673, CAS 131:348242).*
Jofuku et al. ("A frameshift mutation prevents Kunitz trypsin inhibitor mRNA accumulation in soybean embryos," Plant Cell , 1989, 1, 427-35, CAS 1990:435634).*
Brauer, A.B.E., et al., "The $^1$H-NMR Solution Structure of the Antitryptic Core Peptide of Bowman-Birk Inhibitor Proteins: A Minimal 'Canonical Loop'", *Journal of Biomolecular Structure & Dynamics*, 20(1):59-70, 2002.
Clemente, A. et al., "The effect of variation within inhibitory domains on the activity of pea protease inhibitors from the Bowman-Birk Class", *Protein Expression and Purification*, 36:106-114, 2004.
MacKenzie, D.A., et al., "Aberrant processing of wild-type and mutant bovine pancreatic trypsin inhibitor secreted by *Aspergillus niger*", *Journal of Biotechnology*, 63(2):137-146, 1998.
Baek et al., "Nucleotide Sequence Homology of cDNAs Encoding Soybean Bowman-Birk Type Proteinase Inhibitor and Its Isoinhibitors,"*Biosci. Biotech. Biochem.*, 58(5):843-846 (1994).
Ballance, D. J. et al., "Transformation of *Aspergillus nidulans* by the Orotidine-5'-Phosphate Decarboxylase Gene of *Neurospora Crassa*" (1983) *Biochem Biophys. Res. Commun*. vol. 112, No. 1, pp. 284-289.
Barclay, Stephen et al., "Efficient Transformation of *Dictyostelium discoideum* Amoebae," *Molecular and Cellular Biology*, vol. 3, pp. 2117-2130, Dec. 1983.
Billings et al., "A growth-regulated protease activity that is inhibited by the anticarcinogenic Bowman—Birk protease inhibitor," *Pro. Natl. Acad. Sci.* 89:3120-3124 (1992).
Birk, "The Bowman-Birk inhibitor," *Int. J. Pept. Protein Res.* 25:113-131 (1985).
Blond-Elguindi et al., "Affinity Panning of a Library of Peptides Displayed on Bacteriophages Reveals the Binding Specificity of BiP," *Cell*, vol. 75, pp. 717-728, Nov. 1993.
Bode & Huber, "Natural protein proteinase inhibitors and their interaction with proteinases," *Eur. J. Biochem.* (1992) 204:433-451).
Boel, E. et al., "Two different types of intervening sequences in the glucoamylase gene from *Aspergillus niger*," *The EMBO Journal*, vol. 3, No. 7, pp. 1581-1585, 1984.
Bull, John H., et al. "Heavily methylated amplified DNA in transformants of *Neurospora crassa*," *Nature*, 310:701-704.
Campbell et al., "Improved transformation efficiency of *Aspergillus niger*, using the homologous *niaD* gene for nitrate reductase," *Curr. Genet.*, vol. 16, pp. 53-56, 1989.
Case, Mary E. et al., "Efficient transformation of *Neurospora crassa* by utilizing hybrid plasmid DNA," *Proc. Natl. Acad. Sci. USA*, vol. 76, No. 10, pp. 5259-5263, Oct. 1979.
Chen et al., "Reactive Sites of an Anticarcinogenic Bowman-Birk Proteinase Inhibitor are Similar to Other Trypsin Inhibitors," *J. Biol. Chem.* (1992) 267:1990-1994; Werner & Wemmer, 1992.

(Continued)

*Primary Examiner*—Cecilia Tsang
*Assistant Examiner*—Christina Bradley
(74) *Attorney, Agent, or Firm*—Danisco US Inc.

(57) ABSTRACT

Described herein are protease inhibitors, variants thereof and methods for their production.

14 Claims, 10 Drawing Sheets

OTHER PUBLICATIONS

Fowler, Timothy et al., "Regulation of the *glaA* of *Aspergillus niger*," *Curr. Genet.*, 18:537-545, 1990.

Gouka et al., "Analysis of Heterologous Protein Production in Defined Recombinant *Aspergillus awamori* Strains," *Applied and Environmental Microbiology*, 62(6):1951-1957 (1996).

Gouka et al., "Glucoamylase Gene Fusions Alleviate Limitations for Protein Production in *Aspergillus awamori* at the Transcriptional and (Post) Translational Levels," *Applied and Environmental Microbiology*, 63(2):488-497 (1997).

Gwynne, David I. et al., "Genetically Engineered Secretion of Active Human Interferon and a Bacterial Endoglucanase from *Aspergillus nidulans*," *Bio-Technology*, vol. 5, pp. 713-719 (1987).

Hammond et al., "Molecular Cloning and Analysis of a Gene coding for the bowman-Birk Protease Inhibitor in Soybean," *J. Biol. Chem.*, 259(15):9883-9890 (1984).

Hengen, "Purification of His-Tag fusion proteins from *Escherichia coli*," (1995) *TIBS* 20(7):285-286.

Hynes, Michael J. et al., "Isolation of Genomic Clones Containing the *amdS Gene of Aspergillus nidulans* and Their Use in the Analysis of Structural and Regulatory Mutations," *Molecular and Cellular Biology*, 3(8):1430-1439, 1983.

Innis, M.A. et al., "Expression, Glycosylation, and Secretion of an *Aspergillus glucamylase* by *Saccharomyces cerevisiae*," *Science*, 228:21-26, 1985.

John, Marion A. et al., "Transformation of *Aspergillus nidulans* using the *argB* gene," *Enzyme Microb. Techno.*, 6:386-389, 1984.

Johnston should be Johnstone, I.L. et al., "Cloning an *Aspergillus nidulans* developmental gene by transformation," *EMBO Journal*, 4:1307-1311, 1985.

Kelly, Joan M. et al., "Transformation of *Aspergillus niger* by the *amdS* gene of *Aspergillus nidulans*," *The EMBO Journal*, vol. 4, No. 2, pp. 475-479, 1985.

Kennedy, Ann R., "The Bowman-Birk Inhibitor from Soybeans as an Anticarcinogenic Agent [1-3]," *Am. J. Clin. Nutr.* 68:1460S-1410S (1998).

Kinsey, John A. et al., "Transformation of *Neurospora crassa* with the Cloned *am* (Glutamate Dehydrogenase) Gene," *Molecular and Cellular Biology*, 4:117-122, 1984.

Lin et al., "The 0.25-nm X-ray structure of the Bowman-Birk-type inhibitor from mung bean in ternary complex with porcine trypsin," *Eur. J. Biochem.* (1993) 212:549-555.

Li et al., "The refolding purification, and activity analysis of a rice Bowman-Birk inhibitor expressed in *Escherichia coli*," *Protein Express. Purif.*, 15:99-104 (1999).

Lockington, Robin A. et al., "Cloning and characterization of the ethanol utilization regulon in *Aspergillus nidulans*," *Gene*, 33:137-149, 1985.

Marston, Fiona A.O., "The purification of eukaryotic polypeptides synthesized in *Escherichia coli*," *Biochem. J.*, 240:1-12, 1986.

McKnight, Gary L. et al., "Nucleotide Sequence of the Triosephosphate Isomerase Gene from *Aspergillus nidulans*: Implications for a Differential Loss of Introns," *Cell*, 46:143-147, 1986.

Mikosch et al., "Secretion of active human mucus proteinase inhibitor by Aspergillus niger after KEX2-like processing of a glucoamylase-inhibitor fusion protein," *J. Biotech.*, 52:97-106 (1996).

Mullaney, Edward J. et al., "Primary structure of the *trpC* gene from *Aspergillus nidulans*," *Mol. Gen. Genet.*, 199:37-45, 1985.

Mulligan and Berg, "Expression of a Bacterial Gene in Mammalian Cells," *Science*, 209 (4463) pp. 1422-1427, 1980.

Moralejo, et al., "A defined level of protein disulfide isomerase expression is required for optimal secretion of thaumatin by *Aspergillus awamori*," Moelcular *Genetics and Genomis*, 266(2):246-253 (2001).

Ngiam et al., "Characterization of a Foldase, Protein Disulfide Isomerase A, in the Protein Secretory Pathway of *Aspergillus niger*," *Applied and Environmental Microbiology*, 66(2):775-782 (2000).

Nunberg, Jack H. et al., "Molecular Cloning and Characterization of the Glucoamylase Gene of *Aspergillus awamori*," *Molecular and Cellular Biology*, pp. 2306-2315, Nov. 1984.

Pakula et al., "Monitoring the Kinetics of Glycoprotein Synthesis and Secretion in the Filamentous Fungus *Trichoderma reesei*: Cellobiohydrolase I (CBHI) as a Model Protein," *Microbiology*, 146:223-232 (2000).

Song et al., "Kunitz-type Soybean Trypin Inhibitor Revisited: Refined Structure of its Complex with Procine Trypsin Reveals an Insight into the Interaction Between a Homologous Inhibitor from Erythrina caffra and Tissue-type Plasminogen Activator," *J. Mol. Biol.* 275:347-63 (1998).

Southern and Berg, Transformatin of mammalian cells to antibiotic resistance with a bacterial gene under control of the SV40 region promoter, *J. Mol. Appl. Genet.*, 1982, V. 1(4), pp. 327-341.

Sugden et al., "A Vector that replicates as a Plasmid and can be efficiently selected in B-Lymphoblasts transformed by Epstein-Barr Virus," *Molecular and Cellular Biology*, V.5, N.2, pp. 410-413.

Te'Oet al., Codon optimization of xylanase gene xynB from the thermophilic bacterium dictyoglomus thermophilum for expression in the filamentous fungus Trichoderma reesei, *FEMS Microbiology Letters*, 190(1):13-19 (2000).

Tilburn, Joan et al., "Transformation by integration in *Aspergillus nidulans*," *Gene*, 26:205-221, 1983.

Van Hartingsvelt, W. et al., "Development of a homologous transformation system for *Aspergillus niger* based on the *pyrG* gene," *Mol. Gen. Genet.*, 206:71-75, 1987.

Voss et al., "Crystal structure of the bifunctional soybean Bowman-Birk inhibitor at 0.28-nm resolution. Structual peculiarities in a folded portein conformation," *Eur. J. Biochem.* (1996) 242(1):122-131).

Ward, Michael et al., "Use of *Aspergillus* overproducing mutants, cured for integrated plasmid, to overproduce heterologous proteins," *Appl. Microbiol. Biotechnol.*, vol. 39, pp. 738-743, 1993.

Werner & Wemmer, Identification of a protein-binding surface by differential amide- hydrogen-exchange, *J. Mol. Biol.*, Jun. 5, 1992, V.225(3), pp. 873-889.

Yelton, M. Melanie et al., "Transformation of *Aspergillus nidulans* by using a *trpC* plasmid," *Proc. Natl. Acad. Sci.*, vol. 81, pp. 1470-1474, Mar. 1984.

* cited by examiner

Codon optimized BBI (SEQ ID NO:1)

```
GCTAGCAACG TCATCTCCAA GCGCGACGAT GAGAGCTCTA AGCCCTGTTG    50
NheI
CGATCAGTGC GCGTGTACCA ATCGAACCC TCCGCAGTGT CGCTGCTCCG    100
ATATGCGTCT GAATTCCTGT CATAGCGCAT GCAAGAGCTG TATCTGCGCC    150
CTGAGCTACC CCGCGCAGTG TTTCTGCGTC GACATCACGG ACTTCTGCTA    200
CGAGCCGTGT AAGCCCAGCG AGGACGATAA GGAGAACTAG CTCGAGGGTG    250
                                           ***  XhoI  ####
ACC                                                       253

```

FIG. 1A

Codon optimized BBI with three glycine (SEQ ID NO:5)

```
GCTAGCAACG TCATCTCCAA GCGCGGCGGT GGCGACGATG AGAGCTCTAA    50
NheI
GCCCTGTTGC GATCAGTGCG CGTGTACCAA ATCGAACCCT CCGCAGTGTC    100
GCTGCTCCGA TATGCGTCTG AATTCCTGTC ATAGCGCATG CAAGAGCTGT    150
ATCTGCGCCC TGAGCTACCC CGCGCAGTGT TTCTGCGTCG ACATCACGGA    200
CTTCTGCTAC GAGCCGTGTA AGCCCAGCGA GGACGATAAG GAGAACTAGC    250
                                                   ***
TCGAGGGTGA CC                                             262
XhoI ##### ##
```

FIG. 1B

Codon optimized BBI with three glycine at N-terminal end and six histidine residues at C-terminal end (SEQ ID NO:54)

```
GCTAGCAACG TCATCTCCAA GCGCGGCGGT GGCGACGATG AGAGCTCTAA    50
NheI
GCCCTGTTGC GATCAGTGCG CGTGTACCAA ATCGAACCCT CCGCAGTGTC    100
GCTGCTCCGA TATGCGTCTG AATTCCTGTC ATAGCGCATG CAAGAGCTGT    150
ATCTGCGCCC TGAGCTACCC CGCGCAGTGT TTCTGCGTCG ACATCACGGA    200
CTTCTGCTAC GAGCCGTGTA AGCCCAGCGA GGACGATAAG GAGAACCACC    250
                                                   ····
ATCACCATCA CCACTAGCTC GAGGGTGACC                          280
··········  ·····***  XhoI #######
```

FIG. 1C

Codon Optimized STI (SEQ ID NO:3)

| | |
|---|---|
| GCTAGCAACG TCATCTCCAA GCGCGGCGGT GGCGATTTCG TGCTCGATAA<br>NheI | 50 |
| TGAAGGCAAC CCTCTTGAAA ATGGTGGCAC ATACTACATC CTGTCAGACA | 100 |
| TCACAGCATT TGGTGGAATC CGCGCAGCCC CTACGGGAAA TGAACGCTGC | 150 |
| CCTCTCACTG TGGTGCAATC TCGCAATGAG CTCGACAAAG GGATTGGAAC | 200 |
| AATCATCTCG TCCCCTTACC GAATCCGTTT TATCGCCGAA GGCCATCCTC | 250 |
| TGAGCCTTAA GTTCGATTCA TTTGCAGTTA TCATGCTGTG TGTTGGAATT | 300 |
| CCTACCGAGT GGTCTGTTGT GGAGGATCTA CCTGAAGGAC CTGCTGTTAA | 350 |
| AATTGGTGAG AACAAAGATG CAATGGATGG TTGGTTTCGC CTTGAGCGCG | 400 |
| TTTCTGATGA TGAATTCAAT AACTACAAGC TTGTGTTCTG TCCTCAGCAA | 450 |
| GCTGAGGATG ACAAATGTGG GGATATTGGG ATTAGTATTG ATCATGATGA | 500 |
| TGGAACCAGG CGTCTGGTGG TGTCTAAGAA CAAACCGCTG GTGGTTCAGT | 550 |
| TTCAAAAACT TGATAAAGAA TCACTGCACC ATCACCATCA CCACTAGCTC<br>..............***Xho | 600 |
| GAGGGTGACC<br>I ###### | 610 |

FIG. 2

BBI amino acid sequence (SEQ ID NO:7)

| | |
|---|---|
| DDESSKPCCD QCACTKSNPP QCRCSDMRLN SCHSACKSCI CALSYPAQCF | 50 |
| CVDITDFCYE PCKPSEDDKE N | 71 |

FIG. 3A

BBI with three glycine residues at N-terminal end (SEQ ID NO:8):

| | |
|---|---|
| GGGDDESSKP CCDQCACTKS NPPQCRCSDM RLNSCHSACK SCICALSYPA | 50 |
| QCFCVDITDF CYEPCKPSED DKEN | 74 |

FIG. 3B

BBI with three glycine residues at N-terminal end and six histidine residues at C-terminal end (SEQ ID NO:9):

| | |
|---|---|
| GGGDDESSKP CCDQCACTKS NPPQCRCSDM RLNSCHSACK SCICALSYPA | 50 |
| QCFCVDITDF CYEPCKPSED DKENHHHHHH | 80 |

FIG. 3C

STI amino acid sequence (with glycine & His tag) (SEQ ID NO:10)

| | | | | | |
|---|---|---|---|---|---|
| GGGDFVLDNE*** | GNPLENGGTY | YILSDITAFG | GIRAAPTGNE | RCPLTVVQSR | 50 |
| NELDKGIGTI | ISSPYRIRFI | AEGHPLSLKF | DSFAVIMLCV | GIPTEWSVVE | 100 |
| DLPEGPAVKI | GENKDAMDGW | FRLERVSDDE | FNNYKLVFCP | QQAEDDKCGD | 150 |
| IGISIDHDDG | TRRLVVSKNK | PLVVQFQKLD | KESLHHHHHH | | 190 |

FIG. 4A

STI amino acid sequence (without His tag) (SEQ ID NO:11)

| | | | | | |
|---|---|---|---|---|---|
| GGGDFVLDNE*** | GNPLENGGTY | YILSDITAFG | GIRAAPTGNE | RCPLTVVQSR | 50 |
| NELDKGIGTI | ISSPYRIRFI | AEGHPLSLKF | DSFAVIMLCV | GIPTEWSVVE | 100 |
| DLPEGPAVKI | GENKDAMDGW | FRLERVSDDE | FNNYKLVFCP | QQAEDDKCGD | 150 |
| IGISIDHDDG | TRRLVVSKNK | PLVVQFQKLD | KESL | | 184 |

FIG. 4B

STI amino acid sequence (SEQ ID NO:12)

| | | | | | |
|---|---|---|---|---|---|
| DFVLDNEGNP | LENGGTYYIL | SDITAFGGIR | AAPTGNERCP | LTVVQSRNEL | 50 |
| DKGIGTIISS | PYRIRFIAEG | HPLSLKFDSF | AVIMLCVGIP | TEWSVVEDLP | 100 |
| EGPAVKIGEN | KDAMDGWFRL | ERVSDDEFNN | YKLVFCPQQA | EDDKCGDIGI | 150 |
| SIDHDDGTRR | LVVSKNKPLV | QFQKLDKES | L | | 181 |

FIG. 4C

| | | |
|---|---|---|
| Wild-type | DDESSKPCCD QCACTKSNPP QCRCSDMRLN SCHSACKSCI CALSYPAQCF CVDITDFCYE PCKPSEDDKE N | (SEQ ID NO:7) |
| VEGF | DDESSKPCCD QCACYNLYGW TCRCSDMRLN SCHSACKSCI CALSYPAQCF CVDITDFCYE PCKPSEDDKE N | (SEQ ID NO:15) |
| VEGF | DDESSKPCCD QCACTKSNPP QCRCSDMRLN SCHSACKSCI CYNLYGWTCF CVDITDFCYE PCKPSEDDKE N | (SEQ ID NO:16) |
| VEGF | DDESSKPCCD QCACYNLYGW TCRCSDMRLN SCHSACKSCI CYNLYGWTCF CVDITDFCYE PCKPSEDDKE N | (SEQ ID NO:17) |
| C2 | DDESSKPCCD QCSCGRKIPI QCRCSDMRLN SCHSACKSCI CALSYPAQCF CVDITDFCYE PCKPSEDDKE N | (SEQ ID NO:18) |
| C3 | DDESSKPCCD QCGCARSNLD ECRCSDMRLN SCHSACKSCI CALSYPAQCF CVDITDFCYE PCKPSEDDKE N | (SEQ ID NO:19) |
| C4 | DDESSKPCCD QCGCQRALPI LCRCSDMRLN SCHSACKSCI CALSYPAQCF CVDITDFCYE PCKPSEDDKE N | (SEQ ID NO:20) |
| C5 | DDESSKPCCD QCQCGRLHMK TCRCSDMRLN SCHSACKSCI CALSYPAQCF CVDITDFCYE PCKPSEDDKE N | (SEQ ID NO:21) |
| Factor B | DDESSKPCCD QCQCKRKIVL DCRCSDMRLN SCHSACKSCI CALSYPAQCF CVDITDFCYE PCKPSEDDKE N | (SEQ ID NO:22) |
| MMP-2 | DDESSKPCCD QCACAAMFGP ACRCSDMRLN SCHSACKSCI CALSYPAQCF CVDITDFCYE PCKPSEDDKE N | (SEQ ID NO:23) |
| MMP-12 | DDESSKPCCD QCACGALGLF GCRCSDMRLN SCHSACKSCI CALSYPAQCF CVDITDFCYE PCKPSEDDKE N | (SEQ ID NO:24) |
| CBP1 | DDESSKPCCD QCACEPLIHQ RCRCSDMRLN SCHSACKSCI CALSYPAQCF CVDITDFCYE PCKPSEDDKE N | (SEQ ID NO:25) |
| CBP2 | DDESSKPCCD QCACSAFRGP TCRCSDMRLN SCHSACKSCI CALSYPAQCF CVDITDFCYE PCKPSEDDKE N | (SEQ ID NO:26) |
| C-statin | DDESSKPCCD QCACVVQDWG HHRCRCSDMR LNSCHSACKS CICALSYPAQ CFCVDITDFC YEPCKPSEDD KEN | (SEQ ID NO:27) |
| C-statin | DDESSKPCCD QCACTKSNPP QCRCSDMRLN SCHSACKSCI CVVQDWGHHR CFCVDITDFC YEPCKPSEDD KEN | (SEQ ID NO:28) |
| C-statin | DDESSKPCCD QCACVVQDWG HHRCRCSDMR LNSCHSACKS CVVQDWGHHR CFCVDITDFC YEPCKPSEDD KEN | (SEQ ID NO:29) |

| | | |
|---|---|---|
| VEGF | CYNLYGWTC | (SEQ ID NO:30) |
| C2 | CSCGRKIPIQC | (SEQ ID NO:31) |
| C3 | CGCARSNLDEC | (SEQ ID NO:32) |
| C4 | CGCQRALPILC | (SEQ ID NO:33) |
| C5 | CQCGRLHMKTC | (SEQ ID NO:34) |
| Factor B | CQCKRKIVLDC | (SEQ ID NO:35) |
| MMP-2 | CAAMFGPAC | (SEQ ID NO:36) |
| MMP-12 | CGALGLFGC | (SEQ ID NO:37) |
| cotton binding peptide | CEPLIHQRC | (SEQ ID NO:38) |
| cotton binding peptide | CSAFRGPTC | (SEQ ID NO:39) |
| Compstatin | CVVQDWGHHRC | (SEQ ID NO:40) |
| pTEX2

| | | | | | |
|---|---|---|---|---|---|
| AAGCTTAAGG | TGCACGGCCC | ACGTGGCCAC | TAGTACTTCT | CGAGCTCTGT | 50 |
| ACATGTCCGG | TCGCGACGTA | CGCGTATCGA | TGGCGCCAGC | TGCAGGCGGC | 100 |
| CGCCTGCAGC | CACTTGCAGT | CCCGTGGAAT | TCTCACGGTG | AATGTAGGCC | 150 |
| TTTTGTAGGG | TAGGAATTGT | CACTCAAGCA | CCCCCAACCT | CCATTACGCC | 200 |
| TCCCCCATAG | AGTTCCCAAT | CAGTGAGTCA | TGGCACTGTT | CTCAAATAGA | 250 |
| TTGGGGAGAA | GTTGACTTCC | GCCCAGAGCT | GAAGGTCGCA | CAACCGCATG | 300 |
| ATATAGGGTC | GGCAACGGCA | AAAAGCACG | TGGCTCACCG | AAAAGCAAGA | 350 |
| TGTTTGCGAT | CTAACATCCA | GGAACCTGGA | TACATCCATC | ATCACGCACG | 400 |
| ACCACTTTGA | TCTGCTGGTA | AACTCGTATT | CGCCCTAAAC | CGAAGTGCGT | 450 |
| GGTAAATCTA | CACGTGGGCC | CCTTTCGGTA | TACTGCGTGT | GTCTTCTCTA | 500 |
| GGTGCCATTC | TTTTCCCTTC | CTCTAGTGTT | GAATTGTTTG | TGTTGGAGTC | 550 |
| CGAGCTGTAA | CTACCTCTGA | ATCTCTGGAG | AATGGTGGAC | TAACGACTAC | 600 |
| CGTGCACCTG | CATCATGTAT | ATAATAGTGA | TCCTGAGAAG | GGGGGTTTGG | 650 |
| AGCAATGTGG | GACTTTGATG | GTCATCAAAC | AAAGAACGAA | GACGCCTCTT | 700 |
| TTGCAAAGTT | TTGTTTCGGC | TACGGTGAAG | AACTGGATAC | TTGTTGTGTC | 750 |
| TTCTGTGTAT | TTTTGTGGCA | ACAAGAGGCC | AGAGACAATC | TATTCAAACA | 800 |
| CCAAGCTTGC | TCTTTTGAGC | TACAAGAACC | TGTGGGTAT | ATATCTAGAG | 850 |
| TTGTGAAGTC | GGTAATCCCG | CTGTATAGTA | ATACGAGTCG | CATCTAAATA | 900 |
| CTCCGAAGCT | GCTGCGAACC | CGGAGAATCG | AGATGTGCTG | GAAAGCTTCT | 950 |
| AGCGAGCGGC | TAAATTAGCA | TGAAAGGCTA | TGAGAAATTC | TGGAGACGGC | 1000 |
| TTGTTGAATC | ATGGCGTTCC | ATTCTTCGAC | AAGCAAAGCG | TTCCGTCGCA | 1050 |
| GTAGCAGGCA | CTCATTCCCG | AAAAAACTCG | GAGATTCCTA | AGTAGCGATG | 1100 |
| GAACCGGAAT | AATATAATAG | GCAATACATT | GAGTTGCCTC | GACGGTTGCA | 1150 |
| ATGCAGGGGT | ACTGAGCTTG | GACATAACTG | TTCCGTACCC | CACCTCTTCT | 1200 |
| CAACCTTTGG | CGTTTCCCTG | ATTCAGCGTA | CCCGTACAAG | TCGTAATCAC | 1250 |
| TATTAACCCA | GACTGACCGG | ACGTGTTTTG | CCCTTCATTT | GGAGAAATAA | 1300 |
| TGTCATTGCG | ATGTGTAATT | TGCCTGCTTG | ACCGACTGGG | GCTGTTCGAA | 1350 |
| GCCCGAATGT | AGGATTGTTA | TCCGAACTCT | GCTCGTAGAG | GCATGTTGTG | 1400 |
| AATCTGTGTC | GGGCAGGACA | CGCCTCGAAG | GTTCACGGCA | AGGGAAACCA | 1450 |
| CCGATAGCAG | TGTCTAGTAG | CAACCTGTAA | AGCCGCAATG | CAGCATCACT | 1500 |
| GGAAAATACA | AACCAATGGC | TAAAAGTACA | TAAGTTAATG | CCTAAAGAAG | 1550 |
| TCATATACCA | GCGGCTAATA | ATTGTACAAT | CAAGTGGCTA | AACGTACCGT | 1600 |
| AATTTGCCAA | CGGCTTGTGG | GGTTGCAGAA | GCAACGGCAA | AGCCCCACTT | 1650 |
| CCCCACGTTT | GTTTCTTCAC | TCAGTCCAAT | CTCAGCTGGT | GATCCCCCAA | 1700 |
| TTGGGTCGCT | TGTTTGTTCC | GGTGAAGTGA | AAGAAGACAG | AGGTAAGAAT | 1750 |
| GTCTGACTCG | GAGCGTTTTG | CATACAACCA | AGGGCAGTGA | TGGAAGACAG | 1800 |
| TGAAATGTTG | ACATTCAAGG | AGTATTTAGC | CAGGGATGCT | TGAGTGTATC | 1850 |
| GTGTAAGGAG | GTTTGTCTGC | CGATACGACG | AATACTGTAT | AGTCACTTCT | 1900 |
| GATGAAGTGG | TCCATATTGA | AATGTAAGTC | GGCACTGAAC | AGGCAAAAGA | 1950 |
| TTGAGTTGAA | ACTGCCTAAG | ATCTCGGGCC | CTCGGGCCTT | CGGCCTTTGG | 2000 |
| GTGTACATGT | TTGTGCTCCG | GGCAAATGCA | AGTGTGGTA | GGATCGAACA | 2050 |
| CACTGCTGCC | TTTACCAAGC | AGCTGAGGGT | ATGTGATAGG | CAAATGTTCA | 2100 |
| GGGGCCACTG | CATGGTTTCG | AATAGAAAGA | GAAGCTTAGC | CAAGAACAAT | 2150 |
| AGCCGATAAA | GATAGCCTCA | TTAAACGGAA | TGAGCTAGTA | GGCAAAGTCA | 2200 |
| GCGAATGTGT | ATATATAAAG | GTTCGAGGTC | CGTGCCTCCC | TCATGCTCTC | 2250 |
| CCCATCTACT | CATCAACTCA | GATCCTCCAG | GAGACTTGTA | CACCATCTTT | 2300 |
| TGAGGCACAG | AAACCCAATA | GTCAACCGCG | GTTTAGGCGC | GCCAGCTCCG | 2350 |
| TGCGAAAGCC | TGACGCACCG | GTAGATTCTT | GGTGAGCCCG | TATCATGACG | 2400 |
| GCGGCGGGAG | CTACATGGCC | CCGGGTGATT | TATTTTTTTT | GTATCTACTT | 2450 |

FIG. 9A pTEX2

| | | | | | |
|---|---|---|---|---|---|
| CTGACCCTTT | TCAAATATAC | GGTCAACTCA | TCTTTCACTG | GAGATGCGGC | 2500 |
| CTGCTTGGTA | TTGCGATGTT | GTCAGCTTGG | CAAATTGTGG | CTTTCGAAAA | 2550 |
| CACAAAACGA | TTCCTTAGTA | GCCATGCATT | TTAAGATAAC | GGAATAGAAG | 2600 |
| AAAGAGGAAA | TTAAAAAAAA | AAAAAAAACA | AACATCCCGT | TCATAACCCG | 2650 |
| TAGAATCGCC | GCTCTTCGTG | TATCCCAGTA | CCAGTTTAAA | CGGATCTCAA | 2700 |
| GCTTGCATGC | AAAGATACAC | ATCAATCGCA | GCTGGGGTAC | AATCATCCAT | 2750 |
| CATCCCAACT | GGTACGTCAT | AACAAAAATC | GACAAGATGG | AAAAAGAGGT | 2800 |
| CGCCTAAATA | CAGCTGCATT | CTATGATGCC | GGGCTTTGGA | CAAGAGCTCT | 2850 |
| TTCTCAGCTC | CGTTTGTCCT | CCCTCCCTTT | TCCCCCTTCT | TGCTAAATGC | 2900 |
| CTTTCTTTAC | TTCTTTCTTC | CCTTCCCTCC | CTATCGCAG | CAGCCTCTCG | 2950 |
| GTGTAGGCTT | TCCACGCTGC | TGATCGGTAC | CGCTCTGCCT | CCTCTACGGG | 3000 |
| GTCTGAGGCC | TTGAGGATGC | CCCGGCCCAC | AATGGCAATG | TCGCTGCCGG | 3050 |
| CGATGCCAAT | CAGCTTGTGC | GGCGTGTTGT | ACTGCTGGCC | CTGGCCGTCT | 3100 |
| CCACCGACCG | ATCCGTTGGT | CTGCTGGTCC | TCGTCTTCGG | GGGGCAGCTG | 3150 |
| GCAGCCGGGC | GTCATGTGGA | TAAAGGCATC | GTCGGGCTCG | GTGTTGAGCG | 3200 |
| TCTCCTGCGA | GATGAAGCCC | ATGACAAAGT | CCTTGTGCTC | CCGGGCGGCC | 3250 |
| TCGACGCAGG | CCTGCGTGTA | CTCCTTGTTC | ATGAAGTTGC | CCTGGCTGGA | 3300 |
| CATTTGGGCG | AGGATCAGGA | GGCCTCGGCT | CAGCGGCGCC | TCCTCGATGC | 3350 |
| CCGGGAAGAG | CGACTCGTCG | CCCTCGGCGA | TGGCCTTTGT | TAACCGGGGC | 3400 |
| GAGGAGACGG | ACTCGTACTG | CTGGGTGACG | GTGGTGATGG | AGACGATGCT | 3450 |
| GCCCTTGCGG | CCGTCGCCGG | ACCGGTTCGA | GTAGATGGGC | TTGTCCAGGA | 3500 |
| CGCCAATGGA | GCCCATGCCG | TTGACGGCGC | CGGCGGGCTC | GGCGTCCCTG | 3550 |
| GAGTCGGCGT | CGTCGTCAAA | CGAGTCCATG | GTGGGCGTGC | CGACGGTGAC | 3600 |
| GGACGTCTTG | ACCTCGCAGG | GGTAGCGCTC | GAGCCAGCGC | TTGGCGCCCT | 3650 |
| GGGCCAGCGA | GGCCACCGAC | GCCTTGCCGG | GCACCATGTT | GACGTTGACA | 3700 |
| ATGTGCGCCC | AGTCGATGAT | GCGCGCCGAC | CCGCCCGTGT | ACTGCAGCTC | 3750 |
| GACGGTGTGG | CCAATGTCGC | CAAACTTGCG | GTCCTCGAAG | ATGAGGAAGC | 3800 |
| CGTGCTTGCG | CGCCAGCGAC | GCCAGCTGGG | CTCCCGTGCC | CGTCTCCGGG | 3850 |
| TGGAAGTCCC | AGCCCGAGAC | CATGTCGTAG | TGCGTCTTGA | GCACGACAAT | 3900 |
| CGACGGGCCA | ATCTTGTCGG | CCAGGTACAG | CAGCTCGCGC | GCTGTCGGCA | 3950 |
| CGTCGGCGCT | CAGGCACAGG | TTGGACGCCT | TGAGGTCCAT | GAGCTTGAAC | 4000 |
| AGGTAAGCCG | TCAGCGGGTG | CGTCGCCGTC | TCGCTCCTGG | CCGCGAAGGT | 4050 |
| GGCCTTGAGC | GTCGGGTGTG | GTGCCATGGC | TGATGAGGCT | GAGAGAGGCT | 4100 |
| GAGGCTGCGG | CTGGTTGGAT | AGTTTAACCC | TTAGGGTGCC | GTTGTGGCGG | 4150 |
| TTTAGAGGGG | GGGAAAAAAA | AGAGAGAGAT | GGCACAATTC | TGCTGTGCGA | 4200 |
| ATGACGTTGG | AAGCGCGACA | GCCGTGCGGG | AGGAAGAGGA | GTAGGAACTG | 4250 |
| TCGGCGATTG | GGAGAATTTC | GTGCGATCCG | AGTCGTCTCG | AGGCGAGGGA | 4300 |
| GTTGCTTTAA | TGTCGGGCTC | GTCCCTGGT | CAAAATTCTA | GGGAGCAGCG | 4350 |
| CTGGCAACGA | GAGCAGAGCA | GCAGTAGTCG | ATGCTAGAAA | TCGATAGATC | 4400 |
| CACGATGCCA | AAAAGCTTGT | TCATTTCGGC | TAGCCCGTGA | TCCTGGCGCT | 4450 |
| TCTAGGGCTG | AAACTGTGTT | GTTAATGTAT | TATTGGCTGT | GTAACTGACT | 4500 |
| TGAATGGGGA | ATGAGGAGCG | CGATGGATTC | GCTTGCATGT | CCCCTGGCCA | 4550 |
| AGACGAGCCG | CTTTGGCGGT | TTGTGATTCG | AAGGTGTGTC | AGCGGAGGCG | 4600 |
| CCAGGGCAAC | ACGCACTGAG | CCAGCCAACA | TGCATTGCTG | CCGACATGAA | 4650 |
| TAGACACGCG | CCGAGCAGAC | ATAGGAGACG | TGTTGACTGT | AAAAATTCTA | 4700 |
| CTGAATATTA | GCACGCATGG | TCTCAATAAG | AGCAATAGGA | ATGCTTGCCA | 4750 |
| ATCATAAGTA | CGTATGTGCT | TTTTCCTGCA | AATGGTACGT | ACGGACAGTT | 4800 |
| CATGTTGTCT | GTCATCCCCC | ACTCAGGCTC | TCATGATCAT | TTTATGGGAC | 4850 |
| TGGGGTTTTG | CTGACTGAAT | GGATTCAGCC | GCACGAAACA | AATTGGGGGC | 4900 |

FIG. 9B pTEX2

```
CATGCAGAAG GGAAGCCCCC CCAGCCCCCT GTTCATAATT TGTTAAGAGT    4950
CGGAGAGCTG CCTAGTATGA AGCAGCAATT GATAACGTTG ACTTTGCGCA    5000
TGAGCTCTGA AGCCGGGCAT ATGTATCACG TTTCTGCCTA GAGCCGCACG    5050
GGACCCAAGA AGCTCTTGTC ATAAGGTATT TATGAGTGTT CAGCTGCCAA    5100
CGCTGGTTCT ACTTTGGCTC AACCGCATCC CATAAGCTGA ACTTTGGGAG    5150
CTGCCAGAAT GTCTCTTGAT GTACAGCGAT CAACAACCGT GCGCCGGTCG    5200
ACAACTGTTC ACCGATCAGG GACGCGAAGA GGACCCAATC CCGGTTAACG    5250
CACCTGCTCC GAAGAAGCAA AAGGGCTATG AGGTGGTGCA GCAAGGAATC    5300
AAAGAGCTCT ATCCACTTGA CAAGGCCAAT GTCGCTCCCG ATCTGGAGTA    5350
AGTCAACCCT GAAGTGGAAG TTTGCTTCTC TGATTAGTAT GTAGCATCGT    5400
GTTTGTCCCA GGACTGGGTG CAAATCCCGA AGACAGCTGG AAGTCCAGCA    5450
AGACCGACTT CAATTGGACC ACGCATACAG ATGGCCTCCA GAGAGACTTC    5500
CCAAGAGCTC GGTTGCTTCT GTATATGTAC GACTCAGCAT GGACTGGCCA    5550
GCTCAAAGTA AACAATTCA TGGGCAATAT CGCGATGGGG CTCTTGGTTG    5600
GGCTGAGGAG CAAGAGAGAG GTAGGCCAAA CGCCAGACTC GAACCGCCAG    5650
CCAAGTCTCA AACTGACTGC AGGCGGCCGC CATATGCATC CTAGGCCTAT    5700
TAATATTCCG GAGTATACGT AGCCGGCTAA CGTTAACAAC CGGTACCTCT    5750
AGAACTATAG CTAGCATGCG CAAATTTAAA GCGCTGATAT CGATCGCGCG    5800
CAGATCCATA TATAGGGCCC GGGTTATAAT TACCTCAGGT CGACGTCCCA    5850
TGGCCATTCG AATTCGTAAT CATGGTCATA GCTGTTTCCT GTGTGAAATT    5900
GTTATCCGCT CACAATTCCA CACAACATAC GAGCCGGAAG CATAAAGTGT    5950
AAAGCCTGGG GTGCCTAATG AGTGAGCTAA CTCACATTAA TTGCGTTGCG    6000
CTCACTGCCC GCTTTCCAGT CGGGAAACCT GTCGTGCCAG CTGCATTAAT    6050
GAATCGGCCA ACGCGCGGGG AGAGGCGGTT TGCGTATTGG GCGCTCTTCC    6100
GCTTCCTCGC TCACTGACTC GCTGCGCTCG GTCGTTCGGC TGCGGCGAGC    6150
GGTATCAGCT CACTCAAAGG CGGTAATACG GTTATCCACA GAATCAGGGG    6200
ATAACGCAGG AAAGAACATG TGAGCAAAAG GCCAGCAAAA GGCCAGGAAC    6250
CGTAAAAAGG CCGCGTTGCT GGCGTTTTTC CATAGGCTCC GCCCCCCTGA    6300
CGAGCATCAC AAAAATCGAC GCTCAAGTCA GAGGTGGCGA AACCCGACAG    6350
GACTATAAAG ATACCAGGCG TTTCCCCCTG GAAGCTCCCT CGTGCGCTCT    6400
CCTGTTCCGA CCCTGCCGCT TACCGGATAC CTGTCCGCCT TTCTCCCTTC    6450
GGGAAGCGTG GCGCTTTCTC ATAGCTCACG CTGTAGGTAT CTCAGTTCGG    6500
TGTAGGTCGT TCGCTCCAAG CTGGGCTGTG TGCACGAACC CCCCGTTCAG    6550
CCCGACCGCT GCGCCTTATC CGGTAACTAT CGTCTTGAGT CCAACCCGGT    6600
AAGACACGAC TTATCGCCAC TGGCAGCAGC CACTGGTAAC AGGATTAGCA    6650
GAGCGAGGTA TGTAGGCGGT GCTACAGAGT TCTTGAAGTG GTGGCCTAAC    6700
TACGGCTACA CTAGAAGAAC AGTATTTGGT ATCTGCGCTC TGCTGAAGCC    6750
AGTTACCTTC GGAAAAAGAG TTGGTAGCTC TTGATCCGGC AAACAAACCA    6800
CCGCTGGTAG CGGTGGTTTT TTTGTTTGCA AGCAGCAGAT TACGCGCAGA    6850
AAAAAAGGAT CTCAAGAAGA TCCTTTGATC TTTTCTACGG GGTCTGACGC    6900
TCAGTGGAAC GAAAACTCAC GTTAAGGGAT TTTGGTCATG AGATTATCAA    6950
AAAGGATCTT CACCTAGATC CTTTTAAATT AAAAATGAAG TTTTAAATCA    7000
ATCTAAAGTA TATATGAGTA AACTTGGTCT GACAGTTACC AATGCTTAAT    7050
CAGTGAGGCA CCTATCTCAG CGATCTGTCT ATTTCGTTCA TCCATAGTTG    7100
CCTGACTCCC CGTCGTGTAG ATAACTACGA TACGGGAGGG CTTACCATCT    7150
GGCCCCAGTG CTGCAATGAT ACCGCGAGAC CCACGCTCAC CGGCTCCAGA    7200
TTTATCAGCA ATAAACCAGC CAGCCGGAAG GGCCGAGCGC AGAAGTGGTC    7250
CTGCAACTTT ATCCGCCTCC ATCCAGTCTA TTAATTGTTG CCGGGAAGCT    7300
AGAGTAAGTA GTTCGCCAGT TAATAGTTTG CGCAACGTTG TTGCCATTGC    7350
```

*FIG. 9C* pTEX2

```
TACAGGCATC GTGGTGTCAC GCTCGTCGTT TGGTATGGCT TCATTCAGCT    7400
CCGGTTCCCA ACGATCAAGG CGAGTTACAT GATCCCCCAT GTTGTGCAAA    7450
AAAGCGGTTA GCTCCTTCGG TCCTCCGATC GTTGTCAGAA GTAAGTTGGC    7500
CGCAGTGTTA TCACTCATGG TTATGGCAGC ACTGCATAAT TCTCTTACTG    7550
TCATGCCATC CGTAAGATGC TTTTCTGTGA CTGGTGAGTA CTCAACCAAG    7600
TCATTCTGAG AATAGTGTAT GCGGCGACCG AGTTGCTCTT GCCCGGCGTC    7650
AATACGGGAT AATACCGCGC CACATAGCAG AACTTTAAAA GTGCTCATCA    7700
TTGGAAAACG TTCTTCGGGG CGAAAACTCT CAAGGATCTT ACCGCTGTTG    7750
AGATCCAGTT CGATGTAACC CACTCGTGCA CCCAACTGAT CTTCAGCATC    7800
TTTTACTTTC ACCAGCGTTT CTGGGTGAGC AAAAACAGGA AGGCAAAATG    7850
CCGCAAAAAA GGGAATAAGG GCGACACGGA AATGTTGAAT ACTCATACTC    7900
TTCCTTTTTC AATATTATTG AAGCATTTAT CAGGGTTATT GTCTCATGAG    7950
CGGATACATA TTTGAATGTA TTTAGAAAAA TAAACAAATA GGGGTTCCGC    8000
GCACATTTCC CCGAAAAGTG CCACCTGACG TCTAAGAAAC CATTATTATC    8050
ATGACATTAA CCTATAAAAA TAGGCGTATC ACGAGGCCCT TTCGTCTCGC    8100
GCGTTTCGGT GATGACGGTG AAAACCTCTG ACACATGCAG CTCCCGGAGA    8150
CGGTCACAGC TTGTCTGTAA GCGGATGCCG GGAGCAGACA AGCCCGTCAG    8200
GGCGCGTCAG CGGGTGTTGG CGGGTGTCGG GCTGGCTTA ACTATGCGGC     8250
ATCAGAGCAG ATTGTACTGA GAGTGCACCA TAAAATTGTA AACGTTAATA    8300
TTTTGTTAAA ATTCGCGTTA AATTTTTGTT AAATCAGCTC ATTTTTTAAC    8350
CAATAGGCCG AAATCGGCAA AATCCCTTAT AAATCAAAAG AATAGCCCGA    8400
GATAGGGTTG AGTGTTGTTC CAGTTTGGAA CAAGAGTCCA CTATTAAAGA    8450
ACGTGGACTC CAACGTCAAA GGGCGAAAAA CCGTCTATCA GGGCGATGGC    8500
CCACTACGTG AACCATCACC CAAATCAAGT TTTTTGGGGT CGAGGTGCCG    8550
TAAAGCACTA AATCGGAACC CTAAAGGGAG CCCCCGATTT AGAGCTTGAC    8600
GGGGAAAGCC GGCGAACGTG GCGAGAAAGG AAGGGAAGAA AGCGAAAGGA    8650
GCGGGCGCTA GGGCGCTGGC AAGTGTAGCG GTCACGCTGC GCGTAACCAC    8700
CACACCCGCC GCGCTTAATG CGCCGCTACA GGGCGCGTAC TATGGTTGCT    8750
TTGACGTATG CGGTGTGAAA TACCGCACAG ATGCGTAAGG AGAAAATACC    8800
GCATCAGGCG CCATTCGCCA TTCAGGCTGC GCAACTGTTG GGAAGGGCGA    8850
TCGGTGCGGG CCTCTTCGCT ATTACGCCAG CTGGCGAAAG GGGGATGTGC    8900
TGCAAGGCGA TTAAGTTGGG TAACGCCAGG GTTTTCCCAG TCACGACGTT    8950
GTAAAACGAC GGCCAGTGCC                                    8970
```

FIG. 9D

EXPRESSION IN FILAMENTOUS FUNGI OF PROTEASE INHIBITORS AND VARIANTS THEREOF

This application is a Continuation Application of U.S. patent application Ser. No. 10/971,596, filed on Oct. 22, 2004 now U.S. Pat. No. 7,279,564, which claims priority to U.S. Provisional Application Ser. No. 60/518,154, filed on Nov. 6, 2003, both of which are incorporated by reference herein in their entirety.

FIELD OF THE INVENTION

This invention relates to methods for the expression of protease inhibitors and variants thereof in filamentous fungi. The invention discloses fusion nucleic acids, vectors, fusion polypeptides, and processes for obtaining the protease inhibitors.

BACKGROUND OF THE INVENTION

Proteases are involved in a wide variety of biological processes. Disruption of the balance between proteases and protease inhibitors is often associated with pathologic tissue destruction.

Various studies have focused on the role of proteinases in tissue injury, and it is thought that the balance between proteinases and proteinase inhibitors is a major determinant in maintaining tissue integrity. Serine proteinases from inflammatory cells, including neutrophils, are implicated in various inflammatory disorders, such as pulmonary emphysema, arthritis, atopic dermatitis and psoriasis.

Proteases also appear to function in the spread of certain cancers. Normal cells exist in contact with a complex protein network, called the extracellular matrix (ECM). The ECM is a barrier to cell movement and cancer cells must devise ways to break their attachments, degrade, and move through the ECM in order to metastasize. Proteases are enzymes that degrade other proteins and have long been thought to aid in freeing the tumor cells from their original location by chewing up the ECM. Recent studies have suggested that they may promote cell shape changes and motility through the activation of a protein in the tumor cell membrane called Protease-Activated Receptor-2 (PAR2). This leads to a cascade of intracellular reactions that activates the motility apparatus of the cell. Thus, it is hypothesized that one of the first steps in tumor metastasis is a reorganization of the cell shape such that it forms a distinct protrusion at one edge facing the direction of migration. The cell then migrates through a blood vessel wall and travels to distal locations, eventually reattaching and forming a metastatic tumor. For example, human prostatic epithelial cells constitutively secrete prostate-specific antigen (PSA), a kallikrein-like serine protease, which is a normal component of the seminal plasma. The protease acts to degrade the extracellular matrix and facilitate invasion of cancerous cells.

Synthetic and natural protease inhibitors have been shown to inhibit tumor promotion in vivo and in vitro. Previous research investigations have indicated that certain protease inhibitors belonging to a family of structurally-related proteins classified as serine protease inhibitors or SERPINS, are known to inhibit several proteases including trypsin, cathepsin G, thrombin, tissue kallikrein, as well as neutrophil elastase. The SERPINS are extremely effective at preventing/suppressing carcinogen-induced transformation in vitro and carcinogenesis in animal model systems. Systemic delivery of purified protease inhibitors reduces joint inflammation and cartilage and bone destruction as well.

Topical administration of protease inhibitors finds use in such conditions as atopic dermatitis, a common form of inflammation of the skin, which may be localized to a few patches or involve large portions of the body. The depigmenting activity of protease inhibitors and their capability to prevent ultraviolet-induced pigmentation have been demonstrated both in vitro and in vivo. Paine et al., *Journal of Investigative Dermatology* 116, 587-595 (2001). Also, protease inhibitors have been found to help wound healing (http://www.sciencedaily.com/releases/2000/10/001002071718.htm). Secretory leukocyte protease inhibitor was demonstrated to reverse the tissue destruction and speed the wound healing process when applied topically. In addition, serine protease inhibitors can also help to reduce pain in lupus erythematosus patients (See U.S. Pat. No. 6,537,968).

As noted above, protease inhibitors interfere with the action of proteases. Naturally occurring protease inhibitors can be found in a variety of foods such as cereal grains (oats, barley, and maize), Brussels sprouts, onion, beetroot, wheat, finger millet, and peanuts. One source of interest is the soybean. The average level in soybeans is around 1.4 percent and 0.6 percent for Kunitz and Bowman-Birk respectively, two of the most important protease inhibitors. These low levels make it impractical to isolate the natural protease inhibitor for clinical applications.

Thus, there is a need for a method to produce large quantities of protease inhibitors and their variants that also reduces or eliminates the risk associated with blood-borne infectious agents when these agents are produced in mammalian tissue culture cells. The inventive production method provided for herein allows for the manufacture of large quantities of the protein therapeutic.

BRIEF SUMMARY OF THE INVENTION

Provided herein are nucleic acids, cells and methods for the production of protease inhibitors and variants thereof.

In a first embodiment, nucleic acids encoding a functional protease inhibitor are provided. In one aspect, a nucleic acid comprising regulatory sequences operatively linked to a first, second, third and fourth nucleic acid sequences are provided. Terminator sequences are provided following the fourth nucleic acid sequence.

In a second aspect, the first nucleic acid sequence encodes a signal polypeptide functional as a secretory sequence in a first filamentous fungus, the second nucleic acid encodes a secreted polypeptide or functional portion thereof normally secreted from said first or a second filamentous fungus, the third nucleic acid encodes a cleavable linker and the fourth nucleic acid encodes a protease inhibitor or fragment thereof.

In a third aspect, an expression cassette comprising nucleic acid sequences encoding a protease inhibitor is provided.

In fourth aspect the present invention relates to a polynucleotide encoding a protease inhibitor variant. The polynucleotide may encode a Bowman-Birk Inhibitor variant wherein at least one loop has been altered. The polynucleotide may encode a Soybean Trypsin Inhibitor variant wherein at least one loop has been altered.

In a second embodiment, methods of expressing a functional protease inhibitor or variant thereof are provided. In one aspect, a host cell is (i) transformed with an expression cassette comprising a nucleic acid sequence encoding a protease inhibitor or variant thereof, and (ii) cultured under appropriate conditions to express the protease inhibitor or variants thereof. Optionally, the method further comprises recovering the protease inhibitor or variant thereof.

In a second aspect, a host cell is (i) transformed with an first expression cassette comprising a nucleic acid sequence encoding a protease inhibitor or variant thereof, (ii) transformed with a second expression cassette comprising a nucleic acid sequence encoding a chaperone, and (iii) cultured under appropriate conditions to express the protease inhibitors or variant thereof. Optionally, the protease inhibitors or variant thereof may be recovered. In one aspect, the protease inhibitors or variant thereof are expressed as a fusion protein. Optionally, the method further comprises recovering the protease inhibitor or variant thereof.

In a third embodiment, cells capable of expressing a protease inhibitor or variant thereof is provided. Host cells are transformed an expression cassette encoding a protease inhibitor or variant thereof. Host cells may be selected from the group consisting of *Aspergillus* and *Trichoderma*.

In a fourth embodiment, a functional protease inhibitor or variant thereof is provided. In one aspect, the functional protease inhibitor or variant thereof is expressed as a fusion protein consisting of the glucoamylase signal sequence, prosequence, catalytic domain and linker region up to amino acid number 502 of mature glucoamylase, followed by amino acids NVISKR and then by the mature protease inhibitor or variant thereof.

In a second aspect, the expressed proteins are treated with a protease to liberate a protease inhibitor or variant thereof from the fusion protein.

In a third aspect, the present invention provides a polypeptide having protease inhibitory activity, selected from the group consisting of
 a) Bowman-Birk Inhibitor variants;
 b) Soybean Trypsin Inhibitor variants;
 c) Bowman-Birk Inhibitor;
 d) Soybean Trypsin Inhibitor; and
 e) A scaffold comprising at least one variant sequence.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 1 is the codon optimized nucleotide sequence for soybean Bowman-Birk type protease inhibitor (BBI) (SEQ ID NO:1). This sequence includes nucleotides encoding NVISKR (dotted underline), the cleavage site for the fusion protein and three restriction enzyme sites for cloning into the expression plasmid. The NheI site at the 5' end and XhoI site at the 3' end are underlined and labeled. The BstEII site at the 3' end is designated by the # symbols. The stop codon is designated by the asterisks. There is no start codon as this is expressed as a fusion protein. The mature BBI coding sequence is indicated by the double underline (SEQ ID NO:2). The addition of nucleotides encoding three *glycine* (FIG. 1B) residues prior to the mature BBI coding sequence can be done using the sequence encoding the three *glycine* residues indicated in FIG. 2 (SEQ ID NO:5). FIG. 1C nucleotide sequence encoding BBI, the three restriction sites, the kex2 site, three *glycine* residues at the N-terminal end and six histidine residues at the C-terminal end is shown (SEQ ID NO:54).

FIG. 2 is the codon optimized nucleotide sequence for Soybean Trypsin Inhibitor (STI), a Kunitz type protease inhibitor (SEQ ID NO:3). This sequence includes nucleotides encoding NVISKR (dotted underline) (SEQ ID NO:4), the cleavage site for the fusion protein, and six histidine residues at the C-terminal end (indicated by the dots). Three restriction enzyme sites (NheI at 5' end and XhoI and BstEII at 3' end, indicated as described for FIG. 1) for cloning into the expression plasmid were also included. The three *glycine* residues after the kex2 site (NVISKR) are indicated by bold. The nucleotide sequence encoding the mature STI is indicated by the dashed underline (SEQ IN NO:6).

FIG. 3A is the mature amino acid sequence for BBI (SEQ ID NO:7). FIG. 3B is BBI with three *glycine* residues at N-terminal (SEQ ID NO:8). FIG. 3C is BBI with three *glycine* residues at N-terminal end and six histidine residues at C-terminal end (SEQ ID NO:9). In FIGS. 3A-C Loop1 is indicated by the underlined amino acid residues and Loop II amino acid residues are indicated by the bold type.

FIG. 4A is the mature STI with three *glycine* residues at the N-terminus and with six histidine residues at the C-terminus (SEQ ID NO: 10). FIG. 4B is STI with three *glycine* residues at the N-terminal end (SEQ ID NO:11). FIG. 4C is the mature amino acid sequence for STI (SEQ ID NO:12). Loop1 is indicated by the underlined amino acid residues (SEQ ID NO:13). Loop II amino acid residues are indicated by the bold type (SEQ ID NO:14).

FIG. 6 is the amino acid sequences for wild-type BBI (SEQ ID NO:7) and select variants of BBI (SEQ ID NOs:15 thru 29). The wild-type BBI has the loops underlined. The differences in the variants from the wild-type are shown as either bold/underlined (Loop I) or bold (LoopII). In some variants, e.g., C2, C3, C4, C5 and Factor B, alanine at position13 (between two cysteines) was also changed to either "Serine", "*Glycine*" or "Glutamine". Also, compstatin peptide has 9 amino acids instead of 7. The variant sequences are also shown (SEQ ID NOs:30 thru 40).

FIG. 9A-D is the nucleic acid sequence for pTrex2 (SEQ ID NO:41).

DETAILED DESCRIPTION

Figure 5:
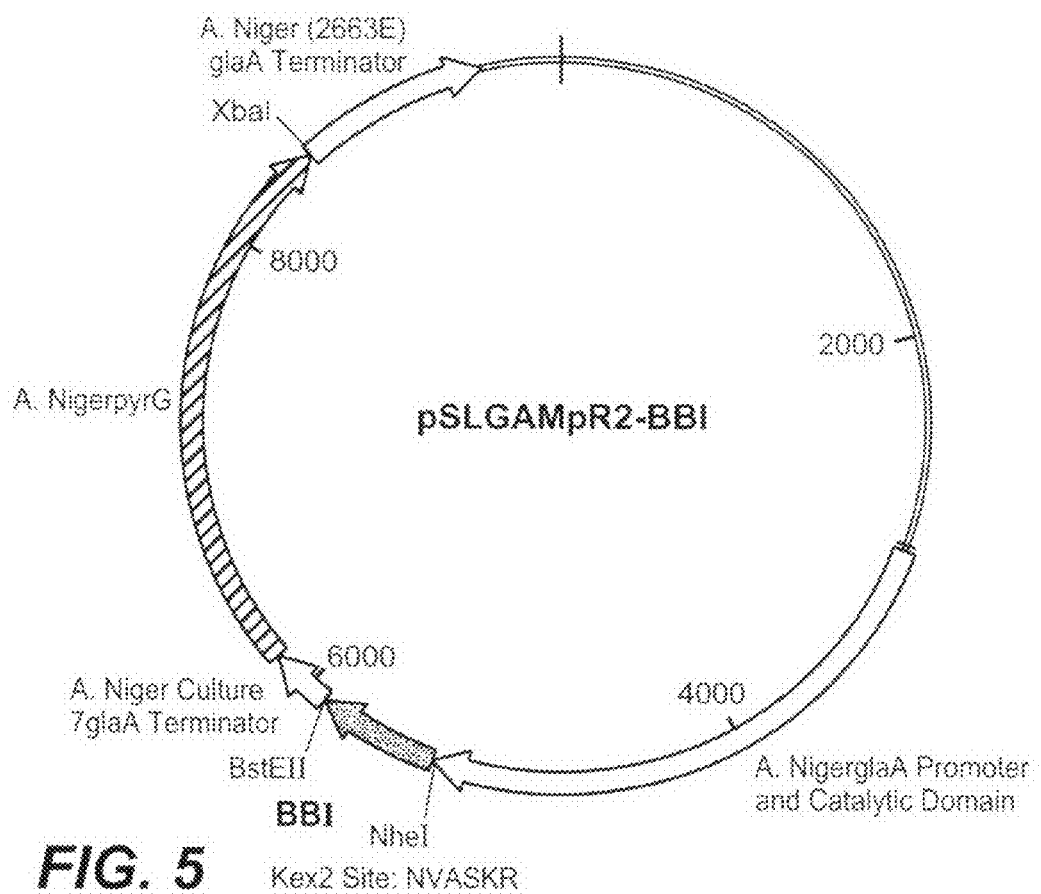
FIG. 5 is a diagram of the expression plasmid pSL-GAMpR2-BBI. This plasmid is based on pSLGAMpR2 which is derived from pSL1180 by inserting the *A. niger* glucoamylase promoter, catalytic core and terminator, a marker gene (*A. niger* pyrG) and a bovine prochymosin gene. The pSL1180 plasmid is available from Amersham Biosciences (Piscataway, N.J.). The pSLGAMpR2 plasmid has the elements listed above inserted in the same relative location as shown for pSLGAMpR2-BBI except that the bovine prochymosin gene is located where the BBI gene. Thus, the BBI gene replaces the prochymosin gene in pSLGAMpR2 to yield pSLGAMpR2-BBI.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

Definitions

An "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. Expression cassette may be used interchangeably with DNA construct and its grammatical equivalents.

As used herein, the term "vector" refers to a nucleic acid construct designed to transfer nucleic acid sequences into cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "plasmid" refers to a circular double-stranded (ds) DNA construct used as a cloning vector, and which forms an extrachromosomal self-replicating genetic element in some eukaryotes or integrates into the host chromosomes.

The term "nucleic acid molecule" or "nucleic acid sequence" includes RNA, DNA and cDNA molecules. It will be understood that, as a result of the degeneracy of the genetic code, a multitude of nucleotide sequences encoding a given protein may be produced.

As used herein, a "fusion DNA sequence" comprises from 5' to 3' a first, second, third and fourth DNA sequences.

As used herein, "a first nucleic acid sequence" or "first DNA sequence" encodes a signal peptide functional as a secretory sequence in a first filamentous fungus. Such signal sequences include those from glucoamylase, α-amylase and aspartyl proteases from *Aspergillus niger* var. *awamori*, *Aspergillus niger*, *Aspergillus oryzae*, signal sequences from cellobiohydrolase I, cellobiohydrolase II, endoglucanase I, endoglucanase III from *Trichoderma*, signal sequences from glucoamylase from *Neurospora* and *Humicola* as well as signal sequences from eukaryotes including the signal sequence from bovine chymosin, human tissue plasminogen activator, human interferon and synthetic consensus eukaryotic signal sequences such as that described by Gwynne et al. (1987) *Bio/Technology* 5, 713-719. Particularly preferred signal sequences are those derived from polypeptides secreted by the expression host used to express and secrete the fusion polypeptide. For example, the signal sequence from glucoamylase from *Aspergillus niger* is preferred when expressing and secreting a fusion polypeptide from *Aspergillus niger*. As used herein, first amino acid sequences correspond to secretory sequences which are functional in a filamentous fungus. Such amino acid sequences are encoded by first DNA sequences as defined.

As used herein, "second DNA sequences" encode "secreted polypeptides" normally expressed from filamentous fungi. Such secreted polypeptides include glucoamylase, α-amylase and aspartyl proteases from *Aspergillus niger* var. *awamori*, *Aspergillus niger*, and *Aspergillus oryzae*, cellobiohydrolase I, cellobiohydrolase II, endoglucanase I and endoglucanase III from *Trichoderma* and glucoamylase from *Neurospora* species and *Humicola* species. As with the first DNA sequences, preferred secreted polypeptides are those which are naturally secreted by the filamentous fungal expression host. Thus, for example when using *Aspergillus niger*, preferred secreted polypeptides are glucoamylase and α-amylase from *Aspergillus niger*, most preferably glucoamylase. In one aspect the glucoamylase is greater than 95%, 96%, 97%, 98% or 99% homologous with an *Aspergillus* glucoamylase.

When *Aspergillus* glucoamylase is the secreted polypeptide encoded by the second DNA sequence, the whole protein or a portion thereof may be used, optionally including a prosequence. Thus, the cleavable linker polypeptide may be fused to glucoamylase at any amino acid residue from position 468-509. Other amino acid residues may be the fusion site but utilizing the above residues is particularly advantageous.

A "functional portion of a secreted polypeptide" or grammatical equivalents means a truncated secreted polypeptide that retains its ability to fold into a normal, albeit truncated, configuration. For example, in the case of bovine chymosin production by *A. niger* var. *awamori* it has been shown that fusion of prochymosin following the 11th amino acid of mature glucoamylase provided no benefit compared to production of preprochymosin (U.S. Pat. No. 5,364,770). In U.S. Ser. No. 08/318,494, it was shown that fusion of prochymosin onto the C-terminus of preproglucoamylase up to the 297th amino acid of mature glucoamylase plus a repeat of amino acids 1-11 of mature glucoamylase yielded no secreted chymosin in *A. niger* var. *awamori*. In the latter case it is unlikely that the portion (approximately 63%) of the glucoamylase catalytic domain present in the fusion protein was able to fold correctly so that an aberrant, mis-folded and/or unstable fusion protein may have been produced which could not be secreted by the cell. The inability of the partial catalytic domain to fold correctly may have interfered with the folding of the attached chymosin. Thus, it is likely that sufficient residues of a domain of the naturally secreted polypeptide must be present to allow it to fold in its normal configuration independently of the desired polypeptide to which it is attached.

In most cases, the portion of the secreted polypeptide will be both correctly folded and result in increased secretion as compared to its absence.

Similarly, in most cases, the truncation of the secreted polypeptide means that the functional portion retains a biological function. In a preferred embodiment, the catalytic domain of a secreted polypeptide is used, although other functional domains may be used, for example, the substrate binding domains. In the case of *Aspergillus niger* and *Aspergillus niger* var. *awamori* glucoamylase, preferred functional portions retain the catalytic domain of the enzyme, and include amino acids 1-471. Additionally preferred embodiments utilize the catalytic domain and all or part of the linker region. Alternatively, the starch binding domain of glucoamylase may be used, which comprises amino acids 509-616 of *Aspergillus niger* and *Aspergillus niger* var. *awamori* glucoamylase.

As used herein, "third DNA sequences" comprise DNA sequences encoding a cleavable linker polypeptide. Such sequences include those which encode the prosequence of glucoamylase, the prosequence of bovine chymosin, the prosequence of subtilisin, prosequences of retroviral proteases including human immunodeficiency virus protease and DNA sequences encoding amino acid sequences recognized and cleaved by trypsin, factor $X_a$ collagenase, clostripin, subtilisin, chymosin, yeast KEX2 protease, *Aspergillus* KEXB and the like. See e.g. Marston, F. A. O. (1986) *Biol. Chem J.* 240, 1-12. Such third DNA sequences may also encode the amino acid methionine that may be selectively cleaved by cyanogen bromide. It should be understood that the third DNA sequence need only encode that amino acid sequence which is necessary to be recognized by a particular enzyme or chemical agent to bring about cleavage of the fusion polypeptide. Thus, the entire prosequence of, for example, glucoamylase, chymosin or subtilisin need not be used. Rather, only that portion of the prosequence which is necessary for recognition and cleavage by the appropriate enzyme is required.

It should be understood that the third nucleic acid need only encode that amino acid sequence which is necessary to be recognized by a particular enzyme or chemical agent to bring about cleavage of the fusion polypeptide.

Particularly preferred cleavable linkers are the KEX2 protease recognition site (Lys-Arg), which can be cleaved by a native *Aspergillus* KEX2-like (KEXB) protease, trypsin protease recognition sites of Lys and Arg, and the cleavage recognition site for endoproteinase-Lys-C.

As used herein, "fourth DNA sequences" encode "desired polypeptides." Such desired polypeptides include protease inhibitors and variants thereof.

The above-defined four DNA sequences encoding the corresponding four amino acid sequences are combined to form a "fusion DNA sequence." Such fusion DNA sequences are assembled in proper reading frame from the 5' terminus to 3' terminus in the order of first, second, third and fourth DNA sequences. As so assembled, the DNA sequence will encode a "fusion polypeptide" or "fusion protein" or "fusion analog" encoding from its amino-terminus a signal peptide functional as a secretory sequence in a filamentous fungus, a secreted polypeptide or portion thereof normally secreted from a filamentous fungus, a cleavable linker polypeptide and a desired polypeptide.

As used herein, the terms "desired protein" or "desired polypeptide" refers to a polypeptide or protein in its mature form that is not fused to a secretion enhancing construct. Thus, a "desired protein" or "desired polypeptide" refers to the protein to be expressed and secreted by the host cell in a non-fused form.

As used herein, a "fusion polypeptide" or "fusion protein" or "fusion analog" encodes from its amino-terminus a signal peptide functional as a secretory sequence functional in a host cell, a secreted polypeptide or portion thereof normally secreted from a host cell, a cleavable linker polypeptide and a desired polypeptide. The fusion protein may be processed by host cell enzymes, e.g., a protease, to yield the desired protein free from the other protein sequences in the fusion protein. As used herein, the terms "fusion analog" or "fusion polypeptide" or "fusion protein" may be used interchangeably.

As used herein, a "promoter sequence" is a DNA sequence which is recognized by the particular filamentous fungus for expression purposes. It is operably linked to a DNA sequence encoding the above defined fusion polypeptide. Such linkage comprises positioning of the promoter with respect to the translation initiation codon of the DNA sequence encoding the fusion DNA sequence. The promoter sequence contains transcription and translation control sequences which mediate the expression of the fusion DNA sequence. Examples include the promoter from the *A. niger* var. *awamori* or *A. niger* glucoamylase genes (Nunberg, J. H. et al. (1984) *Mol. Cell. Biol.* 4, 2306-2315; Boel, E. et al. (1984) *EMBO J.* 3, 1581-1585), the *A. oryzae, A. niger* var. *awamori* or *A. niger* or alpha-amylase genes, the *Rhizomucor miehei* carboxyl protease gene, the *Trichoderma reesei* cellobiohydrolase I gene (Shoemaker, S. P. et al. (1984) European Patent Application No. EPO0137280A1), the *A. nidulans* trpC gene (Yelton, M. et al. (1984) *Proc. Natl. Acad. Sci. USA* 81, 1470-1474; Mullaney, E. J. et al. (1985) *Mol. Gen. Genet.* 199, 37-45) the *A. nidulans* alcA gene (Lockington, R. A. et al. (1986) *Gene* 33 137-149), the *A. nidulans* amdS gene (McKnight, G. L. et al. (1986) *Cell* 46, 143-147), the *A. nidulans* amdS gene (Hynes, M. J. et al. (1983) *Mol. Cell Biol.* 3, 1430-1439), and higher eukaryotic promoters such as the SV40 early promoter (Barclay, S. L. and E. Meller (1983) *Molecular and Cellular Biology* 3, 2117-2130).

Likewise a "terminator sequence" is a DNA sequence which is recognized by the expression host to terminate transcription. It is operably linked to the 3' end of the fusion DNA encoding the fusion polypeptide to be expressed. Examples include the terminator from the *A. nidulans* trpC gene (Yelton, M. et al. (1984) *Proc. Natl. Acad. Sci. USA* 81, 1470-1474; Mullaney, E. J. et al. (1985) *Mol. Gen. Genet.* 199, 37-45), the *A. niger* var. *awamori* or *A. niger* glucoamylase genes (Nunberg, J. H. et al. (1984) *Mol. Cell. Biol.* 4, 2306-253; Boel, E. et al. (1984) *EMBO J.* 3, 1581-1585), the *A. oryzae, A. niger* var. *awamori* or *A. niger* or alpha-amylase genes and the *Rhizomucor miehei* carboxyl protease gene (EPO Publication No. 0 215 594), although any fungal terminator is likely to be functional in the present invention.

A "polyadenylation sequence" is a DNA sequence which when transcribed is recognized by the expression host to add polyadenosine residues to transcribed mRNA. It is operably linked to the 3' end of the fusion DNA encoding the fusion polypeptide to be expressed. Examples include polyadenylation sequences from the *A. nidulans* trpC gene (Yelton, M. et al. (1984) *Proc. Natl. Acad. Sci. USA* 81, 1470-1474; Mullaney, E. J. et al. (1985) *Mol. Gen. Genet.* 199, 37-45), the *A.* niger var. *awamori* or *A. niger* glucoamylase genes (Nunberg, J. H. et al. (1984) *Mol. Cell. Biol.* 4, 2306-2315) (Boel, E. et al. (1984) *EMBO J.* 3, 1581-1585), the *A. oryzae*, *A. niger* var. *awamori* or *A. niger* or alpha-amylase genes and the *Rhizomucor miehei* carboxyl protease gene described above. Any fungal polyadenylation sequence, however, is likely to be functional in the present invention.

As used herein, the term "selectable marker-encoding nucleotide sequence" refers to a nucleotide sequence which is capable of expression in fungal cells and where expression of the selectable marker confers to cells containing the expressed gene the ability to grow in the presence of a corresponding selective condition.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "expression" refers to the process by which a polypeptide is produced based on the nucleic acid sequence of a gene. The process includes both transcription and translation. It follows that the term "protease inhibitor expression" refers to transcription and translation of the specific protease inhibitors and variants thereof gene to be expressed, the products of which include precursor RNA, mRNA, polypeptide, post-translation processed polypeptide, and derivatives thereof. Similarly, "protease inhibitor expression" refers to the transcription, translation and assembly of protease inhibitors and variants thereof into a form exemplified by FIG. 6. By way of example, assays for protease inhibitor expression include examination of fungal colonies when exposed to the appropriate conditions, western blot for protease inhibitor protein, as well as northern blot analysis and reverse transcriptase polymerase chain reaction (RT-PCR) assays for protease inhibitor mRNA.

As used herein the term "glycosylated" means that oligosaccharide molecules have been added to particular amino acid residues on a protein. A "de-glycosylated" protein is a protein that has been treated to partially or completely remove the oligosaccharide molecules from the protein. An "aglycosylated" protein is a protein that has not had the oligosaccharide molecules added to the protein. This may be due to a mutation in the protein that prevents the addition of the oligosaccharide.

A "non-glycosylated" protein is a protein that does not have the oligosaccharide attached to the protein. This may be due to various reasons, including but not limited to, the absence of enzymes responsible for the addition of the oligosaccharides to proteins. The term "non-glycosylated" encompasses both proteins that have not had the oligosaccharide added to the protein and those in which the oligosaccharides have been added but were subsequently removed. An "aglycosylated" protein may be a "non-glycosylated" protein. A "non-glycosylated" protein may be either an "aglycosylated" protein or a "deglycosylated" protein.

The terms "isolated" or "purified" as used herein refer to a nucleic acid or polypeptide that is removed from at least one component with which it is naturally associated The term "substantially free" includes preparations of the desired polypeptide having less than about 20% (by dry weight) other proteins (i.e., contaminating protein), less than about 10% other proteins, less than about 5% other proteins, or less than about 1% other proteins.

The term "substantially pure" when applied to the proteins or fragments thereof of the present invention means that the proteins are essentially free of other substances to an extent practical and appropriate for their intended use. In particular, the proteins are sufficiently pure and are sufficiently free from other biological constituents of the host cells so as to be useful in, for example, protein sequencing, or producing pharmaceutical preparations.

The term "target protein" as used herein refers to protein, e.g., an enzyme, hormone or the like, whose action would be blocked by the binding of the variant inhibitors provided for herein.

The terms "variant sequence" or "variant sequences" refer to the short polypeptide sequence(s) that replace the binding loops of the wild-type protease inhibitor or other scaffold. The variant sequence does not need to be of the same length as the binding loop sequence it is replacing in the scaffold.

The term "scaffold" refers to the wild-type protein sequence into which a variant sequence may be introduced. In an embodiment the scaffold will have portions, e.g., loops, that may be replaced. For example, the STI and BBI sequences used herein would be a scaffold for a variant sequence.

Protease Inhibitors

Two protein protease inhibitors have been isolated from soybeans, the Kunitz-type trypsin inhibitor (soybean trypsin inhibitor, STI) and the Bowman-Birk protease inhibitor (BBI). See, e.g., Birk, Int. J. Pept. Protein Res. 25:113-131 (1985) and Kennedy, Am. J. Clin. Neutr. 68:1406S-1412S (1998). These inhibitors serve as a scaffold for the variant sequences.

In addition, to alterations in the scaffold comprising the variant sequences, other desired proteins used herein include the addition of three *glycine* residues at the N-terminal and/or six histidine residues at the C-terminal. See FIGS. 3 and 4.

Soybean Trypsin Inhibitor (STI)

STI inhibits the proteolytic activity of trypsin by the formation of a stable stoichiometric complex. See, e.g., Liu, K., Chemistry and Nutritional value of soybean components. In: Soybeans, chemistry, technology and utilization. pp. 32-35 (Aspen publishers, Inc., Gaithersburg, Md., 1999). STI consists of 181 amino acid residues with two disulfide bridges and is roughly spherically shaped. See, e.g., Song et al., J. Mol. Biol. 275:347-63 (1998). The two disulfide bridges form two binding loops similar to those described below for BBI.

The Kunitz-type soybean trypsin inhibitor (STI) has played a key role in the early study of proteinases, having been used as the main substrate in the biochemical and kinetic work that led to the definition of the standard mechanism of action of proteinase inhibitors.

Bowman-Birk Inhibitor (BBI)

BBI proteins are a kinetically and structurally well-characterized family of small proteins (60-90 residues) isolated from leguminous seeds. They have a symmetrical structure of two tricyclic domains each containing an independent binding loop. Loop I typically inhibits trypsin and loop II chymotrypsin (Chen et al., J. Biol. Chem. (1992) 267:1990-1994; Werner & Wemmer, 1992; Lin et al., Eur. J. Biochem. (1993) 212:549-555; Voss et al., Eur. J. Biochem. (1996) 242:122-131). These binding regions each contain a "canonical loop" structure, which is a motif found in a variety of serine proteinase inhibitors (Bode & Huber, Eur. J. Biochem. (1992) 204:433-451).

BBI is an 8 k-Da protein that inhibits the proteases trypsin and chymotrypsin at separate reactive sites. See, e.g., Billings et al., Pro. Natl. Acad. Sci. 89:3120-3124 (1992). STI and BBI are found only in the soybean seed, and not in any other part of the plant. See, e.g., Birk, Int. J. Pept. Protein Res. 25:113-131 (1985).

Although numerous isoforms of BBI have been characterized, SEQ ID NO: 7 (FIG. 3) shows the amino acid sequence of the BBI backbone used herein comprising approximately 71 amino acid residues. In addition, BBI may become truncated with as many as 10 amino acid residues being removed from either the N- or C-terminal. For example, upon seed desiccation, a BBI may have the C-terminal 9 or 10 amino acid residues removed. Thus, proteolysis is highly tolerated prior to the initial disulphide and just after the terminal disulphide bond, the consequences of which are usually not detrimental to the binding to target protein. However, it will be appreciated that any one of the isoforms or truncated forms could be used.

Protease Inhibitor Variants

As noted above, the STI and BBI protease inhibitors have binding loops that inhibit proteases. The inventive protease inhibitor variants provided for herein have alterations in Loop I, Loop II or both loops. In an embodiment, the loops are replaced with sequences that interact with a target protein.

The loops can be replaced with sequences derived from VEGF binding proteins, inhibitors of the complement pathway such as C2, C3, C4 or C5 inhibitors, cotton binding proteins, Compstatin and the like. Alternatively, variant sequences can be selected by various methods known in the art such as, for example, phage display or other screening method. For example, a random peptide gene library is fused with phage PIII gene so the peptide library will be displayed on the surface of the phage. Subsequently, the phage display library is exposed to the target protein and washed with buffer to remove non-specific binding (this process is sometimes referred to as panning). Finally, the binding phage and PCR the DNA sequence for the peptide encoded are isolated.

Generally, a loop will be replaced with a variant sequence, i.e., peptides, 3 to 14 amino acids in length, 5 to 10 amino acids being preferred. Longer sequences may be used as long as they provide the binding and/or inhibition desired. In addition, peptides suitable for use as replacements of the binding loop(s) should adopt a functional conformation when contained within a constrained loop, i.e., a loop formed by the presence to a disulfide bond between two cysteine residues. In specific embodiments, the peptides are between 7 and 9 amino acids in length. These replacement sequences also provide protease inhibition or binding to the targeted proteins.

In some cases it may be advantages to alter a single amino acid. Specifically, the Alanine at residue 13 of wild-type STI or BBI may be changed to a Serine, a *Glycine* or a Glutamine.

Fusion Proteins

Each protease inhibitor and variant thereof will be expressed as a fusion protein by the host fungal cell. Although cleavage of the fusion polypeptide to release the desired protein will often be useful, it is not necessary. Protease inhibitors and variants thereof expressed and secreted as fusion proteins surprisingly retain their function.

The above-defined four DNA sequences encoding the corresponding four amino acid sequences are combined to form a "fusion DNA sequence." Such fusion DNA sequences are assembled in proper reading frame from the 5' terminus to 3' terminus in the order of first, second, third and fourth DNA sequences. As so assembled, the DNA sequence will encode a "fusion polypeptide" encoding from its amino-terminus a signal peptide functional as a secretory sequence in a filamentous fungus, a secreted polypeptide or portion thereof normally secreted from a filamentous fungus, a cleavable linker peptide and a desired polypeptide, e.g., a protease inhibitor and variants thereof.

Production of fusion proteins can be accomplished by use of the methods disclosed in, for example, U.S. Pat. Nos. 5,411,873, 5,429,950, and 5,679,543. Other methods are well known in the art.

Expression of Recombinant a Protease Inhibitor

To the extent that this invention depends on the production of fusion proteins, it relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology* (1994).

This invention provides filamentous fungal host cells which have been transduced, transformed or transfected with an expression vector comprising a protease inhibitor-encoding nucleic acid sequence. The culture conditions, such as temperature, pH and the like, are those previously used for the parental host cell prior to transduction, transformation or transfection and will be apparent to those skilled in the art.

Basically, a nucleotide sequence encoding a fusion protein is operably linked to a promoter sequence functional in the host cell. This promoter-gene unit is then typically cloned into intermediate vectors before transformation into the host cells for replication and/or expression. These intermediate vectors are typically prokaryotic vectors, e.g., plasmids, or shuttle vectors.

In one approach, a filamentous fungal cell line is transfected with an expression vector having a promoter or biologically active promoter fragment or one or more (e.g., a series) of enhancers which functions in the host cell line, operably linked to a nucleic acid sequence encoding a protease inhibitor, such that the a protease is expressed in the cell line. In a preferred embodiment, the DNA sequences encode a protease inhibitor or variant thereof. In another preferred embodiment, the promoter is a regulatable one.

A. Codon Optimization

Optimizing codon usage in genes that express well with those genes that do not express well is known in the art. See Barnett et al., GB2200118 and Bergquist et al., Extremophiles (2002) 6:177-184. Codon optimization, as used herein, was based on comparing heterologous proteins that are expressed well in *Aspergillus* and native secreted proteins to the heterologous proteins that are not expressed well. See Table I.

TABLE I

| Proteins that expressed well | Proteins that did not express well |
|---|---|
| glucoamylase | Human DPPIV |
| alpha-amylase | NEP |
| stachybotrys laccase A | |
| stachybotrys laccase B | |
| human trypsin | |
| SCCE | |
| bovine prochymosin | |
| Her2 antibodies light chain | |

Selected codons that were not used or not used often in the expressed proteins will be changed to codons that were used often. Therefore, we only changed a subset of codons.

B. Nucleic Acid Constructs/Expression Vectors.

Natural or synthetic polynucleotide fragments encoding a protease inhibitor ("PI-encoding nucleic acid sequences") may be incorporated into heterologous nucleic acid constructs or vectors, capable of introduction into, and replication in, a filamentous fungal cell. The vectors and methods disclosed herein are suitable for use in host cells for the expression of a protease inhibitor and variants thereof. Any vector may be used as long as it is replicable and viable in the cells into which it is introduced. Large numbers of suitable vectors and promoters are known to those of skill in the art, and are commercially available. Appropriate cloning and expression vectors for use in filamentous fungal cells are also described in Sambrook et al., 1989, and Ausubel F M et al., 1989, expressly incorporated by reference herein. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Appropriate vectors are typically equipped with a selectable marker-encoding nucleic acid sequence, insertion sites, and suitable control elements, such as termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionein promoter that can upregulated by addition of certain metal salts. In one embodiment of this invention, glaA promoter is used. This promoter is induced in the presence of maltose. Such promoters are well known to those of skill in the art.

Those skilled in the art are aware that a natural promoter can be modified by replacement, substitution, addition or elimination of one or more nucleotides without changing its function. The practice of the invention encompasses and is not constrained by such alterations to the promoter.

The choice of promoter used in the genetic construct is within the knowledge of one skilled in the art.

The choice of the proper selectable marker will depend on the host cell, and appropriate markers for different hosts are well known in the art. Typical selectable marker genes encode proteins that (a) confer resistance to antibiotics or other toxins, for example, ampicillin, methotrexate, tetracycline, neomycin (Southern and Berg, J., 1982), mycophenolic acid (Mulligan and Berg, 1980), puromycin, zeomycin, or hygromycin (Sugden et al., 1985) or (b) compliment an auxotrophic mutation or a naturally occurring nutritional deficiency in the host strain. In a preferred embodiment, a fungal pyrG gene is used as a selectable marker (Ballance, D. J. et al., 1983, Biochem. Biophys. Res. Commun. 112:284-289). In another preferred embodiment, a fungal amdS gene is used as a selectable marker (Tilburn, J. et al., 1983, Gene 26:205-221).

A selected PI coding sequence may be inserted into a suitable vector according to well-known recombinant techniques and used to transform a cell line capable of PI expression. Due to the inherent degeneracy of the genetic code, other nucleic acid sequences which encode substantially the same or a functionally equivalent amino acid sequence may be used to clone and express a specific protease inhibitor, as further detailed above. Therefore it is appreciated that such substitutions in the coding region fall within the sequence variants covered by the present invention. Any and all of these sequence variants can be utilized in the same way as described herein for a parent PI-encoding nucleic acid sequence. One skilled in the art will recognize that differing PIs will be encoded by differing nucleic acid sequences.

Once the desired form of a protease inhibitor nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

Heterologous nucleic acid constructs may include the coding sequence for an protease inhibitor, or a variant, fragment or splice variant thereof: (i) in isolation; (ii) in combination with additional coding sequences; such as fusion protein or signal peptide coding sequences, where the PI coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the PI coding sequence is a heterologous gene.

A heterologous nucleic acid containing the appropriate nucleic acid coding sequence, as described above, together with appropriate promoter and control sequences, may be employed to transform filamentous fungal cells to permit the cells to express a protease inhibitor or variant thereof.

In one aspect of the present invention, a heterologous nucleic acid construct is employed to transfer a PI-encoding nucleic acid sequence into a cell in vitro, with established cell lines preferred. Preferably, cell lines that are to be used as production hosts have the nucleic acid sequences of this invention stably integrated. It follows that any method effective to generate stable transformants may be used in practicing the invention.

In one aspect of the present invention, the first and second expression cassettes may be present on a single vector or on separate vectors.

The practice of the present invention will employ, unless otherwise indicated, conventional techniques of molecular biology, microbiology, and recombinant DNA, which are within the skill of the art. Such techniques are explained fully in the literature. See, for example, "Molecular Cloning: A Laboratory Manual", Second Edition (Sambrook, Fritsch & Maniatis, 1989), "Animal Cell Culture" (R. I. Freshney, ed., 1987); and "Current Protocols in Molecular Biology" (F. M. Ausubel et al., eds., 1987). All patents, patent applications, articles and publications mentioned herein, both supra and infra, are hereby expressly incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes, also within the knowledge of one skilled in the art.

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that are typically included in expression vectors also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable.

C. Host Cells and Culture Conditions.

The present invention provides cell lines comprising cells which have been modified, selected and cultured in a manner effective to result in expression of a protease inhibitor and variants thereof.

Examples of parental cell lines which may be treated and/or modified for PI expression include, but are not limited to, filamentous fungal cells. Examples of appropriate primary cell types for use in practicing the invention include, but are not limited to, *Aspergillus* and *Trichoderma*.

Protease inhibitor expressing cells are cultured under conditions typically employed to culture the parental cell line. Generally, cells are cultured in a standard medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of protease inhibitor expression are achieved.

Preferred culture conditions for a given cell line may be found in the scientific literature and/or from the source of the cell line such as the American Type Culture Collection (ATCC; "http://www.atcc.org/"). Typically, after cell growth has been established, the cells are exposed to conditions effective to cause or inhibit the expression of a protease inhibitor and variants thereof.

In the preferred embodiments, where a PI coding sequence is under the control of an inducible promoter, the inducing agent, e.g., a carbohydrate, metal salt or antibiotics, is added to the medium at a concentration effective to induce protease inhibitor expression.

D. Introduction of a Protease Inhibitor-Encoding Nucleic Acid Sequence into Host Cells.

The methods of transformation used may result in the stable integration of all or part of the transformation vector into the genome of the filamentous fungus. However, transformation resulting in the maintenance of a self-replicating extra-chromosomal transformation vector is also contemplated.

The invention further provides cells and cell compositions which have been genetically modified to comprise an exogenously provided PI-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above. In a preferred embodiment, a plasmid is used to transfect a filamentous fungal cell. The transformations may be sequential or by co-transformation.

Various methods may be employed for delivering an expression vector into cells in vitro. Methods of introducing nucleic acids into cells for expression of heterologous nucleic acid sequences are also known to the ordinarily skilled artisan, including, but not limited to electroporation; nuclear microinjection or direct microinjection into single cells; protoplast fusion with intact cells; use of polycations, e.g., polybrene or polyornithine; or PEG. membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; *Agrobacterium*-mediated transfer of DNA; and the like. In addition, heterologous nucleic acid constructs comprising a PI-encoding nucleic acid sequence can be transcribed in vitro, and the resulting RNA introduced into the host cell by well-known methods, e.g., by injection.

Following introduction of a heterologous nucleic acid construct comprising the coding sequence for a protease inhibitor, the genetically modified cells can be cultured in conventional nutrient media modified as appropriate for activating promoters, selecting transformants or amplifying expression of a PI-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the PI-encoding nucleic acid sequence found in the heterologous nucleic acid construct.

E. Fungal Expression

Appropriate host cells include filamentous fungal cells. The "filamentous fungi" of the present invention, which serve both as the expression hosts and the source of the first and second nucleic acids, are eukaryotic microorganisms and include all filamentous forms of the subdivision Eumycotina, Alexopoulos, C. J. (1962), Introductory Mycology, New York: Wiley. These fungi are characterized by a vegetative mycelium with a cell wall composed of chitin, glucans, and other complex polysaccharides. The filamentous fungi of the present invention are morphologically, physiologically, and genetically distinct from yeasts. Vegetative growth by filamentous fungi is by hyphal elongation. In contrast, vegetative growth by yeasts such as *S. cerevisiae* is by budding of a unicellular thallus. Illustrations of differences between *S. cerevisiae* and filamentous fungi include the inability of *S. cerevisiae* to process *Aspergillus* and *Trichoderma* introns and the inability to recognize many transcriptional regulators of filamentous fungi (Innis, M. A. et al. (1985) Science, 228, 21-26).

Various species of filamentous fungi may be used as expression hosts including the following genera: *Aspergillus, Trichoderma, Neurospora, Penicillium, Cephalosporium, Achlya, Phanerochaete, Podospora, Endothia, Mucor, Fusarium, Humicola,* and *Chrysosporium.* Specific expression hosts include *A. nidulans,* (Yelton, M., et al. (1984) Proc. Natl. Acad. Sci. USA, 81, 1470-1474; Mullaney, E. J. et al. (1985) Mol. Gen. Genet. 199, 37-45; John, M. A. and J. F. Peberdy (1984) Enzyme Microb. Technol. 6, 386-389; Tilburn, et al. (1982) Gene 26, 205-221; Ballance, D. J. et al., (1983) Biochem. Biophys. Res. Comm. 112, 284-289; Johnston, I. L. et al. (1985) EMBO J. 4, 1307-1311) *A. niger,* (Kelly, J. M. and M. Hynes (1985) EMBO 4, 475-479) *A. niger* var. *awamori,* e.g., NRRL 3112, ATCC 22342, ATCC 44733, ATCC 14331 and strain UVK 143f, *A. oryzae,* e.g., ATCC 11490, *N. crassa* (Case, M. E. et al. (1979) Proc. Natl. Acad. Sci. USA 76, 5259-5263; Lambowitz U.S. Pat. No. 4,486,553; Kinsey, J. A. and J. A. Rambosek (1984) *Molecular and Cellular Biology* 4, 117-122; Bull, J. H. and J. C. Wooton (1984) Nature 310, 701-704), *Trichoderma reesei,* e.g. NRRL 15709, ATCC 13631, 56764, 56765, 56466, 56767, and *Trichoderma viride,* e.g., ATCC 32098 and 32086. A preferred expression host is *A. niger* var. *awamori* in which the gene encoding the major secreted aspartyl protease has been deleted. The production of this preferred expression host is described in U.S. patent application Ser. No. 214,237 filed Jul. 1, 1988, expressly incorporated herein by reference.

During the secretion process in fungi, which are eukaryotes, the secreted protein crosses the membrane from the cytoplasm into the lumen of the endoplasmic reticulum (ER). It is here that the protein folds and disulphide bonds are formed. Chaperone proteins such as BiP and proteins like protein disulphide isomerase assist in this process. It is also at this stage where sugar chains are attached to the protein to produce a glycosylated protein. Sugars are typically added to asparagine residues as N-linked glycosylation or to serine or threonine residues as O-linked glycosylation. Correctly folded and glycosylated proteins pass from the ER to the Golgi apparatus where the sugar chains are modified and where the KEX2 or KEXB protease of yeast and fungi resides. The N-linked glycosylation added to secreted proteins produced in fungi differs from that added by mammalian cells.

Protease inhibitor and variants thereof produced by the filamentous fungal host cells may be either glycosylated or non-glycosylated (i.e., aglycosylated or deglycosylated). Because the fungal glycosylation pattern differs from that produced by mammalian cells, the protease inhibitor may be treated with an enzyme to deglycosylate the protease inhibitor Enzymes useful for such N-linked deglycosylation are endoglycosidase H, endoglycosidase F1, endoglycosidase F2, endoglycosidase A, PNGase F, PNGase A, and PNGase At. Enzymes useful for such O-linked deglycosylation are exoglycosidases, specifically alpha-mannosidases (e.g. alpha-Mannosidase (*Aspergillus saito,* iGKX-5009), alpha (1-2,3,6)-Mannosidase (Jack bean, GKX-5010) alpha-Mannosidase/MANase VI (recombinant from *Xanthomonas manihoti,* GKX80070) all from Glyko (Prozyme), San Leandro, Calif.).

We have surprisingly found that high levels of a protease inhibitor and variants thereof can be made in fungi when fused to a native secreted protein. From the information provided above it is clear that the protease inhibitor and variants thereof would be expected to assemble in the ER when glucoamylase was still attached to the N-termini. This would produce a large protein of greater than 56 kD. The glucoamylase would not be expected to be cleaved from the desired protein when it passed through the Golgi apparatus without further modification.

Using the present inventive methods and host cells, we have attained surprising levels of expression. The system utilized herein has achieved levels of expression and secretion of greater than 0.5 g/l of protease inhibitor.

After the expression vector is introduced into the cells, the transfected cells are cultured under conditions favoring expression of gene encoding the desired protein. Large batches of transformed cells can be cultured as described above. Finally, product is recovered from the culture using techniques known in the art.

Chaperones

As noted above, the folding and glycosylation of the secretory proteins in the ER is assisted by numerous ER-resident proteins called chaperones. The chaperones like Bip (GRP78), GRP94 or yeast Lhs1p help the secretory protein to fold by binding to exposed hydrophobic regions in the unfolded states and preventing unfavourable interactions (Blond-Elguindi et al., 1993, *Cell* 75:717-728). The chaperones are also important for the translocation of the proteins through the ER membrane. The foldase proteins like protein disulphide isomerase (pdi) and its homologs and prolyl-peptidyl cis-trans isomerase assist in formation of disulphide bridges and formation of the right conformation of the peptide chain adjacent to proline residues, respectively.

In one aspect of the invention the host cells are transformed with an expression vector encoding a chaperone. The chaperone is selected from the group consisting of pdiA and prpA.

Fermentation Parameters

The invention relies on fermentation procedures for culturing fungi. Fermentation procedures for production of heterologous proteins are known per se in the art. For example, proteins can be produced either by solid or submerged culture, including batch, fed-batch and continuous-flow processes.

Culturing is accomplished in a growth medium comprising an aqueous mineral salts medium, organic growth factors, the carbon and energy source material, molecular oxygen, and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth, since the assimilation of the substrate and corresponding growth of the microorganisms, is, in part, a combustion process.

Although the aeration rate can vary over a considerable range, aeration generally is conducted at a rate which is in the range of about 0.5 to 10, preferably about 0.5 to 7, volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time this is balanced by the fact that high atmospheric pressures do increase equipment and operating costs.

The fermentation temperature can vary somewhat, but for filamentous fungi such as *Aspergillus niger* var. *awamori* the temperature generally will be within the range of about 20° C. to 40° C., generally preferably in the range of about 28° C. to 37° C., depending on the strain of microorganism chosen.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Aspergillus niger* var. *awamori*, the pH normally is within the range of about 4.5 to 5.5. pH range preferences for certain microorganisms are dependent on the media employed to some extent, as well as the particular microorganism, and thus change somewhat with change in media as can be readily determined by those skilled in the art.

While the average retention time of the fermentation admixture in the fermentor can vary considerably, depending in part on the fermentation temperature and culture employed, generally it will be within the range of about 24 to 500 hours, preferably presently about 24 to 400 hours.

Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps.

As described above, the time to reach this limiting substrate level is not critical and may vary with the particular microorganism and fermentation process being conducted. However, it is well known in the art how to determine the carbon source concentration in the fermentation medium and whether or not the desired level of carbon source has been achieved.

Although the fermentation can be conducted as a batch or continuous operation, fed batch operation is generally preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium to the fermentor.

Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible, but more importantly to obtain the highest production of the desired protein per unit volume.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though presently preferred is operation under 15L Biolafitte (Saint-Germain-en-Laye, France).

Protein Separations

Once the desired protein is expressed and, optionally, secreted recovery of the desired protein may be necessary. The present invention provides methods of separating a desired protein from its fusion analog. It is specifically contemplated that the methods described herein are useful for the separation of proteinase inhibitor and variants from the fusion analog.

The collection and purification of the desired protein from the fermentation broth can also be done by procedures known per se in the art. The fermentation broth will generally contain cellular debris, including cells, various suspended solids and other biomass contaminants, as well as the desired protein product, which are preferably removed from the fermentation broth by means known in the art.

Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate prior to crystallization using techniques such as ultrafiltration, evaporation or precipitation.

Precipitating the proteinaceous components of the supernatant or filtrate may be accomplished by means of a salt, e.g., ammonium sulfate or adjust pH to 2 to 3 and then heat treatment of the broth at 80° C. for 2 hours, followed by purification by a variety of chromatographic procedures, e.g., ion exchange chromatography, affinity chromatography or similar art recognized procedures.

When the expressed desired polypeptide is secreted the polypeptide may be purified from the growth media. Preferably the expression host cells are removed from the media before purification of the polypeptide (e.g. by centrifugation).

When the expressed recombinant desired polypeptide is not secreted from the host cell, the host cell is preferably disrupted and the polypeptide released into an aqueous "extract" which is the first stage of purification. Preferably the expression host cells are collected from the media before the cell disruption (e.g. by centrifugation).

The cell disruption may be performed by conventional techniques such as by lysozyme or beta-glucanase digestion or by forcing the cells through high pressure. See (Robert K. Scobes, Protein Purification, Second edition, Springer-Verlag) for further description of such cell disruption techniques.

The addition of six histidine residues, i.e., a His Tag, to the C-terminus may also aid in the purification of the desired protein and its fusion analog. Use of the His tag as a purification aid is well known in the art. See, for example, Hengen (1995) TIBS 20(7):285-286. The 6× his-tagged proteins are easily purified using Immobilized Metal ion Affinity Chromatography (IMAC).

It is specifically contemplated that protease inhibitors and variants thereof may be purified from an aqueous protein solution, e.g., whole cell fermentation broth or clarified broth, using a combination of hydrophobic charge induction chromatography (HCIC). HCIC provided an ability to separate the desired protein from the broth and from its fusion analog.

Utility

For some applications of desired proteins it is of high importance that the protease inhibitors are extremely pure, e.g. having a purity of more than 99%. This is particularly true whenever the desired protein is to be used as a therapeutic, but is also necessary for other applications. The methods described herein provide a way of producing substantially pure desired proteins. The desired proteins described herein are useful in pharmaceutical and personal care compositions.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds); Ci (Curies) mCi (milliCuries); µCi (microCuries); TLC (thin layer achromatography); Ts (tosyl); Bn (benzyl); Ph (phenyl); Ms (mesyl); Et (ethyl), Me (methyl). PI (proteinase inhibitor), BBI (Bowman-Birk inhibitor), STI (Soybean Trypsin inhibitor).

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Cloning of DNA Encoding the Soybean Trypsin Inhibitor

This example illustrates the development of an expression vector for STI.

In general, the gene encoding the desired protein was fused to the DNA encoding the linker region of glucoamylase with an engineered kexB cleavage site (NVISKR) via an NheI restriction enzyme site at the N-terminal and a BstEII restriction enzyme site at the C-terminal following the STI stop codon, TAG. The gene encoding the soybean STI was synthesized by MCLAB (South San Francisco, Calif.) in vitro as a DNA fragment containing two restriction sites, a kexB cleavage site and three *glycine* residues at N-terminal end and six histidine residues at C-terminal end. (SEQ ID NO:3, gene shown in FIG. 2). All PCR-generated DNA fragments used herein were initially cloned into the pCRII-TOPO vector (Invitrogen, Carlsbad, Calif.). *E. coli* [One Shot® TOP10 cells from Invitrogen], was used for routine plasmid isolation and plasmid maintenance. The NheI and BstEII sites were used to excise the PCR product from the pCRII-TOPO vector, and the resulting DNA fragment was then ligated into the expression vector, pSL1180-GAMpR-2 (see FIG. 5) The expression vector, pSL1180-GAMpR2, contains the *Aspergillus niger* glucoamylase promoter, the glucoamylase catalytic domain and the terminator region. The expression plasmid also contains the *A. niger* pyrG gene as the selection marker. Thus, detection of transformants with the expression cassette is by growth on uridine-deficient medium.

The gene encoding the STI peptide (for amino acid sequence: FIG. 4A, SEQ ID NO:10; for nucleotide sequence: FIG. 2 and SEQ ID NO:6) was synthesized and cloned into pCRII-TOPO vector (Invitrogen) by MCLAB. The NheI to BstEII fragment was release from the plasmid by restriction digestion and the DNA fragment was extracted from an agarose gel and cloned into pSLGAMpR2, a glucoamylase-chymosin expression vector which is described in detail in WO 9831821. to create expression plasmid pSLGAMpR2-SBTI/nonopti (Q110).

The expression plasmid was transformed into dgr246ΔGAP:pyr2-. This strain is derived from strain dgr246 P2 which has the pepA gene deleted, is pyrG minus and has undergone several rounds of mutagenesis and screening or selection for improved production of a heterologous gene product (Ward, M. et al., 1993, Appl. Microbiol. Biotech. 39:738-743 and references therein). To create strain dgr246ΔGAP:pyr2- the glaA (glucoamylase) gene was deleted in strain dgr246 P2 using exactly the same deletion plasmid (pΔGAM NB-Pyr) and procedure as reported by Fowler, T. et al (1990) Curr. Genet. 18:537-545. Briefly, the deletion was achieved by transformation with a linear DNA fragment having glaA flanking sequences at either end and with part of the promoter and coding region of the glaA gene replaced by the *Aspergillus nidulans* pyrG gene as selectable marker. Transformants in which the linear fragment containing the glaA flanking sequences and the pyrG gene had integrated at the chromosomal glaA locus were identified by Southern blot analysis. This change had occurred in transformed strain dgr246ΔGAP. Spores from this transformant were plated onto medium containing fluoroorotic acid and spontaneous resistant mutants were obtained as described by van Hartingsveldt, W. et al. (1987) Mol. Gen. Genet. 206:71-75. One of these, dgr246ΔGAP:pyr2-, was shown to be a uridine auxotroph strain which could be complemented by transformation with plasmids bearing a wild-type pyrG gene.

The *Aspergillus* transformation protocol was a modification of the Campbell method (Campbell et at. (1989). Curr. Genet. 16:53-56). All solutions and media were either autoclaved or filter sterilized through a 0.2 micron filter. Spores of *A. niger* var. *awamori* were harvested from complex media agar (CMA) plates. CMA contained 20 g/l dextrose, 20 g/l Difco Brand malt extract, 1 g/l Bacto Peptone, 20 g/l Bacto agar, 20 ml/l of 100 mg/ml arginine and 20 ml/l of 100 mg/ml uridine. An agar plug of approximately 1.5 cm square of spores was used to inoculate 100 mls of liquid CMA (recipe as for CMA except that the Bacto agar was omitted). The flask was incubated at 37° C. on a shaker at 250-275 rpm, overnight. The mycelia were harvested through sterile Miracloth (Calbiochem, San Diego, Calif., USA) and washed with 50 mls of Solution A (0.8M $MgSO_4$ in 10 mM sodium phosphate, pH 5.8). The washed mycelia were placed in a sterile solution of 300 mg of beta-D-glucanase (Interspex Products, San Mateo, Calif.) in 20 mls of solution A. This was incubated at 28° to 30° C. at 200 rpm for 2 hour in a sterile 250 ml plastic bottle (Corning Inc, Corning, N.Y.). After incubation, this protoplasting solution was filtered through sterile Miracloth into a sterile 50 ml conical tube (Sarstedt, USA). The resulting liquid containing protoplasts was divided equally amongst two 50 ml conical tubes. Forty ml of solution B (1.2 M sorbitol, 50 mM $CaCl_2$, 10 mM Tris, pH 7.5) were added to each tube and centrifuged in a table top clinical centrifuge (Damon IEC HN SII centrifuge) at full speed for 5 minutes. The supernatant from each tube was discarded and 20 mls of fresh solution B was added to one tube, mixed, then poured into the next tube until all the pellets were resuspended. The tube was then centrifuged for 5 minutes. The supernatant was discarded, 20 mls of fresh solution B was added, the tube was centrifuged for 5 minutes. The wash occurred one last time before resuspending the washed protoplasts in solution B at a density of $0.5$-$1.0 \times 10^7$ protoplasts/100 ul. To each 100 ul of protoplasts in a sterile 15 ml conical tube (Sarstedt, USA), 10 ul of the transforming plasmid DNA was added. To this, 12.5 ul of solution C (50% PEG 4000, 50 mM $CaCl_2$, 10 mM Tris, pH 7.5) was added and the tube was placed on ice for 20 minutes. One ml of solution C was added and the tube was removed from the ice to room temperature and shaken gently. Two ml of solution B was added immediately to dilute solution C. The transforming mix was added equally to 3 tubes of melted MMS overlay (6 g/l $NaNO_3$, 0.52 g/l KCl, 1.52 g/l $KH_2PO_4$, 218.5 g/l D-sorbitol, 1.0 ml/l trace elements-LW, 10 g/l SeaPlaque agarose (FMC Bioproducts, Rook1and, Maine, USA) 20 ml/l 50% glucose, 2.5 ml/l 20% $MgSO_4.7H_2O$, pH to 6.5 with NaOH) that were stored in a 45° C. water bath. Trace elements-LW consisted of 1 g/l $FeSO_4.7H_2O$, 8.8 g/l $ZnSO_4.7H_2O$, 0.4 g/l $CuSO_4.5H_2O$, 0.15 g/l $MnSO_4.4H_2O$, 0.1 g $Na_2B_4O_7.10H_2O$, 50 mg/l $(NH_4)_6Mo_7O_{24}.4H_2O$, 250 mls H2O, 200 ul/l concentrated HCl.

The melted overlays with the transformation mix were immediately poured onto 3 MMS plates (same as MMS overlay recipe with the exception of 20 g/l of Bacto agar instead of 10 g/l of SeaPlaque agarose) that had been supplemented with 333 ul/plate of 100 mg/ml of arginine added directly on top of the agar plate. After the agarose solidified, the plates were incubated at 30° C. until transformants grew.

The sporulating transformants were picked off with a sterile toothpick onto a plate of minimal media+glucose (MM). MM consisted of 6 g/l $NaNO_3$, 0.52 g/l KCl, 1.52 g/l $KH_2PO_4$, 1 ml/l Trace elements-LW, 20 g/l Bacto agar, pH to 6.5 with NaOH, 25 ml/l of 40% glucose, 2.5 ml/l of 20% $MgSO_4.7H_2O$ and 20 ml/l of 100 mg/ml arginine. Once the transformants grew on MM they were transferred to CMA plates.

A 1.5 cm square agar plug from a plate culture of each transformant was added to 50 mls, in a 250 ml shake flask, of production medium called Promosoy special. This medium had the following components: 70 g/l sodium citrate, 15 g/l $(NH_4)_2 SO_4$, 1 g/l $NaH_2PO_4.H_2O$, 1 g/l $MgSO_4$, 1 ml Tween 80, pH to 6.2 with NaOH, 2 ml/l Mazu DF60-P, 45 g/l Promosoy 100 (Central Soya, Fort Wayne, Ind.), 120 g/l maltose. The production media flasks were incubated at 30° C., 200 rpm for 5 days and supernatant samples were harvested. Transformants were assayed for protein production on SDS gel to select the transformants based on the amount of protein produced. Broth from the top transformants were assayed for Trypsin or chymotrypsin inhibition activity A 1.5 cm square agar plug from a plate culture of each transformant was also added to 50 mls, in a 250 ml shake flask, of production medium called modified CSS. This medium had the following components: 50 g/l Corn Streep Solids, 1 g/l NaH2PO4*H2O, 0.5 g/l MgSO4 (anhydrous), 50 g/l Staley 7350 (55%) and 8 g/l Na Citrate. The production media flasks were incubated at 36° C., 200 rpm for 3 days and supernatant samples were harvested and assayed for protein production on SDS gel. Broth from the top transformants were assayed for Trypsin or Chymotrypsin inhibition activity.

Example 2

Codon Optimization of the DNA Encoding the Soybean Trypsin Inhibitor

The following example details how the STI-encoding DNA was altered for optimized expression in a filamentous fungi.

The codons from the synthetic gene (the starting material in Example 1 that was synthesized by MCLAB) were then optimized according to the codon usage of highly expressed proteins in *Aspergillus*. Basically, proteins that expressed well such as glucoamylase, alpha-amylase and prochymosin were compared to proteins that did not express well in *Aspergillus* such as human NEP and DPP4. See Table I. The codon usage table for both types of protein expressions in *Aspergillus* is in Table II.

TABLE II

| Codon | AA | NEP coding | DPP4 | SCCE | bovine prochymosin | chymotrypsin | Her2 Light chain | Stachybotrys oxidase B | stachybotrys oxidase A | glucoamylase w/out starch binding domain |
|---|---|---|---|---|---|---|---|---|---|---|
| gca * | Ala(A) | 19 | 15 | 1 | 0 | 1 | 1 | 2 | 4 | 10 |
| gcc | Ala(A) | 12 | 6 | 8 | 15 | 17 | 8 | 19 | 23 | 18 |
| gcg | Ala(A) | 1 | 2 | 0 | 1 | 1 | 2 | 1 | 0 | 9 |
| gcu | Ala(A) | 18 | 12 | 2 | 1 | 3 | 3 | 25 | 21 | 20 |

TABLE II-continued

| Codon | AA | NEP coding | DPP4 | SCCE | bovine prochymosin | chymotrypsin | Her2 Light chain | Stachybotrys oxidase B | stachybotrys oxidase A | glucoamylase w/out starch binding domain |
|---|---|---|---|---|---|---|---|---|---|---|
| --- | Ala(A) | 50 | 35 | 11 | 17 | 22 | 14 | 47 | 48 | 57 |
| aga * | Arg(R) | 15 | 16 | 3 | 1 | 0 | 2 | 2 | 2 | 1 |
| agg | Arg(R) | 5 | 8 | 4 | 6 | 4 | 1 | 4 | 5 | 1 |
| cga | Arg(R) | 6 | 1 | 0 | 1 | 0 | 0 | 7 | 3 | 3 |
| cgc | Arg(R) | 2 | 1 | 4 | 1 | 1 | 2 | 12 | 11 | 6 |
| cgg | Arg(R) | 1 | 3 | 0 | 0 | 0 | 0 | 0 | 0 | 2 |
| cgu | Arg(R) | 4 | 1 | 0 | 0 | 1 | 4 | 7 | 8 | 4 |
| --- | Arg(R) | 33 | 30 | 11 | 9 | 6 | 9 | 32 | 29 | 17 |
| aac | Asn(N) | 20 | 16 | 1 | 11 | 6 | 5 | 26 | 27 | 17 |
| aau * | Asn(N) | 36 | 23 | 9 | 4 | 3 | 1 | 5 | 6 | 6 |
| --- | Asn(N) | 56 | 39 | 10 | 15 | 9 | 6 | 31 | 33 | 23 |
| gac | Asp(D) | 13 | 16 | 10 | 20 | 14 | 5 | 24 | 20 | 17 |
| gau * | Asp(D) | 28 | 27 | 4 | 2 | 1 | 5 | 18 | 19 | 18 |
| --- | Asp(D) | 41 | 43 | 14 | 22 | 15 | 10 | 42 | 39 | 35 |
| ugc | Cys(C) | 7 | 4 | 10 | 3 | 8 | 4 | 1 | 0 | 6 |
| ugu | Cys(C) | 5 | 8 | 2 | 3 | 2 | 1 | 0 | 1 | 2 |
| --- | Cys(C) | 12 | 12 | 12 | 6 | 10 | 5 | 1 | 1 | 8 |
| caa * | Gln(Q) | 14 | 15 | 3 | 1 | 1 | 3 | 2 | 6 | 4 |
| cag | Gln(Q) | 17 | 15 | 7 | 24 | 8 | 12 | 14 | 13 | 11 |
| --- | Gln(Q) | 31 | 30 | 10 | 25 | 9 | 15 | 16 | 19 | 15 |
| gaa * | Glu(E) | 36 | 31 | 4 | 2 | 1 | 1 | 2 | 4 | 7 |
| gag | Glu(E) | 17 | 9 | 2 | 12 | 5 | 8 | 38 | 42 | 11 |
| --- | Glu(E) | 53 | 40 | 6 | 14 | 6 | 9 | 40 | 46 | 18 |
| gga * | Gly(G) | 15 | 20 | 5 | 1 | 1 | 2 | 10 | 10 | 5 |
| ggc | Gly(G) | 12 | 7 | 11 | 15 | 14 | 5 | 17 | 20 | 20 |
| ggg | Gly(G) | 7 | 6 | 1 | 12 | 7 | 0 | 0 | 1 | 4 |
| ggu | Gly(G) | 7 | 7 | 4 | 3 | 1 | 4 | 17 | 11 | 12 |
| --- | Gly(G) | 41 | 40 | 21 | 31 | 23 | 11 | 44 | 42 | 41 |
| cac | His(H) | 5 | 8 | 5 | 4 | 3 | 2 | 11 | 13 | 4 |
| cau | His(H) | 4 | 11 | 2 | 2 | 0 | 1 | 2 | 4 | 0 |
| --- | His(H) | 9 | 19 | 7 | 6 | 3 | 3 | 13 | 17 | 4 |
| aua | Ile(I) | 9 | 13 | 1 | 1 | 1 | 0 | 0 | 0 | 0 |
| auc | Ile(I) | 10 | 12 | 3 | 19 | 9 | 5 | 19 | 16 | 8 |
| auu * | Ile(I) | 26 | 22 | 2 | 2 | 2 | 1 | 6 | 12 | 11 |
| --- | Ile(I) | 45 | 47 | 6 | 22 | 12 | 6 | 25 | 28 | 19 |
| cua * | Leu(L) | 5 | 6 | 0 | 0 | 0 | 0 | 0 | 0 | 2 |
| cuc | Leu(L) | 7 | 8 | 8 | 5 | 4 | 3 | 13 | 18 | 16 |
| cug | Leu(L) | 9 | 15 | 10 | 23 | 15 | 10 | 14 | 16 | 15 |
| cuu | Leu(L) | 15 | 7 | 0 | 1 | 0 | 0 | 11 | 12 | 3 |
| uua * | Leu(L) | 7 | 10 | 1 | 0 | 0 | 0 | 0 | 0 | 0 |
| uug * | Leu(L) | 16 | 9 | 1 | 0 | 0 | 1 | 5 | 3 | 6 |
| --- | Leu(L) | 59 | 55 | 20 | 29 | 19 | 14 | 43 | 49 | 42 |
| aaa * | Lys(K) | 32 | 27 | 3 | 6 | 1 | 5 | 0 | 0 | 0 |
| aag | Lys(K) | 17 | 10 | 13 | 9 | 14 | 9 | 7 | 19 | 11 |
| --- | Lys(K) | 49 | 37 | 16 | 15 | 15 | 14 | 7 | 19 | 11 |
| aug | Met(M) | 14 | 14 | 6 | 8 | 2 | 1 | 17 | 12 | 3 |
| --- | Met(M) | 14 | 14 | 6 | 8 | 2 | 1 | 17 | 12 | 3 |
| uuc | Phe(F) | 12 | 14 | 3 | 13 | 6 | 9 | 24 | 21 | 17 |
| uuu * | Phe(F) | 16 | 17 | 1 | 6 | 1 | 0 | 3 | 6 | 2 |
| --- | Phe(F) | 28 | 31 | 4 | 19 | 7 | 9 | 27 | 27 | 19 |
| cca * | Pro(P) | 9 | 14 | 4 | 1 | 0 | 2 | 1 | 6 | 0 |
| ccc | Pro(P) | 6 | 2 | 7 | 11 | 8 | 6 | 20 | 17 | 8 |
| ccg | Pro(P) | 0 | 1 | 1 | 3 | 0 | 2 | 4 | 2 | 6 |
| ccu | Pro(P) | 7 | 10 | 2 | 1 | 5 | 2 | 21 | 16 | 3 |
| --- | Pro(P) | 22 | 27 | 14 | 16 | 13 | 12 | 46 | 41 | 17 |
| agc | Ser(S) | 7 | 12 | 2 | 13 | 6 | 14 | 8 | 7 | 19 |
| agu * | Ser(S) | 7 | 14 | 2 | 4 | 1 | 1 | 2 | 1 | 10 |
| uca * | Ser(S) | 11 | 17 | 3 | 1 | 0 | 0 | 2 | 2 | 2 |
| ucc | Ser(S) | 7 | 10 | 9 | 9 | 14 | 11 | 11 | 8 | 16 |
| ucg | Ser(S) | 0 | 1 | 1 | 4 | 0 | 2 | 4 | 3 | 11 |
| ucu | Ser(S) | 11 | 10 | 1 | 4 | 2 | 5 | 9 | 8 | 15 |
| --- | Ser(S) | 43 | 64 | 18 | 35 | 23 | 33 | 36 | 29 | 73 |
| uaa | Ter(.) | 0 | 0 | 1 | 0 | 0 | 0 | 0 | 1 | 0 |
| uag | Ter(.) | 0 | 1 | 0 | 0 | 0 | 0 | 0 | 0 | 0 |
| uga | Ter(.) | 1 | 0 | 0 | 0 | 1 | 1 | 0 | 0 | 0 |
| --- | Ter(.) | 1 | 1 | 1 | 0 | 1 | 1 | 0 | 1 | 0 |
| aca * | Thr(T) | 10 | 21 | 1 | 5 | 4 | 2 | 2 | 1 | 4 |
| acc | Thr(T) | 9 | 6 | 9 | 13 | 13 | 14 | 12 | 16 | 28 |
| acg | Thr(T) | 1 | 1 | 3 | 2 | 0 | 2 | 1 | 1 | 8 |
| acu | Thr(T) | 10 | 17 | 5 | 4 | 0 | 3 | 16 | 12 | 14 |
| --- | Thr(T) | 30 | 45 | 18 | 24 | 17 | 21 | 31 | 30 | 54 |
| ugg | Trp(W) | 14 | 20 | 5 | 4 | 8 | 2 | 11 | 14 | 15 |
| --- | Trp(W) | 14 | 20 | 5 | 4 | 8 | 2 | 11 | 14 | 15 |

TABLE II-continued

| Codon | AA | NEP coding | DPP4 | SCCE | bovine prochymosin | chymotrypsin | Her2 Light chain | Stachybotrys oxidase B | stachybotrys oxidase A | glucoamylase w/out starch binding domain |
|---|---|---|---|---|---|---|---|---|---|---|
| uac | Tyr(Y) | 11 | 26 | 4 | 17 | 2 | 9 | 21 | 24 | 16 |
| uau * | Tyr(Y) | 22 | 30 | 0 | 5 | 0 | 2 | 4 | 4 | 6 |
| --- | Tyr(Y) | 33 | 56 | 4 | 22 | 2 | 11 | 25 | 28 | 22 |
| gua * | Val(V) | 5 | 7 | 0 | 2 | 0 | 1 | 0 | 2 | 2 |
| guc | Val(V) | 9 | 12 | 6 | 7 | 10 | 10 | 17 | 25 | 13 |
| gug | Val(V) | 13 | 14 | 10 | 14 | 14 | 4 | 8 | 6 | 14 |
| guu | Val(V) | 10 | 11 | 2 | 3 | 0 | 1 | 21 | 12 | 5 |
| --- | Val(V) | 37 | 44 | 18 | 26 | 24 | 16 | 46 | 45 | 34 |
| nnn | ???(X) | 0 | 0 | 0 | 0 | 0 | 0 | 3 | 0 | 0 |
| TOT | AL | 701 | 729 | 232 | 365 | 246 | 222 | 583 | 597 | 527 |

It is evident that many codons were not used or not used as often in the genes that expressed well. These codons were found much more frequently in those genes that were not expressed well (indicated with an asterisk in Table II). In the STI gene, we identified several such codons that were not used or not used often by other well expressed proteins and the codons were changed to the codons that are used more often in well expressed proteins. See Tables III and IV.

TABLE III

Codon usage for wild type STI: (without three glycine residues and six histidine residues and the stop codon)

| gca | Ala(A) | 4 # | cag | Gln(Q) | 2 # | uug | Leu(L) | 3 # | uaa | Ter(.) |
| 0 | | | | | | | | | | |
| gcc | Ala(A) | 2 # | --- | Gln(Q) | 5 # | --- | Leu(L) | 15 # | uag | Ter(.) |
| 0 | | | | | | | | | | |
| gcg | Ala(A) | 0 # | gaa | Glu(E) | 7 # | aaa | Lys(K) | 7 # | uga | Ter(.) |
| 0 | | | | | | | | | | |
| gcu | Ala(A) | 2 # | gag | Glu(E) | 6 # | aag | Lys(K) | 3 # | --- | Ter(.) |
| 0 | | | | | | | | | | |
| --- | Ala(A) | 8 # | --- | Glu(E) | 13 # | --- | Lys(K) | 10 # | aca | Thr(T) |
| 3 | | | | | | | | | | |
| aga | Arg(R) | 4 # | gga | Gly(G) | 6 # | aug | Met(M) | 2 # | acc | Thr(T) |
| 2 | | | | | | | | | | |
| agg | Arg(R) | 1 # | ggc | Gly(G) | 2 # | --- | Met(M) | 2 # | acg | Thr(T) |
| 1 | | | | | | | | | | |
| cga | Arg(R) | 1 # | ggg | Gly(G) | 3 # | uuc | Phe(F) | 4 # | acu | Thr(T) |
| 1 | | | | | | | | | | |
| cgc | Arg(R) | 1 # | ggu | Gly(G) | 5 # | uuu | Phe(F) | 5 # | --- | Thr(T) |
| 7 | | | | | | | | | | |
| cgg | Arg(R) | 0 # | --- | Gly(G) | 16 # | --- | Phe(F) | 9 # | ugg | Trp(W) |
| 2 | | | | | | | | | | |
| cgu | Arg(R) | 2 # | cac | His(H) | 0 # | cca | Pro(P) | 4 # | --- | Trp(W) |
| 2 | | | | | | | | | | |
| --- | Arg(R) | 9 # | cau | His(H) | 2 # | ccc | Pro(P) | 0 # | uac | Tyr(Y) |
| 0 | | | | | | | | | | |
| aac | Asn(N) | 4 # | --- | His(H) | 2 # | ccg | Pro(P) | 1 # | uau | Tyr(Y) |
| 4 | | | | | | | | | | |
| aau | Asn(N) | 5 # | aua | Ile(I) | 3 # | ccu | Pro(P) | 5 # | --- | Tyr(Y) |
| 4 | | | | | | | | | | |
| --- | Asn(N) | 9 # | auc | Ile(I) | 5 # | --- | Pro(P) | 10 # | gua | Val(V) |
| 0 | | | | | | | | | | |
| gac | Asp(D) | 3 # | auu | Ile(I) | 6 # | agc | Ser(S) | 1 # | guc | Val(V) |
| 0 | | | | | | | | | | |
| gau | Asp(D) | 14 # | --- | Ile(I) | 14 # | agu | Ser(S) | 1 # | gug | Val(V) |
| 8 | | | | | | | | | | |
| --- | Asp(D) | 17 # | cua | Leu(L) | 1 # | uca | Ser(S) | 3 # | guu | Val(V) |
| 6 | | | | | | | | | | |
| ugc | Cys(C) | 1 # | cuc | Leu(L) | 3 # | ucc | Ser(S) | 1 # | --- | Val(V) |
| 14 | | | | | | | | | | |
| ugu | Cys(C) | 3 # | cug | Leu(L) | 2 # | ucg | Ser(S) | 1 # | nnn | ???(X) |
| 0 | | | | | | | | | | |
| --- | Cys(C) | 4 # | cuu | Leu(L) | 5 # | ucu | Ser(S) | 4 # | TOTAL | |
| 181 | | | | | | | | | | |
| caa | Gln(Q) | 3 # | uua | Leu(L) | 1 # | --- | Ser(S) | 11 # | | |

TABLE IV

Codon usage for *A. niger* codon optimized STI I: (without three glycine residues and six histidine residues and the stop codon):

| Codon | AA | # | Codon | AA | # | Codon | AA | # | Codon | AA | # |
|---|---|---|---|---|---|---|---|---|---|---|---|
| gca | Ala(A) | 4 | cag | Gln(Q) | 2 | uug | Leu(L) | 0 | uaa | Ter(.) | 0 |
| gcc | Ala(A) | 2 | --- | Gln(Q) | 5 | --- | Leu(L) | 15 | uag | Ter(.) | 0 |
| gcg | Ala(A) | 0 | gaa | Glu(E) | 7 | aaa | Lys(K) | 7 | uga | Ter(.) | 0 |
| gcu | Ala(A) | 2 | gag | Glu(E) | 6 | aag | Lys(K) | 3 | --- | Ter(.) | 0 |
| --- | Ala(A) | 8 | --- | Glu(E) | 13 | --- | Lys(K) | 10 | aca | Thr(T) | 3 |
| aga | Arg(R) | 0 | gga | Gly(G) | 6 | aug | Met(M) | 2 | acc | Thr(T) | 2 |
| agg | Arg(R) | 1 | ggc | Gly(G) | 3 | --- | Met(M) | 2 | acg | Thr(T) | 1 |
| cga | Arg(R) | 1 | ggg | Gly(G) | 3 | uuc | Phe(F) | 4 | acu | Thr(T) | 1 |
| cgc | Arg(R) | 5 | ggu | Gly(G) | 4 | uuu | Phe(F) | 5 | --- | Thr(T) | 7 |
| cgg | Arg(R) | 0 | --- | Gly(G) | 16 | --- | Phe(F) | 9 | ugg | Trp(W) | 2 |
| cgu | Arg(R) | 2 | cac | His(H) | 0 | cca | Pro(P) | 0 | --- | Trp(W) | 2 |
| --- | Arg(R) | 9 | cau | His(H) | 2 | ccc | Pro(P) | 0 | uac | Tyr(Y) | 4 |
| aac | Asn(N) | 4 | --- | His(H) | 2 | ccg | Pro(P) | 1 | uau | Tyr(Y) | 0 |
| aau | Asn(N) | 5 | aua | Ile(I) | 0 | ccu | Pro(P) | 9 | --- | Tyr(Y) | 4 |
| --- | Asn(N) | 9 | auc | Ile(I) | 8 | --- | Pro(P) | 10 | gua | Val(V) | 0 |
| gac | Asp(D) | 3 | auu | Ile(I) | 6 | agc | Ser(S) | 1 | guc | Val(V) | 0 |
| gau | Asp(D) | 14 | --- | Ile(I) | 14 | agu | Ser(S) | 1 | gug | Val(V) | 8 |
| --- | Asp(D) | 17 | cua | Leu(L) | 1 | uca | Ser(S) | 3 | guu | Val(V) | 6 |
| ugc | Cys(C) | 1 | cuc | Leu(L) | 3 | ucc | Ser(S) | 1 | --- | Val(V) | 14 |
| ugu | Cys(C) | 3 | cug | Leu(L) | 6 | ucg | Ser(S) | 1 | nnn | ???(X) | 0 |
| --- | Cys(C) | 4 | cuu | Leu(L) | 5 | ucu | Ser(S) | 4 | TOTAL | | 181 |
| caa | Gln(Q) | 3 | uua | Leu(L) | 0 | --- | Ser(S) | 11 | | | |

The optimized DNA was synthesized by MCLAB (South San Francisco) in vitro as a DNA fragment containing three restriction sites (NheI at 5' end of gene and XhoI and BstEII at the 3' end), a kexB cleavage site and three *glycine* residues at N-terminal end and six histidine residues at C-terminal (SEQ I.D. NO:3). This optimized gene was cloned into a pCRII-TOPO vector. Following the procedures described in Example 1 above, the NheI to BstEII fragment was released from the plasmid by restriction digestion and the DNA fragment was purified on and extracted from an agarose gel and cloned into pSLGAMpR2 to create expression plasmid pSL-GAMpR2-SBTI (Q107).

The expression plasmid was transformed into dgr246ΔGAP:pyr2. The transformation and shake flask testing of transformants were as in Example 1. Thirty one transformants were assayed and SDS gel was used to check the level of protein expression. Broth from the top six transformants were assayed for trypsin inhibition activity.

Example 3

Expression of the Bowman-Birk Inhibitor and its Variants in *Aspergillus* a. BBI Fusion to Glucoamylase with kexB Site and with Three *Glycine* at N-Terminal End and Six Histidine Residues at C-Terminal:

Following procedures described in Example 2 above, the BBI-encoding DNA was optimized and used for this Example. The DNA was synthesized by MCLAB in vitro as a DNA fragment containing three restriction sites (NheI at 5' end of gene and XhoI and BstEII at the 3' end), a kexB cleavage site and three *glycine* residues at N-terminal and six histidine residues at C-terminal. (SEQ ID NO:54). It was cedures described in Example 1 above, the NheI to BstEII fragment was released from the plasmid by restriction diges- cloned into pCRII-TOPO vector Invitrogen. Following protion and the DNA fragment was extracted from agarose gel and cloned into pSLGAMpR2 to create expression plasmid pSLGAMpR2-BBIkex+ (Q104). The expression plasmid was transformed into dgr246ΔGAP:pyr2. The transformation and shake flask testing of transformants were same as Example 1. Twenty-eight transformants were generated and twenty-five transformants were assayed in shake flask. The SDS gel was used to check the level of protein expression. Broth from the top transformants were assayed for trypsin or chymotrypsin inhibition activity.

b. BBI Fusion to Glucoamylase with Six Histidine Residues at C-Terminal:

Following procedures described in Example 2 above, the BBI-encoding DNA was optimized and used for this Example. The DNA was synthesized by MCLAB in vitro as a DNA fragment containing three restriction sites (NheI at 5' end of gene and XhoI and BstEII at the 3' end) and six histidine residues at C-terminal. (SEQ ID NO:42: GCTAGCGACGAT-GAGAGCTCTAAGCCCTGTTGCGATCAGT-GCGCGTGTACCAAATCG AACCCTCCGCAGT-GTCGCTGCTCCGATATGCGTCTGAATTCCTGTCATA GCGCATGC AAGAGCTGTATCTGCGCCCTGAGCTAC-CCCGCGCAGTGTTTCTGCGTCGACATCACG GACT-TCTGCTACGAGCCGTGTAAGCCCAGC-GAGGACGATAAGGAGAACCATCATCAC CATCACCATTAGCTCGAGGGTGACC). It was cloned into pCRII-TOPO vector. Following procedures described in Example 1 above, the NheI to BstEII fragment was release from the plasmid by restriction digestion, purified and extracted from agarose gel, and cloned into pSLGAMpR2 to create expression plasmid pSLGAMpR2-BBIkex-(Q105). The expression plasmid was transformed into dgr246ΔGAP: pyr2. The transformation and shake flask testing of transformants were same as example 1. Thirty-eight transformants were generated and twenty-five transformants were assayed in shake flask. The SDS gel was used to check the level of protein expression. Broth from the top transformants were assayed for trypsin or chymotrypsin inhibition activity.

c. BBI Fusion to Glucoamylase with kexB Site and Three *Glycine* Residues at N-Terminal End:

The plasmid DNA, synthesized by MCLAB in vitro (SEQ ID NO:5) which was cloned into pCRII-TOPO vector, was used as DNA template for PCR amplification. Two primers were designed: 5' GGG CTA GCA ACG TCA TCT CCA AG 3' (SEQ ID NO:43) and 5' GGG GTC ACC TAG TTC TCC TTA TCG TCC TCG CTG 3' (SEQ ID NO:44). The DNA was amplified in the presence of the primers under the following conditions: The DNA was diluted 10 to 100 fold with Tris-EDTA buffer. Ten microliter of diluted DNA was added to the reaction mixture which contained 0.2 mM of each nucleotide (A, G. C and T), 1× reaction buffer, 0.5 to 0.6 microgram of primer 1 (SEQ ID NO:43) and primer 2 (SEQ ID NO:44) in a total of 100 microliter reaction in an eppendorf tube. After heating the mixture at 100° C. for 5 minutes, 2.5 units of Taq DNA polymerase were added to the reaction mix. The PCR reaction was performed at 95° C. for 1 minute, the primer was annealed to the template at 50° C. for 1 minute and extension was done at 72° C. for 1 minute. This cycle was repeated 30 times with an additional cycle of extension at 68° C. for 7 minutes before stored at 4° C. for further use. The PCR fragment detected by agarose gel was then cloned into the plasmid vector pCRII-TOPO (Invitrogen). The resulting PCR fragment contains identical sequence as SEQ ID NO:54, except the nucleotides encoding the six histidine residues and the XhoI restriction site were removed. Following procedures described in Example 1 above, the PCR fragment was digested with restriction enzymes NheI and BstEII. The digested DNA fragment was precipitated by ethanol and cloned into pSLGAMpR2 to create expression plasmid pSL-GAMpR2-BBI without histag (Q108). The expression plasmid was transformed into dgr246ΔGAP:pyr2. The transformation and shake flask testing of transformants were same as described in Example 1. Fifty-seven transformants were generated and twenty-five transformants were assayed in shake flask. The SDS gel was used to check the level of protein expression. Broth from the top transformants were assayed for trypsin or chymotrypsin inhibition activity.

d. BBI Fusion to Glucoamylase with kexB Site:

The plasmid DNA, synthesized by MCLAB in vitro (SEQ ID NO:1) which was cloned into pCRII-TOPO vector, was used as DNA template for PCR amplification. Two primers were designed: 5' GGG GTC ACC TAG TTC TCC TTA TCG TCC TCG CTG 3' (SEQ ID NO:44) and 5' GGG CTA GCA ACG TCA TCT CCA AGC GCG ACG ATG AGA GCT CTA AG 3' (SEQ ID NO:45). The resulting PCR fragment contains identical sequence as SEQ ID NO:54 (FIG. 1C), except the nucleotides encoding the three *glycine* residues and six histidine residues and XhoI restriction site were removed. Following procedures described in Example 1 above, the PCR fragment was digested with restriction enzymes NheI and BstEII. The digested DNA fragment was precipitated by ethanol and cloned into pSLGAMpR2 to create expression plasmid pSL-GAMpR2-BBI without 3 G and histag (Q109). The expression plasmid was transformed into dgr246ΔGAP:pyr2. The transformation and shake flask testing of transformants were same as Example 1. One hundred and twenty-seven transformants were generated and forty-two transformants were assayed in shake flask. The SDS gel was used to check the level of protein expression. Broth from the top transformants were assayed for trypsin or chymostrypsin inhibition activity.

Example 4

Expression of the Bowman-Birk Inhibitor and its Variants (Loop Replacement by Other Binders) in *Aspergillus*

Variant sequences were introduced into one or both loops of BBI using standard procedures known in the art. Variant sequences were determined by panning a commercially available phage peptide library PhD C7C (New England Biolabs, Beverly, Mass.) against target proteins or substrates for 3 rounds according to the manufacturers instructions, or using sequences with known activity. In the sequences provided below, the alterations introduced into the loop nucleotide sequence is indicated by lower case nucleotides.

a. BBI with a-VEGF (CK37281) in Loop I

The plasmid DNA, synthesized by MCLAB in vitro (SEQ ID NO:1) which was cloned into pCRII-TOPO vector, was used as DNA template for PCR amplification. Two primers were designed:

(SEQ ID NO: 46)
5' GTTGCGATCAGTGCGCGTGTtacaatctgtatggctggaccTGTCGC TGCT 3'

-continued and (SEQ ID NO: 47)
5' CGCATATCGGAGCAGCGACAggtccagccatacagattgtaACACGC

GCAC 3'.

to introduce a peptide sequence that binds to VEGF (denoted a-VEGF) to inhibit VEGF function. PCR was performed by heating mixture at 94° C. for 2 min, then 30 cycles of reaction at 94° C. for 30 second, 63° C. for 30 second and 72° C. for 30 second. After 30 cycles, the mixture was incubated at 72° C. for 4 min before it was stored at 4° C. The replacement binding loop was verified by DNA sequencing. The NheI to BstEII DNA fragment was released from plasmid by restriction digestion, purified and cloned into pSLGAMpR2 to create expression plasmid pSLGAMpR2-BBI (CK37281) in loop1 (Q117). The expression plasmid was transformed into dgr246ΔGAP:pyr2, The transformation and shake flask testing of transformants were same as in Example 1. More than thirty transformants were generated and forty-two transformants were assayed in shake flask. The SDS gel was used to check the level of protein expression.

b. BBI with a-VEGF (CK37281) Peptide in Loop II:

For plasmid construction, obtaining fungal transformants and assaying fungal transformant in shake flasks, we following same procedures as described in example above, except the following two primers were used:

(SEQ ID NO: 48)
5' CATGCAAGAGCTGTATCTGCtacaatctgtatggctggaccCAGTGT

TTCTG3'

(SEQ ID NO: 49)
5' GATGTCGACGCAGAAACACTGggtccagccatacagattgtaGCAGA

TACAG3'.

c. BBI with a-VEGF (CK37281) Peptide in Loop I and II:

For plasmid construction, obtaining fungal transformants and assaying fungal transformant in shake flasks, we following same procedures, except the following four primers were used:

(SEQ ID NO: 46)
5' GTTGCGATCAGTGCGCGTGTtacaatctgtatggctggaccTGTCGC

TGCT 3'

(SEQ ID NO: 47)
5' CGCATATCGGAGCAGCGACAggtccagccatacagattgtaACACGC

GCAC 3'

(SEQ ID NO: 48)
5' CATGCAAGAGCTGTATCTGCtacaatctgtatggctggaccCAGTGT

TTCTG3'

(SEQ ID NO: 49)
5' GATGTCGACGCAGAAACACTGggtccagccatacagattgtaGCAGA

TACAG3'.

d. BBI with A-Complement Protein c2 Peptide in loop I:

For plasmid construction, obtaining fungal transformants and assaying fungal transformant in shake flasks, we following same procedures, except the following two primers were used to introduce a peptide sequence that binds to c2 (denoted a-c2) to inhibit c2 function:

(SEQ ID NO: 50)
5'GCGATCAGTGCAGCTGTagctgcggcaggaagatccccatccagtgcT

GTCGCTGCTCCGATATGCGTC3'

(SEQ ID NO: 51)
5'GAGCAGCGACAgcactggatggggatcttcctgccgcagctACAGCTG

CACTGATCGCAACAGGGCTTA3' e. BBI with A-Complement Protein c3 Peptide in Loop I:

For plasmid construction, obtaining fungal transformants and assaying fungal transformant in shake flasks, we following same procedures, except the following two primers were used to introduce a peptide sequence that binds to c3 (denoted a-c3) to inhibit c3 function:

(SEQ ID NO: 52)
5' GCGATCAGTGCGGCTGTgccaggagcaacctcgacgagTGTCGCTGC

TCCGATATGCGTC 3'

(SEQ ID NO: 53)
5' GAGCAGCGACActcgtcgaggttgctcctggcACAGCCGCACTGATC

GCAACAGGGCTTA 3' f. BBI with A-Complement Protein c4 Peptide in Loop I:

For plasmid construction, obtaining fungal transformants and assaying fungal transformant in shake flasks, we following same procedures, except the following two primers were used to introduce a peptide sequence that binds to c4 (denoted a-c4) to inhibit c4 function:

(SEQ ID NO: 55)
5' GCGATCAGTGCGCGTGTcagagggccctccccatcctcTGTCGCTGC

TCCGATATGCGTC 3'

(SEQ ID NO: 56)
5' GAGCAGCGACAgaggatggggagggccctctgACACGCGCACTGATC

GCAACAGGGCTTA 3' g. BBI with A-Complement Protein c5 Peptide in Loop I:

For plasmid construction, obtaining fungal transformants and assaying fungal transformant in shake flasks, we following same procedures, except the following two primers were used to introduce a peptide sequence that binds to c5 (denoted a-c5) to inhibit c5 function:

(SEQ ID NO: 57)
5' GCGATCAGTGCCAGTGTggcaggctccacatgaagaccTGTCGCTGC

TCCGATATGCGTC 3'

(SEQ ID NO: 58)
5' GAGCAGCGACAggtcttcatgtggagcctgccACACTGGCACTGATC

GCAACAGGGCTTAGA 3' h. BBI with A-Human Complement Factor B Peptide in Loop I:

For plasmid construction, obtaining fungal transformants and assaying fungal transformant in shake flasks, we following same procedures, except the following two primers were used to introduce a peptide sequence that binds to Factor B (denoted a-Factor B) to inhibit Factor B function:

(SEQ ID NO: 59)
5' GCGATCAGTGCCAGTGTaagaggaagatcgtcctcgacTGTCGCTGC
TCCGATATGCGTC 3'

(SEQ ID NO: 60)
5' GAGCAGCGACAgtcgaggacgatcttcctcttACACTGGCACTGATC
GCAACAGGGCTTAGA 3' i. BBI with A-Membrane Metalloprotease 2 (MMP2) Peptide in Loop I:

For plasmid construction, obtaining fungal transformants and assaying fungal transformant in shake flasks, we following same procedures, except the following two primers were used to introduce a peptide sequence that binds to MMP2 (denoted a-MMP2) to inhibit MMP2 function:

(SEQ ID NO: 61)
5' CAGTGCGCGTGTgccgccatgttcggccccgccTGTCGCTGCTCCGA
TATGCGTC 3'

(SEQ ID NO: 62)
5' GAGCAGCGACAggcggggccgaacatggcggcACACGCGCACTGATC
GCAACAG 3' j. BBI with A-Membrane Metalloprotease 12 (MMP12) Peptide in Loop I:

For plasmid construction, obtaining fungal transformants and assaying fungal transformant in shake flasks, we following same procedures, except the following two primers were used to introduce a peptide sequence that binds to MMP12 (denoted a-MMP12) to inhibit MMP12 function:

(SEQ ID NO: 63)
5' CAGTGCGCGTGTggcgccctcggcctcttcggcTGTCGCTGCTCCGA
TATGCGTC 3'

(SEQ ID NO: 64)
5' GAGCAGCGACAgccgaagaggccgagggcgccACACGCGCACTGATC
GCAACAG 3' k. BBI with Cotton Binding Peptide 2314 in Loop I:

For plasmid construction, obtaining fungal transformants and assaying fungal transformant in shake flasks, we following same procedures, except the following two primers were used to introduce a peptide sequence that binds to cotton:

(SEQ ID NO: 65)
5' GTTGCGATCAGTGCGCGTGTgagcccctgatccaccagcgcTGTCGC
TGCT 3'

(SEQ ID NO: 66)
5' CGCATATCGGAGCAGCGACAgcgctggtggatcaggggctcACACGC
GCAC 3' l. BBI with Cotton Binding Peptide 2317 in Loop I:

For plasmid construction, obtaining fungal transformants and assaying fungal transformant in shake flasks, we following same procedures, except the following two primers were used to introduce a peptide sequence that binds to cotton:

(SEQ ID NO: 67)
5' GTTGCGATCAGTGCGCGTGTagcgccttccgcggccccaccTGTCGC
TGCT 3'

(SEQ ID NO: 68)
5' CGCATATCGGAGCAGCGACAggtggggccgcggaaggcgctACACGC
GCAC 3' m. BBI with Compstatin Loop in Loop I:

For plasmid construction, obtaining fungal transformants and assaying fungal transformant in shake flasks, we following same procedures, except the following two primers were used to introduce the compstatin peptide sequence:

(SEQ ID NO: 69)
5' GTTGCGATCAGTGCGCGTGTgttgttcaggactggggccaccaccgc
TGTCGCTGCT (SEQ ID NO: 70)
5' CGCATATCGGAGCAGCGACAgcggtggtggcccagtcctgaacaac
ACACGCGCAC In this case, the 7 amino acids from the BBI Trypsin binding loop was replaced by 9 amino acids from compstatin binding loops.

n. BBI with Compstatin Loop in Loop II:

For plasmid construction, obtaining fungal transformants and assaying fungal transformant in shake flasks, we following same procedures, except the following two primers were used to introduce the compstatin peptide sequence:

(SEQ ID NO: 71)
5' CATGCAAGAGCTGTATCTGCgttgttcaggactggggccaccaccgc
TGTTTCTGCG (SEQ ID NO: 72)
5' GTGATGTCGACGCAGAAACAgcggtggtggcccagtcctgaacaac
GCAGATACAG In this case, the 7 amino acids from the BBI Trypsin binding loop was replaced by 9 amino acids from compstatin binding loops.

Example 5

Expression of the Bowman-Birk Inhibitor and its Variants in *Trichoderma Reesei*

Following procedures described in Example 2 above, the BBI-encoding DNA was optimized and used for this Example. Two primers were designed to amplify the DNA fragment using plasmid pSLGAMpR2-BBI or pSLGAMpR2-BBI with a-VEGF (CK37281) peptide in loop I and II as templates:

(SEQ ID NO: 73)
5' GGA CTA GTA AGC GCG ACG ATG AGA GCT CT 3'

-continued (SEQ ID NO: 74)
5' AAG GCG CGC CTA GTT CTC CTT ATC GTC CT 3'

A third primer was also used to create a PCR fragment which contains three *glycine* residues at the N-terminal of the BBI protein when used in conjunction with primer #2 (SEQ ID NO:74) above.

(SEQ ID NO: 75)
5' GGA CTA GTA AGC GCG GCG GTG GCG ACG ATG AGA GCT CT 3'.

Figure 8:
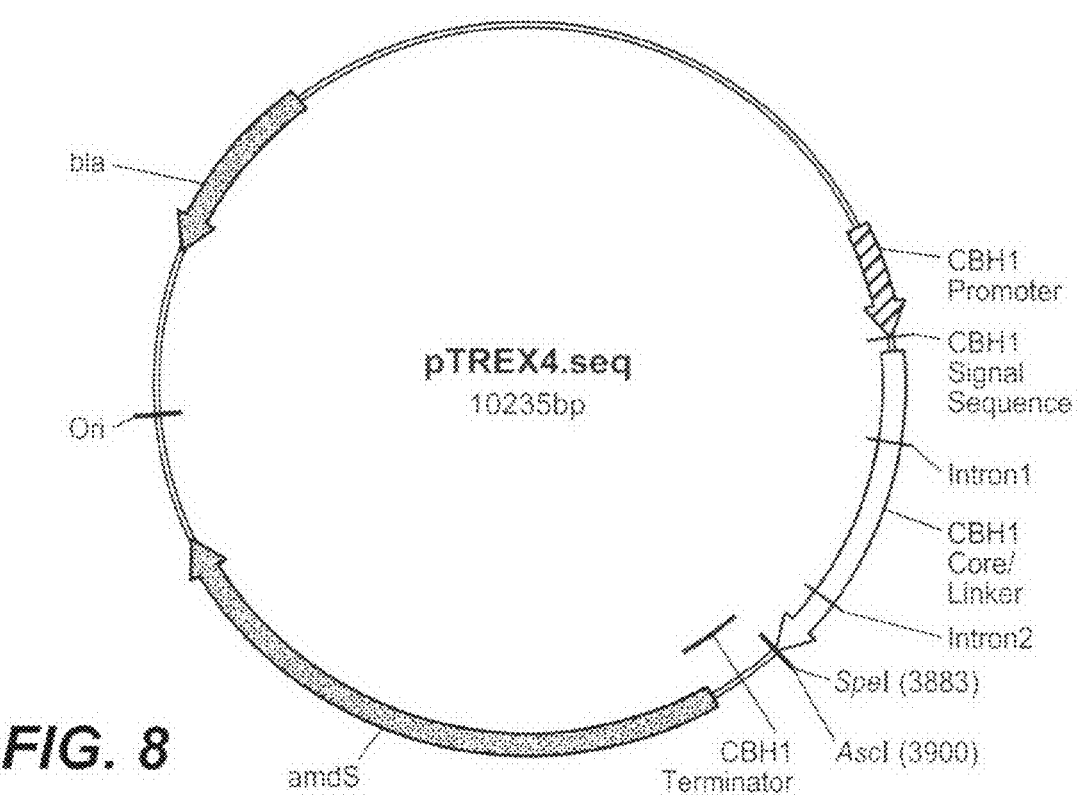
FIG. 8 is a diagram of the plasmid pTrex4.

Following the same procedures described in Example 2 above, the BBI-encoding DNA was optimized and used for this Example, the PCR fragment was cut with restriction enzyme SpeI and AscI and ligated to the *Trichoderma* expression plasmid, pTrex4 (FIG. 8) which is a modified version of pTREX2 (see FIG. 9), which in turn is a modified version of pTEX, see PCT Publication No. WO 96/23928 for a complete description of the preparation of the pTEX vector, herein incorporated by reference, which contains a CBHI promoter and terminator for gene expression and a *Trichoderma* pyr4 gene as a selection marker for transformants, to create an expression plasmid. In the pTrex4 plasmid, the BBI gene was fused to the C-terminus of the CBH I core and linker from *T. reesei*. The amdS gene from *A. nidulans* was used as the selection marker during fungal transformation. The expression plasmid was transformed into *Trichoderma reesei*. Stable transformants were isolated on *Trichoderma* minimal plates with acetamide as the nitrogen source. The transformants were grown on the amd minus plate which contains 1 ml/l 1000× salts, 20 g/l Noble Agar, 1.68 g/l CsCl, 20 g/l Glucose, 15 g/l KH2PO4, 0.6 g/l MgSO4*7H2O, 0.6 g/l CaCl2*2H2O and 0.6 g/l Acetamide. The final pH was adjusted to 4.5. The 1000× salts contains 5 g/l FeSO4, 1.6 g/l MnSO4, 1.4 g/l ZnSO4 and 1 g/l CoCl2. It was filter sterilized. After three days incubation at 28° C., the transformants were transferred to the fresh amd minus plates and grown for another three days at 28° C.

The transformants were then inoculated into *T. reesei* proflo medium (50 ml for each transformant) in 250-ml shake flasks. *T. reesei* proflo medium contains 30 g/l Alpha-lactose, 6.5 g/l (NH4)2SO4, 2 g/l KH2PO4, 0.3 g/l MgSO4*7H2O, 0.2 g/l CaCl2, 1 ml/l 1000× TRI Trace Salts, 2 ml/l 10% Tween 80, 22.5 g/l Proflo and 0.72 g/l CaCO3. The 1000× TRI Trace Salts contains 5 g/l FeSO4*7H2O, 1.6 g/l MnSO4*H2O and 1.4 g/l ZnSO4*7H2O. After growing at 30° C. for 2 days, 4 ml of culture was transferred into defined medium which contains 5 g/l (NH4)2SO4, 33 g/l PIPPS buffer, 9 g/l CASAMINO ACIDS, 4.5 g/l KH2PO4, 1 g/l CACL2, 1 g/l MgSO4*7H2O, 5 ml/l MAZU and 2.5 ml/l 400× *T.reesei* TRACE. Its pH was adjusted to 5.5 and 40 ml/l 40% lactose was added after sterilization. The 400× *T.reesei* TRACE contains 175 g/l Citric Acid (anhydrous), 200 g/l FeSO4*7H2O, 16 g/l ZnSO4*7H2O, 3.2 g/l CuSO4*5H2O, 1.4 g/l MnSO4*H2O and 0.8 g/l H3BO3 (Boric Acid).

About 40 transformants were generated on the plates and 20 were assayed in shake flasks. The supernatant of the culture was used for SDS-PAGE analysis and assayed for trypsin or chymotrypsin inhibitory activity. Western blot also showed the presence of both fusion (Cbhl-BBI) and BBI alone.

Example 6

Co-Expression of the Bowman-Birk Inhibitor and Secretory Chaperones in *Aspergillus*

The following example details how secretion can be enhanced. STI protein contains two disulfide bonds and BBI contains 7 disulfide bonds in their tertiary structures and these disulfide bonds are important for their function. It is known that folding of protein with disulfide bonds require Protein Disulfide Isomerase (PDI) or other chaprones in ER.

Figure 7:
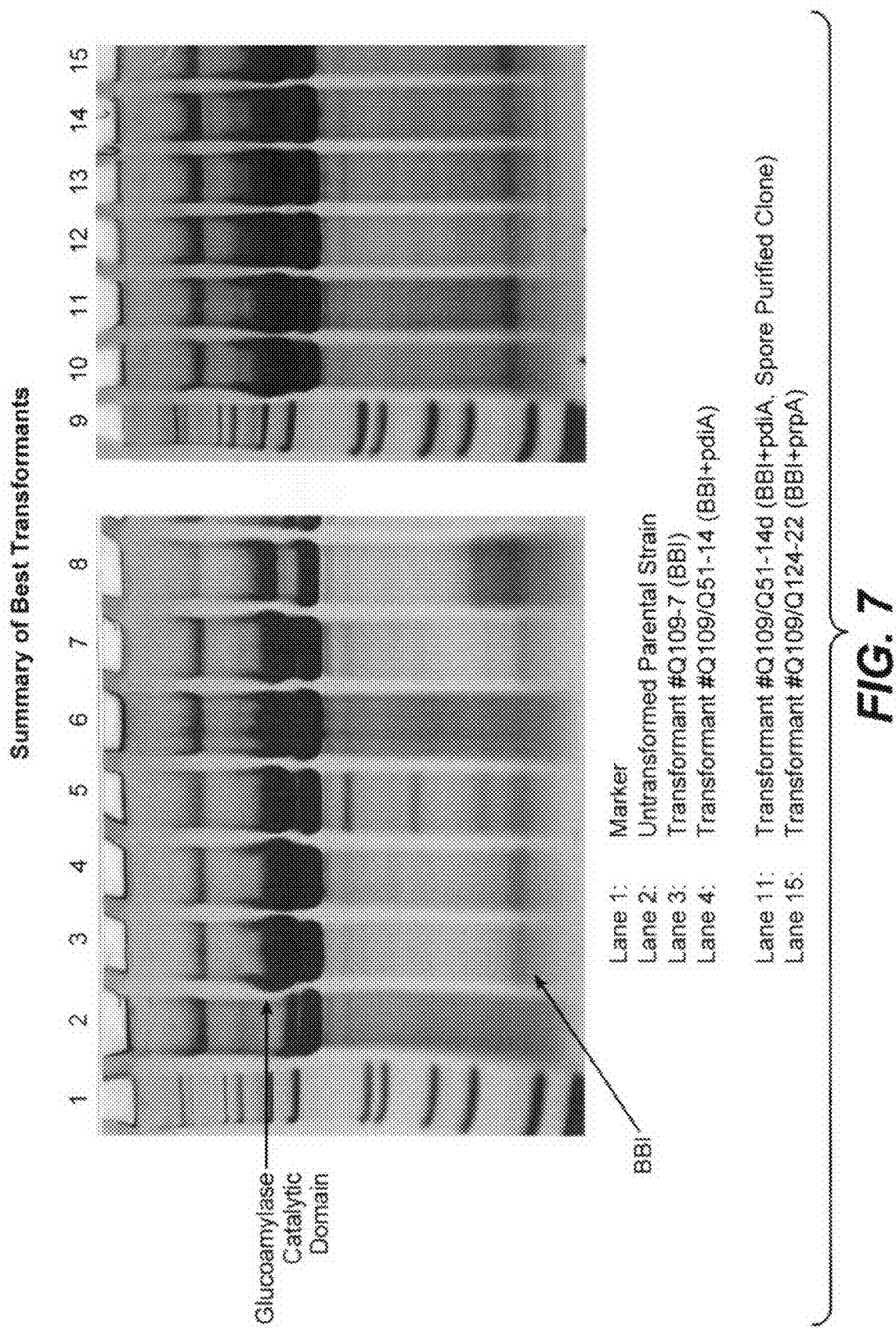
FIG. 7 is a photograph of a protein SDS gel. Lane 1 contains molecular weight markers. Lane 2 is the untransformed parental strain. Lane 3 is the parental strain transformed with BBI-encoding DNA. Lane 4 is the parental strain co-transformed with a BBI-encoding vector and a chaperone (pdiA)-encoding vector. Lane 15 is the parental strain co-transformed with a BBI-encoding vector and a chaperone (prpA)-encoding vector. Expression of the desired protein, e.g., BBI, was enhanced in the presence of the chaperone.

Enhancement of STI or BBI expression was investigated by co-transformation of two plasmids or by sequential transformation of two plasmids, one contains STI or BBI expression cassette and the other one contains the PDI genes or chaperone genes. First, we co-transform plasmid pSL-GAMpR2-BBI without 3 G and histag (Q109) with plasmid Q51 which contains 4.6 kb genomic DNA covering region of the pdiA gene from *Aspergillus niger* in vector pUC219 into same strain (dgr246ΔGAP:pyr2). Fifty-one transformants were obtained and forty-seven transformants were screened in shake flasks. Transformant #14 was selected because it produced the highest amount of BBI protein based on SDS gel data. The expression level of BBI protein is higher in the co-transformed stain than the strain containing only plasmid pSLGAMpR2-BBI without 3 G and histag (Q109). FIG. 7 illustrates the enhanced BBI expression. This strain was also spore purified and tested again in shake flask.

Following procedures described above, we also decide to co-transform plasmid pSLGAMpR2-BBI without histag (Q108) with plasmid Q51 containing pdiA gene (same as above) into same strain (dgr246ΔGAP:pyr2). Thirty-four transformants were screened in shake flasks. One transformant was selected for its ability to produce BBI protein at the highest level based on the SDS gel date. The expression level of BBI protein is higher than the strain containing only plasmid pSLGAMpR2-BBI without histag (Q108).

Following procedures described above, we also decide to co-transform plasmid pSLGAMpR2-BBI without 3 G and histag (Q109) with plasmid Q124 which contains 1623 bp genomic DNA covering region of the prpA gene from *Aspergillus niger* in vector pUC219 into same strain (dgr246ΔGAP:pyr2). Twenty-eight transformants were screened in shake flasks. One transformant was selected for its ability to produced the highest amount of BBI protein based on the SDS gel date. The expression level of BBI protein is higher in the co-transformed stain than the strain containing only plasmid pSLGAMpR2-BBI without 3 G and histag (Q109). FIG. 7 illustrates the enhancement (lane 15 vs lane 3). This strain was spore purified and tested again in shake flask.

Example 7

Recombinant Protease Inhibitor Variants Retain Activity

STI, BBI and variants thereof produced using the methods described above were tested for activity, e.g., inhibition of protease activity.

a. Protease Inhibition

950 µl of Tris-buffered saline+0.02% Tween 20 is combined with 20 µl protease (100 µg/ml in 1 mM HCl (bovine trypsin or chymotrypsin)) and 20 μl sample. The solution is mixed and incubated for 30 min. at room temperature. 10 μl substrate (for trypsin: succinyl-ala-ala-pro-arg-paranitroanilide, 10 mg/ml in DMSO; for chymotrypsin: succinyl ala-ala-pro-phe-paranitroanilide, 10 mg/ml in DMSO) is added and the solution mixed. Absorbance is monitored at 405 nm and the rate determined ($A_{405}$/min). The fraction of protease activity inhibited is determined by comparison with a control sample blank and calculated according to the following equation:

$$\left(\frac{A_{405}/\text{min(sample)}}{A_{405}/\text{min(blank)}}\right) * 100 \ \mu\text{g/ml(protease)} * \left(\frac{MW\text{inhibitor}}{MW\text{protease}}\right) = [\text{inhibitor}] \ \mu\text{g/ml}$$

b. Inhibition of HUVEC Proliferation by aVEGF Peptides.

HUVE cells (Cambrex, East Rutherford, N.J.) were passaged 1-5 times and maintained according to manufacturers instructions. HUVEC growth was stimulated by 0.03 to 20 ng/ml VEGF with the highest proliferation at 10 ng/ml $VEGF_{165}$ (R&D systems); this concentration was used in subsequent experiments. A series of a-VEGF peptides (see Example 4) from 0.00052 μM to 25 μM and an anti-VEGF MAb control (R&D Systems) were mixed with 10 ng/mL VEGF prior to addition to HUVECs seeded in triplicate in 96-well plates. Cell proliferation was measured by $^3$H-thymidine incorporation. Significant inhibition was observed (data not shown).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A composition comprising a protease inhibitor selected from the group consisting of:
   a Bowman-Birk inhibitor (BBI) comprising SEQ ID NO:7 wherein residue 13 is Ala or is changed to Ser, Gly or Gln, and wherein residues 15-21 and/or 42-48 have been replaced with a variant sequence; and
   a Soybean Trypsin Inhibitor (STI) comprising SEQ ID NO:12 wherein residues 40-85 and/or 137-144 have been replaced with a variant sequence;
   wherein said variant sequence is selected from the group consisting of:
      a VEGF binding peptide consisting of YNLYGWT (SEQ ID NO:77);
      a complement protein c2 binding peptide consisting of GRKIPIQ (SEQ ID NO:78);
      a complement protein c3 binding peptide consisting of ARSNLDE (SEQ ID NO:79);
      a complement protein c4 binding peptide consisting of QRALPIL (SEQ ID NO:80);
      a complement protein c5 binding peptide consisting of GRLHMKT (SEQ ID NO:81);
      a complement factor B binding peptide consisting of KRKIVLD (SEQ ID NO:82);
      a membrane metalloprotease 2 binding peptide consisting of AAMFGPA (SEQ ID NO:83);
      a membrane metalloprotease 12 binding peptide consisting of GALGLFG (SEQ ID NO:84);
      a cotton binding peptide consisting of EPLIHQR (SEQ ID NO:85); and a cotton binding peptide consisting of SAFRGPT (SEQ ID NO:86), wherein said protease inhibitor is produced in a filamentous fungal cell according to a method comprising, a) introducing a DNA construct into a filamentous fungal cell, wherein said DNA construct comprises a promoter showing transcription activity in the filamentous fungal cell and which is operably linked to a heterologous DNA sequence encoding the protease inhibitor, b) culturing the filamentous fungal cell under suitable culture conditions to allow expression of the heterologous DNA sequence, and c) producing the protease inhibitor.

2. The of claim 1, wherein said method further comprises recovering the protease inhibitor.

3. The composition of claim 1, wherein said filamentous fungal cell is selected from an *Aspergillus* strain, a *Penicillium* strain, a *Fusarium* strain or a *Trichoderma* strain.

4. The composition of claim 3, wherein said *Trichoderma* strain is *T. reesei.*

5. The composition of claim 3, wherein said *Aspergillus* strain is *A. niger, A. nidulans, A. awamori* or *A. oryzea.*

6. The composition of claim 1, wherein said protease inhibitor is a BBI comprising SEQ ID NO:7, wherein residue 13 is Ala or is changed to Ser, Gly or Gln, and wherein residues 15-21 and/or 42-48 have been replaced with a variant sequence or consisting of SEQ ID NO:7.

7. The composition of claim 1, wherein said protease inhibitor is a STI comprising SEQ ID NO:12, wherein residues 40-85 and/or 137-144 have been replaced with a variant sequence.

8. The composition of claim 1, wherein said protease inhibitor is selected from the group consisting of SEQ ID NOs:15-29.

9. The composition of claim 1, wherein said DNA sequence encoding the protease inhibitor includes codons that have been optimized for expression in the filamentous fungal cell.

10. The composition of claim 1, wherein said method further comprises introducing a second nucleic acid sequence encoding a chaperone into the filamentous fungal cell.

11. The composition of claim 10, wherein said chaperone is pdiA or prpA.

12. The composition of claim 1, wherein said protease inhibitor is expressed as a fusion protein.

13. The composition of claim 12, wherein said fusion protein includes a glucoamylase signal sequence, a glucoamylase catalytic domain, a cleavage site, and the protease inhibitor.

14. The composition of claim 12, wherein said fusion protein is processed by a protease to liberate the protease inhibitor.

* * * * *

UNITED STATES PATENT AND TRADEMARK OFFICE
CERTIFICATE OF CORRECTION

PATENT NO.         : 7,592,420 B2
APPLICATION NO. : 11/848196
DATED              : September 22, 2009
INVENTOR(S)       : Hans De Nobel et al.

It is certified that error appears in the above-identified patent and that said Letters Patent is hereby corrected as shown below:

In Column 82, Claim 2
    On line 1, please insert --composition-- between "The" and "of".

Signed and Sealed this

Tenth Day of November, 2009

David J. Kappos
*Director of the United States Patent and Trademark Office*

SEQUENCE LISTING

<160> NUMBER OF SEQ ID NOS: 76

<210> SEQ ID NO 1
<211> LENGTH: 253
<212> TYPE: DNA
<213> ORGANISM: Glycine max

<400> SEQUENCE: 1

```
gctagcaacg tcatctccaa gcgcgacgat gagagctcta agccctgttg cgatcagtgc      60
gcgtgtacca aatcgaaccc tccgcagtgt cgctgctccg atatgcgtct gaattcctgt     120
catagcgcat gcaagagctg tatctgcgcc ctgagctacc ccgcgcagtg tttctgcgtc     180
gacatcacgg acttctgcta cgagccgtgt aagcccagcg aggacgataa ggagaactag     240
ctcgagggtg acc                                                       253
```

<210> SEQ ID NO 2
<211> LENGTH: 213
<212> TYPE: DNA
<213> ORGANISM: Glycine max

<400> SEQUENCE: 2

```
gacgatgaga gctctaagcc ctgttgcgat cagtgcgcgt gtaccaaatc gaaccctccg      60
cagtgtcgct gctccgatat gcgtctgaat tcctgtcata gcgcatgcaa gagctgtatc    120
tgcgccctga gctacccccgc gcagtgtttc tgcgtcgaca tcacggactt ctgctacgag    180
ccgtgtaagc cagcgagga cgataaggag aac                                  213
```

<210> SEQ ID NO 3
<211> LENGTH: 610
<212> TYPE: DNA
<213> ORGANISM: Glycine max

<400> SEQUENCE: 3

```
gctagcaacg tcatctccaa gcgcggcggt ggcgatttcg tgctcgataa tgaaggcaac      60
cctcttgaaa atggtggcac atactacatc ctgtcagaca tcacagcatt tggtggaatc    120
cgcgcagccc tacgggaaa tgaacgctgc cctctcactg tggtgcaatc tcgcaatgag    180
```

```
ctcgacaaag ggattggaac aatcatctcg tcccccttacc gaatccgttt tatcgccgaa      240
ggccatcctc tgagccttaa gttcgattca tttgcagtta tcatgctgtg tgttggaatt      300
cctaccgagt ggtctgttgt ggaggatcta cctgaaggac ctgctgttaa aattggtgag      360
aacaaagatg caatggatgg ttggtttcgc cttgagcgcg tttctgatga tgaattcaat      420
aactacaagc ttgtgttctg tcctcagcaa gctgaggatg acaaatgtgg ggatattggg      480
attagtattg atcatgatga tggaaccagg cgtctggtgg tgtctaagaa caaaccgctg      540
gtggttcagt ttcaaaaact tgataaagaa tcactgcacc atcaccatca ccactagctc      600
gagggtgacc                                                             610
```

```
<210> SEQ ID NO 4
<211> LENGTH: 18
<212> TYPE: DNA
<213> ORGANISM: Glycine max

<400> SEQUENCE: 4
aacgtcatct ccaagcgc                                                     18
```

```
<210> SEQ ID NO 5
<211> LENGTH: 262
<212> TYPE: DNA
<213> ORGANISM: Glycine max

<400> SEQUENCE: 5
gctagcaacg tcatctccaa gcgcggcggt ggcgacgatg agagctctaa gccctgttgc       60
gatcagtgcg cgtgtaccaa atcgaaccct ccgcagtgtc gctgctccga tatgcgtctg      120
aattcctgtc atagcgcatg caagagctgt atctgcgccc tgagctaccc cgcgcagtgt      180
ttctgcgtcg acatcacgga cttctgctac gagccgtgta agcccagcga ggacgataag      240
gagaactagc tcgagggtga cc                                               262
```

```
<210> SEQ ID NO 6
<211> LENGTH: 543
<212> TYPE: DNA
<213> ORGANISM: Glycine max

<400> SEQUENCE: 6
gatttcgtgc tcgataatga aggcaaccct cttgaaaatg gtggcacata ctacatcctg       60
tcagacatca cagcatttgg tggaatccgc gcagccccta cgggaaatga acgctgccct      120
ctcactgtgg tgcaatctcg caatgagctc gacaaaggga ttggaacaat catctcgtcc      180
ccttaccgaa tccgttttat cgccgaaggc catcctctga gccttaagtt cgattcattt      240
gcagttatca tgctgtgtgt tggaattcct accgagtggt ctgttgtgga ggatctacct      300
gaaggacctg ctgttaaaat tggtgagaac aaagatgcaa tggatggttg gtttcgcctt      360
gagcgcgttt ctgatgatga attcaataac tacaagcttg tgttctgtcc tcagcaagct      420
gaggatgaca aatgtgggga tattgggatt agtattgatc atgatgatgg aaccaggcgt      480
ctggtggtgt ctaagaacaa accgctggtg gttcagtttc aaaaacttga taaagaatca      540
ctg                                                                    543
```

```
<210> SEQ ID NO 7
<211> LENGTH: 71
<212> TYPE: PRT
<213> ORGANISM: Glycine max

<400> SEQUENCE: 7
```

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Ile Thr Asp Phe Cys Tyr Glu Pro Cys Lys Pro
    50                  55                  60

Ser Glu Asp Asp Lys Glu Asn
65              70

<210> SEQ ID NO 8
<211> LENGTH: 74
<212> TYPE: PRT
<213> ORGANISM: Artificial Sequence
<220> FEATURE:
<223> OTHER INFORMATION: synthetic

<400> SEQUENCE: 8

Gly Gly Gly Asp Asp Glu Ser Ser Lys Pro Cys Cys Asp Gln Cys Ala
1               5                   10                  15

Cys Thr Lys Ser Asn Pro Pro Gln Cys Arg Cys Ser Asp Met Arg Leu
            20                  25                  30

Asn Ser Cys His Ser Ala Cys Lys Ser Cys Ile Cys Ala Leu Ser Tyr
        35                  40                  45

Pro Ala Gln Cys Phe Cys Val Asp Ile Thr Asp Phe Cys Tyr Glu Pro
    50                  55                  60

Cys Lys Pro Ser Glu Asp Asp Lys Glu Asn
65              70

<210> SEQ ID NO 9
<211> LENGTH: 80
<212> TYPE: PRT
<213> ORGANISM: Artificial Sequence
<220> FEATURE:
<223> OTHER INFORMATION: synthetic

<400> SEQUENCE: 9

Gly Gly Gly Asp Asp Glu Ser Ser Lys Pro Cys Cys Asp Gln Cys Ala
1               5                   10                  15

Cys Thr Lys Ser Asn Pro Pro Gln Cys Arg Cys Ser Asp Met Arg Leu
            20                  25                  30

Asn Ser Cys His Ser Ala Cys Lys Ser Cys Ile Cys Ala Leu Ser Tyr
        35                  40                  45

Pro Ala Gln Cys Phe Cys Val Asp Ile Thr Asp Phe Cys Tyr Glu Pro
    50                  55                  60

Cys Lys Pro Ser Glu Asp Asp Lys Glu Asn His His His His His
65              70                  75                  80

<210> SEQ ID NO 10
<211> LENGTH: 190
<212> TYPE: PRT
<213> ORGANISM: Artificial Sequence
<220> FEATURE:
<223> OTHER INFORMATION: synthetic

<400> SEQUENCE: 10

Gly Gly Gly Asp Phe Val Leu Asp Asn Glu Gly Asn Pro Leu Glu Asn
1               5                   10                  15

```
Gly Gly Thr Tyr Tyr Ile Leu Ser Asp Ile Thr Ala Phe Gly Gly Ile
            20                  25                  30

Arg Ala Ala Pro Thr Gly Asn Glu Arg Cys Pro Leu Thr Val Val Gln
        35                  40                  45

Ser Arg Asn Glu Leu Asp Lys Gly Ile Gly Thr Ile Ile Ser Ser Pro
50                  55                  60

Tyr Arg Ile Arg Phe Ile Ala Glu Gly His Pro Leu Ser Leu Lys Phe
65                  70                  75                  80

Asp Ser Phe Ala Val Ile Met Leu Cys Val Gly Ile Pro Thr Glu Trp
                85                  90                  95

Ser Val Val Glu Asp Leu Pro Glu Gly Pro Ala Val Lys Ile Gly Glu
                100                 105                 110

Asn Lys Asp Ala Met Asp Gly Trp Phe Arg Leu Glu Arg Val Ser Asp
            115                 120                 125

Asp Glu Phe Asn Asn Tyr Lys Leu Val Phe Cys Pro Gln Gln Ala Glu
        130                 135                 140

Asp Asp Lys Cys Gly Asp Ile Gly Ile Ser Ile Asp His Asp Asp Gly
145                 150                 155                 160

Thr Arg Arg Leu Val Val Ser Lys Asn Lys Pro Leu Val Val Gln Phe
                165                 170                 175

Gln Lys Leu Asp Lys Glu Ser Leu His His His His His His
            180                 185                 190

<210> SEQ ID NO 11
<211> LENGTH: 184
<212> TYPE: PRT
<213> ORGANISM: Glycine max

<400> SEQUENCE: 11

Gly Gly Gly Asp Phe Val Leu Asp Asn Glu Gly Asn Pro Leu Glu Asn
1               5                   10                  15

Gly Gly Thr Tyr Tyr Ile Leu Ser Asp Ile Thr Ala Phe Gly Gly Ile
            20                  25                  30

Arg Ala Ala Pro Thr Gly Asn Glu Arg Cys Pro Leu Thr Val Val Gln
        35                  40                  45

Ser Arg Asn Glu Leu Asp Lys Gly Ile Gly Thr Ile Ile Ser Ser Pro
50                  55                  60

Tyr Arg Ile Arg Phe Ile Ala Glu Gly His Pro Leu Ser Leu Lys Phe
65                  70                  75                  80

Asp Ser Phe Ala Val Ile Met Leu Cys Val Gly Ile Pro Thr Glu Trp
                85                  90                  95

Ser Val Val Glu Asp Leu Pro Glu Gly Pro Ala Val Lys Ile Gly Glu
                100                 105                 110

Asn Lys Asp Ala Met Asp Gly Trp Phe Arg Leu Glu Arg Val Ser Asp
            115                 120                 125

Asp Glu Phe Asn Asn Tyr Lys Leu Val Phe Cys Pro Gln Gln Ala Glu
        130                 135                 140

Asp Asp Lys Cys Gly Asp Ile Gly Ile Ser Ile Asp His Asp Asp Gly
145                 150                 155                 160

Thr Arg Arg Leu Val Val Ser Lys Asn Lys Pro Leu Val Val Gln Phe
                165                 170                 175

Gln Lys Leu Asp Lys Glu Ser Leu
            180

<210> SEQ ID NO 12
```

```
<211> LENGTH: 181
<212> TYPE: PRT
<213> ORGANISM: Glycine max

<400> SEQUENCE: 12

Asp Phe Val Leu Asp Asn Glu Gly Asn Pro Leu Glu Asn Gly Gly Thr
  1               5                  10                  15

Tyr Tyr Ile Leu Ser Asp Ile Thr Ala Phe Gly Gly Ile Arg Ala Ala
             20                  25                  30

Pro Thr Gly Asn Glu Arg Cys Pro Leu Thr Val Val Gln Ser Arg Asn
         35                  40                  45

Glu Leu Asp Lys Gly Ile Gly Thr Ile Ile Ser Ser Pro Tyr Arg Ile
     50                  55                  60

Arg Phe Ile Ala Glu Gly His Pro Leu Ser Leu Lys Phe Asp Ser Phe
 65                  70                  75                  80

Ala Val Ile Met Leu Cys Val Gly Ile Pro Thr Glu Trp Ser Val Val
                 85                  90                  95

Glu Asp Leu Pro Glu Gly Pro Ala Val Lys Ile Gly Glu Asn Lys Asp
            100                 105                 110

Ala Met Asp Gly Trp Phe Arg Leu Glu Arg Val Ser Asp Asp Glu Phe
        115                 120                 125

Asn Asn Tyr Lys Leu Val Phe Cys Pro Gln Gln Ala Glu Asp Asp Lys
    130                 135                 140

Cys Gly Asp Ile Gly Ile Ser Ile Asp His Asp Asp Gly Thr Arg Arg
145                 150                 155                 160

Leu Val Val Ser Lys Asn Lys Pro Leu Val Val Gln Phe Gln Lys Leu
                165                 170                 175

Asp Lys Glu Ser Leu
            180

<210> SEQ ID NO 13
<211> LENGTH: 46
<212> TYPE: PRT
<213> ORGANISM: Glycine max

<400> SEQUENCE: 13

Pro Leu Thr Val Val Gln Ser Arg Asn Glu Leu Asp Lys Gly Ile Gly
  1               5                  10                  15

Thr Ile Ile Ser Ser Pro Tyr Arg Ile Arg Phe Ile Ala Glu Gly His
             20                  25                  30

Pro Leu Ser Leu Lys Phe Asp Ser Phe Ala Val Ile Met Leu
         35                  40                  45

<210> SEQ ID NO 14
<211> LENGTH: 8
<212> TYPE: PRT
<213> ORGANISM: Glycine max

<400> SEQUENCE: 14

Pro Gln Gln Ala Glu Asp Asp Lys
  1               5

<210> SEQ ID NO 15
<211> LENGTH: 71
<212> TYPE: PRT
<213> ORGANISM: Unknown
<220> FEATURE:
<223> OTHER INFORMATION: VEGF BBI variant

<400> SEQUENCE: 15
```

```
Asp Asp Glu Ser Ser Lys Pro Cys Cys Asp Gln Cys Ala Cys Tyr Asn
1               5                   10                  15

Leu Tyr Gly Trp Thr Cys Arg Cys Ser Asp Met Arg Leu Asn Ser Cys
                20                  25                  30

His Ser Ala Cys Lys Ser Cys Ile Cys Ala Leu Ser Tyr Pro Ala Gln
            35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70
```

<210> SEQ ID NO 16
<211> LENGTH: 71
<212> TYPE: PRT
<213> ORGANISM: Unknown
<220> FEATURE:
<223> OTHER INFORMATION: VEGF BBI variant

<400> SEQUENCE: 16

```
Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
                20                  25                  30

His Ser Ala Cys Lys Ser Cys Ile Cys Tyr Asn Leu Tyr Gly Trp Thr
            35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70
```

<210> SEQ ID NO 17
<211> LENGTH: 71
<212> TYPE: PRT
<213> ORGANISM: Unknown
<220> FEATURE:
<223> OTHER INFORMATION: VEGF BBI variant

<400> SEQUENCE: 17

```
Asp Asp Glu Ser Ser Lys Pro Cys Cys Asp Gln Cys Ala Cys Tyr Asn
1               5                   10                  15

Leu Tyr Gly Trp Thr Cys Arg Cys Ser Asp Met Arg Leu Asn Ser Cys
                20                  25                  30

His Ser Ala Cys Lys Ser Cys Ile Cys Tyr Asn Leu Tyr Gly Trp Thr
            35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70
```

<210> SEQ ID NO 18
<211> LENGTH: 71
<212> TYPE: PRT
<213> ORGANISM: Unknown
<220> FEATURE:
<223> OTHER INFORMATION: C2 BBI variant

<400> SEQUENCE: 18

```
Asp Asp Glu Ser Ser Lys Pro Cys Cys Asp Gln Cys Ser Cys Gly Arg
1               5                   10                  15
```

```
Lys Ile Pro Ile Gln Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
            35                  40                  45

Cys Phe Cys Val Asp Ile Thr Asp Phe Cys Tyr Glu Pro Cys Lys Pro
 50                  55                  60

Ser Glu Asp Asp Lys Glu Asn
65                   70

<210> SEQ ID NO 19
<211> LENGTH: 71
<212> TYPE: PRT
<213> ORGANISM: Unknown
<220> FEATURE:
<223> OTHER INFORMATION: C3 BBI variant

<400> SEQUENCE: 19

Asp Asp Glu Ser Ser Lys Pro Cys Cys Asp Gln Cys Gly Cys Ala Arg
 1               5                  10                  15

Ser Asn Leu Asp Glu Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
            35                  40                  45

Cys Phe Cys Val Asp Ile Thr Asp Phe Cys Tyr Glu Pro Cys Lys Pro
 50                  55                  60

Ser Glu Asp Asp Lys Glu Asn
65                   70

<210> SEQ ID NO 20
<211> LENGTH: 71
<212> TYPE: PRT
<213> ORGANISM: Unknown
<220> FEATURE:
<223> OTHER INFORMATION: C4 BBI variant

<400> SEQUENCE: 20

Asp Asp Glu Ser Ser Lys Pro Cys Cys Asp Gln Cys Gly Cys Gln Arg
 1               5                  10                  15

Ala Leu Pro Ile Leu Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
            35                  40                  45

Cys Phe Cys Val Asp Ile Thr Asp Phe Cys Tyr Glu Pro Cys Lys Pro
 50                  55                  60

Ser Glu Asp Asp Lys Glu Asn
65                   70

<210> SEQ ID NO 21
<211> LENGTH: 71
<212> TYPE: PRT
<213> ORGANISM: Unknown
<220> FEATURE:
<223> OTHER INFORMATION: C5 BBI variant

<400> SEQUENCE: 21

Asp Asp Glu Ser Ser Lys Pro Cys Cys Asp Gln Cys Gln Cys Gly Arg
 1               5                  10                  15

Leu His Met Lys Thr Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
```

```
                35                  40                  45
Cys Phe Cys Val Asp Ile Thr Asp Phe Cys Tyr Glu Pro Cys Lys Pro
         50                  55                  60

Ser Glu Asp Asp Lys Glu Asn
 65                  70

<210> SEQ ID NO 22
<211> LENGTH: 71
<212> TYPE: PRT
<213> ORGANISM: Unknown
<220> FEATURE:
<223> OTHER INFORMATION: Factor B BBI variant

<400> SEQUENCE: 22

Asp Asp Glu Ser Ser Lys Pro Cys Cys Asp Gln Cys Gln Cys Lys Arg
 1               5                  10                  15

Lys Ile Val Leu Asp Cys Arg Cys Ser Asp Met Arg Leu Asn Ser Cys
                20                  25                  30

His Ser Ala Cys Lys Ser Cys Ile Cys Ala Leu Ser Tyr Pro Ala Gln
         35                  40                  45

Cys Phe Cys Val Asp Ile Thr Asp Phe Cys Tyr Glu Pro Cys Lys Pro
         50                  55                  60

Ser Glu Asp Asp Lys Glu Asn
 65                  70

<210> SEQ ID NO 23
<211> LENGTH: 71
<212> TYPE: PRT
<213> ORGANISM: Unknown
<220> FEATURE:
<223> OTHER INFORMATION: MMP-2 BBI variant

<400> SEQUENCE: 23

Asp Asp Glu Ser Ser Lys Pro Cys Cys Asp Gln Cys Ala Cys Ala Ala
 1               5                  10                  15

Met Phe Gly Pro Ala Cys Arg Cys Ser Asp Met Arg Leu Asn Ser Cys
                20                  25                  30

His Ser Ala Cys Lys Ser Cys Ile Cys Ala Leu Ser Tyr Pro Ala Gln
         35                  40                  45

Cys Phe Cys Val Asp Ile Thr Asp Phe Cys Tyr Glu Pro Cys Lys Pro
         50                  55                  60

Ser Glu Asp Asp Lys Glu Asn
 65                  70

<210> SEQ ID NO 24
<211> LENGTH: 71
<212> TYPE: PRT
<213> ORGANISM: Unknown
<220> FEATURE:
<223> OTHER INFORMATION: MMP-12 BBI variant

<400> SEQUENCE: 24

Asp Asp Glu Ser Ser Lys Pro Cys Cys Asp Gln Cys Ala Cys Gly Ala
 1               5                  10                  15

Leu Gly Leu Phe Gly Cys Arg Cys Ser Asp Met Arg Leu Asn Ser Cys
                20                  25                  30

His Ser Ala Cys Lys Ser Cys Ile Cys Ala Leu Ser Tyr Pro Ala Gln
         35                  40                  45

Cys Phe Cys Val Asp Ile Thr Asp Phe Cys Tyr Glu Pro Cys Lys Pro
         50                  55                  60
```

```
Ser Glu Asp Asp Lys Glu Asn
65                  70

<210> SEQ ID NO 25
<211> LENGTH: 71
<212> TYPE: PRT
<213> ORGANISM: Unknown
<220> FEATURE:
<223> OTHER INFORMATION: CBP1 BBI variant

<400> SEQUENCE: 25

Asp Asp Glu Ser Ser Lys Pro Cys Cys Asp Gln Cys Ala Cys Glu Pro
 1               5                  10                  15

Leu Ile His Gln Arg Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70

<210> SEQ ID NO 26
<211> LENGTH: 71
<212> TYPE: PRT
<213> ORGANISM: Unknown
<220> FEATURE:
<223> OTHER INFORMATION: CBP2 BBI variant

<400> SEQUENCE: 26

Asp Asp Glu Ser Ser Lys Pro Cys Cys Asp Gln Cys Ala Cys Ser Ala
 1               5                  10                  15

Phe Arg Gly Pro Thr Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70

<210> SEQ ID NO 27
<211> LENGTH: 73
<212> TYPE: PRT
<213> ORGANISM: Unknown
<220> FEATURE:
<223> OTHER INFORMATION: C-statin BBI variant

<400> SEQUENCE: 27

Asp Asp Glu Ser Ser Lys Pro Cys Cys Asp Gln Cys Ala Cys Val Val
 1               5                  10                  15

Gln Asp Trp Gly His His Arg Cys Arg Cys Ser Asp Met Arg Leu Asn
            20                  25                  30

Ser Cys His Ser Ala Cys Lys Ser Cys Ile Cys Ala Leu Ser Tyr Pro
        35                  40                  45

Ala Gln Cys Phe Cys Val Asp Ile Thr Asp Phe Cys Tyr Glu Pro Cys
    50                  55                  60

Lys Pro Ser Glu Asp Asp Lys Glu Asn
65                  70
```

-continued

```
<210> SEQ ID NO 28
<211> LENGTH: 73
<212> TYPE: PRT
<213> ORGANISM: Unknown
<220> FEATURE:
<223> OTHER INFORMATION: C-statin BBI variant

<400> SEQUENCE: 28

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ile Cys Val Val Gln Asp Trp Gly His
        35                  40                  45

His Arg Cys Phe Cys Val Asp Ile Thr Asp Phe Cys Tyr Glu Pro Cys
    50                  55                  60

Lys Pro Ser Glu Asp Asp Lys Glu Asn
65                  70

<210> SEQ ID NO 29
<211> LENGTH: 73
<212> TYPE: PRT
<213> ORGANISM: Unknown
<220> FEATURE:
<223> OTHER INFORMATION: C-statin BBI variant

<400> SEQUENCE: 29

Asp Asp Glu Ser Ser Lys Pro Cys Cys Asp Gln Cys Ala Cys Val Val
1               5                   10                  15

Gln Asp Trp Gly His His Arg Cys Arg Cys Ser Asp Met Arg Leu Asn
            20                  25                  30

Ser Cys His Ser Ala Cys Lys Ser Cys Val Val Gln Asp Trp Gly His
        35                  40                  45

His Arg Cys Phe Cys Val Asp Ile Thr Asp Phe Cys Tyr Glu Pro Cys
    50                  55                  60

Lys Pro Ser Glu Asp Asp Lys Glu Asn
65                  70

<210> SEQ ID NO 30
<211> LENGTH: 9
<212> TYPE: PRT
<213> ORGANISM: Unknown
<220> FEATURE:
<223> OTHER INFORMATION: VEGF compstatin variant

<400> SEQUENCE: 30

Cys Tyr Asn Leu Tyr Gly Trp Thr Cys
1               5

<210> SEQ ID NO 31
<211> LENGTH: 11
<212> TYPE: PRT
<213> ORGANISM: Unknown
<220> FEATURE:
<223> OTHER INFORMATION: C2 compstatin variant

<400> SEQUENCE: 31

Cys Ser Cys Gly Arg Lys Ile Pro Ile Gln Cys
1               5                   10

<210> SEQ ID NO 32
<211> LENGTH: 11
```

```
<212> TYPE: PRT
<213> ORGANISM: Unknown
<220> FEATURE:
<223> OTHER INFORMATION: C3 compstatin variant

<400> SEQUENCE: 32

Cys Gly Cys Ala Arg Ser Asn Leu Asp Glu Cys
 1               5                  10

<210> SEQ ID NO 33
<211> LENGTH: 11
<212> TYPE: PRT
<213> ORGANISM: Unknown
<220> FEATURE:
<223> OTHER INFORMATION: C4 compstatin variant

<400> SEQUENCE: 33

Cys Gly Cys Gln Arg Ala Leu Pro Ile Leu Cys
 1               5                  10

<210> SEQ ID NO 34
<211> LENGTH: 11
<212> TYPE: PRT
<213> ORGANISM: Unknown
<220> FEATURE:
<223> OTHER INFORMATION: C5 compstatin variant

<400> SEQUENCE: 34

Cys Gln Cys Gly Arg Leu His Met Lys Thr Cys
 1               5                  10

<210> SEQ ID NO 35
<211> LENGTH: 11
<212> TYPE: PRT
<213> ORGANISM: Unknown
<220> FEATURE:
<223> OTHER INFORMATION: Factor B compstatin variant

<400> SEQUENCE: 35

Cys Gln Cys Lys Arg Lys Ile Val Leu Asp Cys
 1               5                  10

<210> SEQ ID NO 36
<211> LENGTH: 9
<212> TYPE: PRT
<213> ORGANISM: Unknown
<220> FEATURE:
<223> OTHER INFORMATION: MMP-2 compstatin variant

<400> SEQUENCE: 36

Cys Ala Ala Met Phe Gly Pro Ala Cys
 1               5

<210> SEQ ID NO 37
<211> LENGTH: 9
<212> TYPE: PRT
<213> ORGANISM: Unknown
<220> FEATURE:
<223> OTHER INFORMATION: MMP-12 compstatin variant

<400> SEQUENCE: 37

Cys Gly Ala Leu Gly Leu Phe Gly Cys
 1               5

<210> SEQ ID NO 38
<211> LENGTH: 9
<212> TYPE: PRT
```

```
<213> ORGANISM: Unknown
<220> FEATURE:
<223> OTHER INFORMATION: cotton binding peptide compstatin variant

<400> SEQUENCE: 38

Cys Glu Pro Leu Ile His Gln Arg Cys
 1               5

<210> SEQ ID NO 39
<211> LENGTH: 9
<212> TYPE: PRT
<213> ORGANISM: Unknown
<220> FEATURE:
<223> OTHER INFORMATION: cotton binding peptide compstatin variant

<400> SEQUENCE: 39

Cys Ser Ala Phe Arg Gly Pro Thr Cys
 1               5

<210> SEQ ID NO 40
<211> LENGTH: 11
<212> TYPE: PRT
<213> ORGANISM: Unknown
<220> FEATURE:
<223> OTHER INFORMATION: compstatin variant

<400> SEQUENCE: 40

Cys Val Val Gln Asp Trp Gly His His Arg Cys
 1               5                  10

<210> SEQ ID NO 41
<211> LENGTH: 8970
<212> TYPE: DNA
<213> ORGANISM: Artificial Sequence
<220> FEATURE:
<223> OTHER INFORMATION: synthetic pTREX2 nucleotide sequence

<400> SEQUENCE: 41
aagcttaagg tgcacggccc acgtggccac tagtacttct cgagctctgt acatgtccgg      60
tcgcgacgta cgcgtatcga tggcgccagc tgcaggcggc cgcctgcagc cacttgcagt     120
cccgtggaat tctcacggtg aatgtaggcc ttttgtaggg taggaattgt cactcaagca     180
cccccaacct ccattacgcc tcccccatag agttcccaat cagtgagtca tggcactgtt     240
ctcaaataga ttggggagaa gttgacttcc gcccagagct gaaggtcgca caaccgcatg     300
atatagggtc ggcaacggca aaaagcacg tggctcaccg aaaagcaaga tgtttgcgat     360
ctaacatcca ggaacctgga tacatccatc atcacgcacg accactttga tctgctggta     420
aactcgtatt cgccctaaac cgaagtgcgt ggtaaatcta cacgtgggcc ctttcggta      480 tactgcgtgt gtcttctcta ggtgccattc ttttcccttc ctctagtgtt gaattgtttg     540
tgttggagtc cgagctgtaa ctacctctga atctctggag aatggtggac taacgactac     600
cgtgcacctg catcatgtat ataatagtga tcctgagaag gggggtttgg agcaatgtgg     660
gactttgatg gtcatcaaac aaagaacgaa gacgcctctt ttgcaaagtt ttgtttcggc     720
tacggtgaag aactggatac ttgttgtgtc ttctgtgtat ttttgtggca acaagaggcc     780
agagacaatc tattcaaaca ccaagcttgc tcttttgagc tacaagaacc tgtggggtat     840
atatctagag ttgtgaagtc ggtaatcccg ctgtatagta atacgagtcg catctaaata     900
ctccgaagct gctgcgaacc cggagaatcg agatgtgctg gaaagcttct agcgagcggc     960
taaattagca tgaaaggcta tgagaaattc tggagacggc ttgttgaatc atggcgttcc    1020
```

```
attcttcgac aagcaaagcg ttccgtcgca gtagcaggca ctcattcccg aaaaaactcg    1080
gagattccta agtagcgatg gaaccggaat aatataatag gcaatacatt gagttgcctc    1140
gacggttgca atgcaggggt actgagcttg gacataactg ttccgtaccc cacctcttct    1200
caacctttgg cgtttccctg attcagcgta cccgtacaag tcgtaatcac tattaaccca    1260
gactgaccgg acgtgttttg cccttcattt ggagaaataa tgtcattgcg atgtgtaatt    1320
tgcctgcttg accgactggg gctgttcgaa gcccgaatgt aggattgtta tccgaactct    1380
gctcgtagag gcatgttgtg aatctgtgtc gggcaggaca cgcctcgaag gttcacggca    1440
agggaaacca ccgatagcag tgtctagtag caacctgtaa agccgcaatg cagcatcact    1500
ggaaaataca aaccaatggc taaaagtaca taagttaatg cctaaagaag tcatatacca    1560
gcggctaata attgtacaat caagtggcta acgtaccgt aatttgccaa cggcttgtgg    1620
ggttgcagaa gcaacggcaa agccccactt ccccacgttt gtttcttcac tcagtccaat    1680
ctcagctggt gatcccccaa ttgggtcgct tgtttgttcc ggtgaagtga aagaagacag    1740
aggtaagaat gtctgactcg gagcgttttg catacaacca agggcagtga tggaagacag    1800
tgaaatgttg acattcaagg agtatttagc cagggatgct tgagtgtatc gtgtaaggag    1860
gtttgtctgc cgatacgacg aatactgtat agtcacttct gatgaagtgg tccatattga    1920
aatgtaagtc ggcactgaac aggcaaaaga ttgagttgaa actgcctaag atctcgggcc    1980
ctcgggcctt cggcctttgg gtgtacatgt ttgtgctccg ggcaaatgca aagtgtggta    2040
ggatcgaaca cactgctgcc tttaccaagc agctgagggt atgtgatagg caaatgttca    2100
ggggccactg catggtttcg aatagaaaga gaagcttagc caagaacaat agccgataaa    2160
gatagcctca ttaaacggaa tgagctagta ggcaaagtca gcgaatgtgt atatataaag    2220
gttcgaggtc cgtgcctccc tcatgctctc cccatctact catcaactca gatcctccag    2280
gagacttgta caccatcttt tgaggcacag aaacccaata gtcaaccgcg gtttaggcgc    2340
gccagctccg tgcgaaagcc tgacgcaccg gtagattctt ggtgagcccg tatcatgacg    2400
gcggcgggag ctacatggcc ccgggtgatt tatttttttt gtatctactt ctgacccttt    2460
tcaaatatac ggtcaactca tcttttcactg gagatgcggc ctgcttggta ttgcgatgtt    2520
gtcagcttgg caaattgtgg ctttcgaaaa cacaaaacga ttccttagta gccatgcatt    2580
ttaagataac ggaatagaag aaagaggaaa ttaaaaaaaa aaaaaaaaca aacatcccgt    2640
tcataacccg tagaatcgcc gctcttcgtg tatcccagta ccagttaaa cggatctcaa    2700 gcttgcatgc aaagatacac atcaatcgca gctggggtac aatcatccat catcccaact    2760
ggtacgtcat aacaaaaatc gacaagatgg aaaagaggt cgcctaaata cagctgcatt    2820
ctatgatgcc gggctttgga caagagctct ttctcagctc cgtttgtcct ccctcccttt    2880 tccccttct tgctaaatgc ctttctttac ttctttcttc ccttccctcc cctatcgcag    2940
cagcctctcg gtgtaggctt tccacgctgc tgatcggtac cgctctgcct cctctacggg    3000
gtctgaggcc ttgaggatgc cccggcccac aatggcaatg tcgctgccgg cgatgccaat    3060
cagcttgtgc ggcgtgttgt actgctggcc ctggccgtct ccaccgaccg atccgttggt    3120
ctgctggtcc tcgtcttcgg ggggcagctg gcagccgggc gtcatgtgga taaaggcatc    3180
gtcgggctcg gtgttgagcg tctcctgcga gatgaagccc atgacaaagt ccttgtgctc    3240
ccgggcggcc tcgacgcagg cctgcgtgta ctccttgttc atgaagttgc cctggctgga    3300
catttgggcg aggatcagga ggcctcggct cagcggcgcc tcctcgatgc ccgggaagag    3360
cgactcgtcg ccctcggcga tggccttgt taaccggggc gaggagacgg actcgtactg    3420
```

```
ctgggtgacg gtggtgatgg agacgatgct gcccttgcgg ccgtcgccgg accggttcga    3480
gtagatgggc ttgtccagga cgccaatgga gcccatgccg ttgacggcgc cggcgggctc    3540
ggcgtccctg gagtcggcgt cgtcgtcaaa cgagtccatg gtgggcgtgc cgacggtgac    3600
ggacgtcttg acctcgcagg ggtagcgctc gagccagcgc ttggcgccct gggccagcga    3660
ggccaccgac gccttgccgg gcaccatgtt gacgttgaca atgtgcgccc agtcgatgat    3720
gcgcgccgac ccgcccgtgt actgcagctc gacggtgtgg ccaatgtcgc caaacttgcg    3780
gtcctcgaag atgaggaagc cgtgcttgcg cgccagcgac gccagctggg ctcccgtgcc    3840
cgtctccggg tggaagtccc agcccgagac catgtcgtag tgcgtcttga gcacgacaat    3900
cgacgggcca atcttgtcgg ccaggtacag cagctcgcgc gctgtcggca cgtcggcgct    3960
caggcacagg ttgacgcct tgaggtccat gagcttgaac aggtaagccg tcagcgggtg    4020
cgtcgccgtc tcgctcctgg ccgcgaaggt ggccttgagc gtcgggtgtg gtgccatggc    4080
tgatgaggct gagagaggct gaggctgcgg ctggttggat agtttaaccc ttagggtgcc    4140
gttgtgcgg tttagagggg gggaaaaaaa agagagagat ggcacaattc tgctgtgcga    4200
atgacgttgg aagcgcgaca gccgtgcggg aggaagagga gtaggaactg tcggcgattg    4260
ggagaatttc gtgcgatccg agtcgtctcg aggcgaggga gttgctttaa tgtcgggctc    4320
gtccctggt caaaattcta gggagcagcg ctggcaacga gagcagagca gcagtagtcg    4380
atgctagaaa tcgatagatc cacgatgcca aaaagcttgt tcatttcggc tagcccgtga    4440
tcctggcgct tctagggctg aaactgtgtt gttaatgtat tattggctgt gtaactgact    4500
tgaatgggga atgaggagcg cgatggattc gcttgcatgt cccctggcca agacgagccg    4560
ctttggcggt ttgtgattcg aaggtgtgtc agcggaggcg ccagggcaac acgcactgag    4620
ccagccaaca tgcattgctg ccgacatgaa tagacacgcg ccgagcagac ataggagacg    4680
tgttgactgt aaaaattcta ctgaatatta gcacgcatgt tctcaataag agcaatagga    4740
atgcttgcca atcataagta cgtatgtgct ttttcctgca aatggtacgt acggacagtt    4800
catgttgtct gtcatccccc actcaggctc tcatgatcat tttatgggac tggggttttg    4860
ctgactgaat ggattcagcc gcacgaaaca aattggggc catgcagaag gaagccccc     4920
ccagccccct gttcataatt tgttaagagt cggagagctg cctagtatga agcagcaatt    4980
gataacgttg actttgcgca tgagctctga agccgggcat atgtatcacg tttctgccta    5040
gagccgcacg ggacccaaga agctcttgtc ataaggtatt tatgagtgtt cagctgccaa    5100
cgctggttct actttggctc aaccgcatcc cataagctga actttgggag ctgccagaat    5160
gtctcttgat gtacagcgat caacaaccgt gcgccggtcg acaactgttc accgatcagg    5220
gacgcgaaga ggacccaatc ccggttaacg cacctgctcc gaagaagcaa aagggctatg    5280
aggtggtgca gcaaggaatc aaagagctct atccacttga caaggccaat gtcgctcccg    5340
atctggagta agtcaaccct gaagtggaag tttgcttctc tgattagtat gtagcatcgt    5400
gtttgtccca ggactgggtg caaatcccga agacagctgg aagtccagca agaccgactt    5460
caattggacc acgcatacag atggcctcca gagagacttc ccaagagctc ggttgcttct    5520
gtatatgtac gactcagcat ggactggcca gctcaaagta aaacaattca tgggcaatat    5580
cgcgatgggg ctcttggttg ggctgaggag caagagagag gtaggccaaa cgccagactc    5640
gaaccgccag ccaagtctca aactgactgc aggcggccgc catatgcatc ctaggcctat    5700
taatattccg gagtatacgt agccggctaa cgttaacaac cggtacctct agaactatag    5760
```

| | |
|---|---|
| ctagcatgcg caaatttaaa gcgctgatat cgatcgcgcg cagatccata tagggccc | 5820 |
| gggttataat tacctcaggt cgacgtccca tggccattcg aattcgtaat catggtcata | 5880 |
| gctgtttcct gtgtgaaatt gttatccgct cacaattcca cacaacatac gagccggaag | 5940 |
| cataaagtgt aaagcctggg gtgcctaatg agtgagctaa ctcacattaa ttgcgttgcg | 6000 |
| ctcactgccc gctttccagt cgggaaacct gtcgtgccag ctgcattaat gaatcggcca | 6060 |
| acgcgcgggg agaggcggtt tgcgtattgg gcgctcttcc gcttcctcgc tcactgactc | 6120 |
| gctgcgctcg tcgttcggc tgcggcgagc ggtatcagct cactcaaagg cggtaatacg | 6180 |
| gttatccaca gaatcagggg ataacgcagg aaagaacatg tgagcaaaag gccagcaaaa | 6240 |
| ggccaggaac cgtaaaaagg ccgcgttgct ggcgtttttc cataggctcc gcccccctga | 6300 |
| cgagcatcac aaaaatcgac gctcaagtca gaggtggcga acccgacag gactataaag | 6360 |
| ataccaggcg tttccccctg gaagctccct cgtgcgctct cctgttccga ccctgccgct | 6420 |
| taccggatac ctgtccgcct ttctcccttc gggaagcgtg gcgctttctc atagctcacg | 6480 |
| ctgtaggtat ctcagttcgg tgtaggtcgt tcgctccaag ctgggctgtg tgcacgaacc | 6540 |
| ccccgttcag cccgaccgct gcgccttatc cggtaactat cgtcttgagt ccaacccggt | 6600 |
| aagacacgac ttatcgccac tggcagcagc cactggtaac aggattagca gagcgaggta | 6660 |
| tgtaggcggt gctacagagt tcttgaagtg gtggcctaac tacggctaca ctagaagaac | 6720 |
| agtatttggt atctgcgctc tgctgaagcc agttaccttc ggaaaaagag ttggtagctc | 6780 |
| ttgatccggc aaacaaacca ccgctggtag cggtggtttt tttgtttgca agcagcagat | 6840 |
| tacgcgcaga aaaaaggat ctcaagaaga tcctttgatc ttttctacgg ggtctgacgc | 6900 |
| tcagtggaac gaaaactcac gttaagggat tttggtcatg agattatcaa aaaggatctt | 6960 |
| cacctagatc cttttaaatt aaaaatgaag ttttaaatca atctaaagta tatatgagta | 7020 |
| aacttggtct gacagttacc aatgcttaat cagtgaggca cctatctcag cgatctgtct | 7080 |
| atttcgttca tccatagttg cctgactccc cgtcgtgtag ataactacga tacgggaggg | 7140 |
| cttaccatct ggccccagtg ctgcaatgat accgcgagac ccacgctcac cggctccaga | 7200 |
| tttatcagca ataaaccagc cagccggaag ggccgagcgc agaagtggtc ctgcaacttt | 7260 |
| atccgcctcc atccagtcta ttaattgttg ccgggaagct agagtaagta gttcgccagt | 7320 |
| taatagtttg cgcaacgttg ttgccattgc tacaggcatc gtggtgtcac gctcgtcgtt | 7380 |
| tggtatggct tcattcagct ccggttccca acgatcaagg cgagttacat gatccccat | 7440 |
| gttgtgcaaa aaagcggtta gctccttcgg tcctccgatc gttgtcagaa gtaagttggc | 7500 |
| cgcagtgtta tcactcatgg ttatggcagc actgcataat tctcttactg tcatgccatc | 7560 |
| cgtaagatgc ttttctgtga ctggtgagta ctcaaccaag tcattctgag aatagtgtat | 7620 |
| gcggcgaccg agttgctctt gcccggcgtc aatacgggat aataccgcgc cacatagcag | 7680 |
| aactttaaaa gtgctcatca ttggaaaacg ttcttcgggg cgaaaactct caaggatctt | 7740 |
| accgctgttg agatccagtt cgatgtaacc cactcgtgca cccaactgat cttcagcatc | 7800 |
| ttttactttc accagcgttt ctgggtgagc aaaaacagga aggcaaaatg ccgcaaaaaa | 7860 |
| gggaataagg gcgacacgga aatgttgaat actcatactc ttcctttttc aatattattg | 7920 |
| aagcatttat cagggttatt gtctcatgag cggatacata tttgaatgta tttagaaaaa | 7980 |
| taaacaaata ggggttccgc gcacatttcc ccgaaaagtg ccacctgacg tctaagaaac | 8040 |
| cattattatc atgacattaa cctataaaaa taggcgtatc acgaggccct ttcgtctcgc | 8100 |
| gcgtttcggt gatgacggtg aaaacctctg acacatgcag ctcccggaga cggtcacagc | 8160 |

-continued

```
ttgtctgtaa gcggatgccg ggagcagaca agcccgtcag ggcgcgtcag cgggtgttgg    8220
cgggtgtcgg ggctggctta actatgcggc atcagagcag attgtactga gagtgcacca    8280
taaaattgta acgttaata ttttgttaaa attcgcgtta aattttgtt aaatcagctc      8340 attttttaac caataggccg aaatcggcaa atcccttat aaatcaaaag aatagcccga     8400
gatagggttg agtgttgttc cagtttggaa caagagtcca ctattaaaga acgtggactc    8460
caacgtcaaa gggcgaaaaa ccgtctatca gggcgatggc ccactacgtg aaccatcacc    8520
caaatcaagt tttttggggt cgaggtgccg taaagcacta atcggaacc ctaaagggag     8580 cccccgattt agagcttgac ggggaaagcc ggcgaacgtg gcgagaaagg aagggaagaa    8640
agcgaaagga gcgggcgcta gggcgctggc aagtgtagcg gtcacgctgc gcgtaaccac    8700
cacacccgcc gcgcttaatg cgccgctaca gggcgcgtac tatggttgct ttgacgtatg    8760
cggtgtgaaa taccgcacag atgcgtaagg agaaaatacc gcatcaggcg ccattcgcca    8820
ttcaggctgc gcaactgttg ggaagggcga tcggtgcggg cctcttcgct attacgccag    8880
ctggcgaaag ggggatgtgc tgcaaggcga ttaagttggg taacgccagg gttttcccag    8940
tcacgacgtt gtaaaacgac ggccagtgcc                                    8970
```

<210> SEQ ID NO 42
<211> LENGTH: 253
<212> TYPE: DNA
<213> ORGANISM: Artificial Sequence
<220> FEATURE:
<223> OTHER INFORMATION: synthetic

<400> SEQUENCE: 42

```
gctagcgacg atgagagctc taagccctgt tgcgatcagt gcgcgtgtac caaatcgaac     60
cctccgcagt gtcgctgctc cgatatgcgt ctgaattcct gtcatagcgc atgcaagagc    120
tgtatctgcg ccctgagcta ccccgcgcag tgtttctgcg tcgacatcac ggacttctgc    180
tacgagccgt gtaagcccag cgaggacgat aaggagaacc atcatcacca tcaccattag    240
ctcgagggtg acc                                                      253
```

<210> SEQ ID NO 43
<211> LENGTH: 23
<212> TYPE: DNA
<213> ORGANISM: Artificial Sequence
<220> FEATURE:
<223> OTHER INFORMATION: primer

<400> SEQUENCE: 43

```
gggctagcaa cgtcatctcc aag                                            23
```

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44

```
ggggtcacct agttctcctt atcgtcctcg ctg                                 33
```

<210> SEQ ID NO 45
<211> LENGTH: 44
<212> TYPE: DNA
<213> ORGANISM: Artificial Sequence
<220> FEATURE:

<223> OTHER INFORMATION: primer

<400> SEQUENCE: 45
gggctagcaa cgtcatctcc aagcgcgacg atgagagctc taag             44

<210> SEQ ID NO 46
<211> LENGTH: 51
<212> TYPE: DNA
<213> ORGANISM: Artificial Sequence
<220> FEATURE:
<223> OTHER INFORMATION: primer

<400> SEQUENCE: 46
gttgcgatca gtgcgcgtgt tacaatctgt atggctggac ctgtcgctgc t      51

<210> SEQ ID NO 47
<211> LENGTH: 51
<212> TYPE: DNA
<213> ORGANISM: Artificial Sequence
<220> FEATURE:
<223> OTHER INFORMATION: primer

<400> SEQUENCE: 47
cgcatatcgg agcagcgaca ggtccagcca tacagattgt aacacgcgca c      51

<210> SEQ ID NO 48
<211> LENGTH: 52
<212> TYPE: DNA
<213> ORGANISM: Artificial Sequence
<220> FEATURE:
<223> OTHER INFORMATION: primer

<400> SEQUENCE: 48
catgcaagag ctgtatctgc tacaatctgt atggctggac ccagtgtttc tg     52

<210> SEQ ID NO 49
<211> LENGTH: 52
<212> TYPE: DNA
<213> ORGANISM: Artificial Sequence
<220> FEATURE:
<223> OTHER INFORMATION: primer

<400> SEQUENCE: 49
gatgtcgacg cagaaacact gggtccagcc atacagattg tagcagatac ag     52

<210> SEQ ID NO 50
<211> LENGTH: 69
<212> TYPE: DNA
<213> ORGANISM: Artificial Sequence
<220> FEATURE:
<223> OTHER INFORMATION: primer

<400> SEQUENCE: 50
gcgatcagtg cagctgtagc tgcggcagga agatccccat ccagtgctgt cgctgctccg    60
atatgcgtc                                                             69

<210> SEQ ID NO 51
<211> LENGTH: 69
<212> TYPE: DNA
<213> ORGANISM: Artificial Sequence
<220> FEATURE:
<223> OTHER INFORMATION: primer

<400> SEQUENCE: 51
gagcagcgac agcactggat ggggatcttc ctgccgcagc tacagctgca ctgatcgcaa    60

```
cagggctta                                                                    69

<210> SEQ ID NO 52
<211> LENGTH: 60
<212> TYPE: DNA
<213> ORGANISM: Artificial Sequence
<220> FEATURE:
<223> OTHER INFORMATION: primer

<400> SEQUENCE: 52
gcgatcagtg cggctgtgcc aggagcaacc tcgacgagtg tcgctgctcc gatatgcgtc    60

<210> SEQ ID NO 53
<211> LENGTH: 60
<212> TYPE: DNA
<213> ORGANISM: Artificial Sequence
<220> FEATURE:
<223> OTHER INFORMATION: primer

<400> SEQUENCE: 53
gagcagcgac actcgtcgag gttgctcctg gcacagccgc actgatcgca acagggctta    60

<210> SEQ ID NO 54
<211> LENGTH: 280
<212> TYPE: DNA
<213> ORGANISM: Glycine max

<400> SEQUENCE: 54
gctagcaacg tcatctccaa gcgcggcggt ggcgacgatg agagctctaa gccctgttgc    60
gatcagtgcg cgtgtaccaa atcgaaccct ccgcagtgtc gctgctccga tatgcgtctg   120
aattcctgtc atagcgcatg caagagctgt atctgcgccc tgagctaccc cgcgcagtgt   180
ttctgcgtcg acatcacgga cttctgctac gagccgtgta agcccagcga ggacgataag   240
gagaaccacc atcaccatca ccactagctc gagggtgacc                          280

<210> SEQ ID NO 55
<211> LENGTH: 60
<212> TYPE: DNA
<213> ORGANISM: Artificial Sequence
<220> FEATURE:
<223> OTHER INFORMATION: primer

<400> SEQUENCE: 55
gcgatcagtg cgcgtgtcag agggccctcc ccatcctctg tcgctgctcc gatatgcgtc    60

<210> SEQ ID NO 56
<211> LENGTH: 60
<212> TYPE: DNA
<213> ORGANISM: Artificial Sequence
<220> FEATURE:
<223> OTHER INFORMATION: primer

<400> SEQUENCE: 56
gagcagcgac agaggatggg gagggccctc tgacacgcgc actgatcgca acagggctta    60

<210> SEQ ID NO 57
<211> LENGTH: 60
<212> TYPE: DNA
<213> ORGANISM: Artificial Sequence
<220> FEATURE:
<223> OTHER INFORMATION: primer

<400> SEQUENCE: 57
```

```
gcgatcagtg ccagtgtggc aggctccaca tgaagacctg tcgctgctcc gatatgcgtc    60
```

<210> SEQ ID NO 58
<211> LENGTH: 62
<212> TYPE: DNA
<213> ORGANISM: Artificial Sequence
<220> FEATURE:
<223> OTHER INFORMATION: primer
<400> SEQUENCE: 58

```
gagcagcgac aggtcttcat gtggagcctg ccacactggc actgatcgca acagggctta    60
ga                                                                  62
```

<210> SEQ ID NO 59
<211> LENGTH: 60
<212> TYPE: DNA
<213> ORGANISM: Artificial Sequence
<220> FEATURE:
<223> OTHER INFORMATION: primer
<400> SEQUENCE: 59

```
gcgatcagtg ccagtgtaag aggaagatcg tcctcgactg tcgctgctcc gatatgcgtc    60
```

<210> SEQ ID NO 60
<211> LENGTH: 62
<212> TYPE: DNA
<213> ORGANISM: Artificial Sequence
<220> FEATURE:
<223> OTHER INFORMATION: primer
<400> SEQUENCE: 60

```
gagcagcgac agtcgaggac gatcttcctc ttacactggc actgatcgca acagggctta    60
ga                                                                  62
```

<210> SEQ ID NO 61
<211> LENGTH: 55
<212> TYPE: DNA
<213> ORGANISM: Artificial Sequence
<220> FEATURE:
<223> OTHER INFORMATION: primer
<400> SEQUENCE: 61

```
cagtgcgcgt gtgccgccat gttcggcccc gcctgtcgct gctccgatat gcgtc         55
```

<210> SEQ ID NO 62
<211> LENGTH: 54
<212> TYPE: DNA
<213> ORGANISM: Artificial Sequence
<220> FEATURE:
<223> OTHER INFORMATION: primer
<400> SEQUENCE: 62

```
gagcagcgac aggcggggcc gaacatggcg gcacacgcgc actgatcgca acag          54
```

<210> SEQ ID NO 63
<211> LENGTH: 55
<212> TYPE: DNA
<213> ORGANISM: Artificial Sequence
<220> FEATURE:
<223> OTHER INFORMATION: primer
<400> SEQUENCE: 63

```
cagtgcgcgt gtggcgccct cggcctcttc ggctgtcgct gctccgatat gcgtc         55
```

```
<210> SEQ ID NO 64
<211> LENGTH: 54
<212> TYPE: DNA
<213> ORGANISM: Artificial Sequence
<220> FEATURE:
<223> OTHER INFORMATION: primer

<400> SEQUENCE: 64
gagcagcgac agccgaagag gccgagggcg ccacacgcgc actgatcgca acag           54

<210> SEQ ID NO 65
<211> LENGTH: 51
<212> TYPE: DNA
<213> ORGANISM: Artificial Sequence
<220> FEATURE:
<223> OTHER INFORMATION: primer

<400> SEQUENCE: 65
gttgcgatca gtgcgcgtgt gagcccctga tccaccagcg ctgtcgctgc t              51

<210> SEQ ID NO 66
<211> LENGTH: 51
<212> TYPE: DNA
<213> ORGANISM: Artificial Sequence
<220> FEATURE:
<223> OTHER INFORMATION: primer

<400> SEQUENCE: 66
cgcatatcgg agcagcgaca gcgctggtgg atcaggggct cacacgcgca c              51

<210> SEQ ID NO 67
<211> LENGTH: 51
<212> TYPE: DNA
<213> ORGANISM: Artificial Sequence
<220> FEATURE:
<223> OTHER INFORMATION: primer

<400> SEQUENCE: 67
gttgcgatca gtgcgcgtgt agcgccttcc gcggccccac ctgtcgctgc t              51

<210> SEQ ID NO 68
<211> LENGTH: 51
<212> TYPE: DNA
<213> ORGANISM: Artificial Sequence
<220> FEATURE:
<223> OTHER INFORMATION: primer

<400> SEQUENCE: 68
cgcatatcgg agcagcgaca ggtggggccg cggaaggcgc tacacgcgca c              51

<210> SEQ ID NO 69
<211> LENGTH: 57
<212> TYPE: DNA
<213> ORGANISM: Artificial Sequence
<220> FEATURE:
<223> OTHER INFORMATION: primer

<400> SEQUENCE: 69
gttgcgatca gtgcgcgtgt gttgttcagg actggggcca ccaccgctgt cgctgct       57

<210> SEQ ID NO 70
<211> LENGTH: 57
<212> TYPE: DNA
<213> ORGANISM: Artificial Sequence
<220> FEATURE:
<223> OTHER INFORMATION: primer
```

```
<400> SEQUENCE: 70
cgcatatcgg agcagcgaca gcggtggtgg ccccagtcct gaacaacaca cgcgcac          57

<210> SEQ ID NO 71
<211> LENGTH: 57
<212> TYPE: DNA
<213> ORGANISM: Artificial Sequence
<220> FEATURE:
<223> OTHER INFORMATION: primer

<400> SEQUENCE: 71
catgcaagag ctgtatctgc gttgttcagg actggggcca ccaccgctgt ttctgcg          57

<210> SEQ ID NO 72
<211> LENGTH: 57
<212> TYPE: DNA
<213> ORGANISM: Artificial Sequence
<220> FEATURE:
<223> OTHER INFORMATION: primer

<400> SEQUENCE: 72
gtgatgtcga cgcagaaaca gcggtggtgg ccccagtcct gaacaacgca gatacag          57

<210> SEQ ID NO 73
<211> LENGTH: 29
<212> TYPE: DNA
<213> ORGANISM: Artificial Sequence
<220> FEATURE:
<223> OTHER INFORMATION: primer

<400> SEQUENCE: 73
ggactagtaa gcgcgacgat gagagctct                                         29

<210> SEQ ID NO 74
<211> LENGTH: 29
<212> TYPE: DNA
<213> ORGANISM: Artificial Sequence
<220> FEATURE:
<223> OTHER INFORMATION: primer

<400> SEQUENCE: 74
aaggcgcgcc tagttctcct tatcgtcct                                         29

<210> SEQ ID NO 75
<211> LENGTH: 38
<212> TYPE: DNA
<213> ORGANISM: Artificial Sequence
<220> FEATURE:
<223> OTHER INFORMATION: primer

<400> SEQUENCE: 75
ggactagtaa gcgcggcggt ggcgacgatg agagctct                               38

<210> SEQ ID NO 76
<211> LENGTH: 6
<212> TYPE: PRT
<213> ORGANISM: Glycine max

<400> SEQUENCE: 76

Asn Val Ile Ser Lys Arg
 1               5
```